United States Patent
Weerakoon et al.

(10) Patent No.: US 11,697,021 B2
(45) Date of Patent: *Jul. 11, 2023

(54) CURRENT GENERATION ARCHITECTURE FOR AN IMPLANTABLE STIMULATOR DEVICE TO PROMOTE CURRENT STEERING BETWEEN ELECTRODES

(71) Applicant: Boston Scientific Neuromodulation Corporation, Valencia, CA (US)

(72) Inventors: Pujitha Weerakoon, Valencia, CA (US); David M. Wagenbach, Simi Valley, CA (US); Philip L. Weiss, Sherman Oaks, CA (US); Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 251 days.

This patent is subject to a terminal disclaimer.

(21) Appl. No.: 17/140,850

(22) Filed: Jan. 4, 2021

(65) Prior Publication Data
US 2021/0121701 A1 Apr. 29, 2021

Related U.S. Application Data

(63) Continuation of application No. 16/131,809, filed on Sep. 14, 2018, now Pat. No. 10,912,942.
(Continued)

(51) Int. Cl.
*A61N 1/36* (2006.01)
*A61N 1/02* (2006.01)
(Continued)

(52) U.S. Cl.
CPC ......... *A61N 1/36157* (2013.01); *A61N 1/025* (2013.01); *A61N 1/36125* (2013.01); *H03M 1/72* (2013.01); *H03M 1/745* (2013.01)

(58) Field of Classification Search
None
See application file for complete search history.

(56) References Cited

U.S. PATENT DOCUMENTS 6,181,969 B1   1/2001  Gord
6,516,227 B1   2/2003  Meadows et al.
(Continued)

FOREIGN PATENT DOCUMENTS

WO   2018/048914   3/2018
WO   2018/048923   3/2018

OTHER PUBLICATIONS

Search Report and Written Opinion issued in Corresponding Netherlands Application Serial No. NL2019707 (dated Jun. 13, 2018).

*Primary Examiner* — Kennedy Schaetzle
(74) *Attorney, Agent, or Firm* — Lewis & Reese, PLLC

(57) ABSTRACT

An implantable pulse generator (IPG) is disclosed having an improved ability to steer anodic and cathodic currents between the IPG's electrodes. Each electrode node has at least one PDAC/NDAC pair to source/sink or sink/source a stimulation current to an associated electrode node. Each PDAC and NDAC receives a current with a magnitude indicative of a total anodic and cathodic current, and data indicative of a percentage of that total that each PDAC and NDAC will produce in the patient's tissue at any given time, which activates a number of branches in each PDAC or NDAC. Each PDAC and NDAC may also receive one or more resolution control signals specifying an increment by which the stimulation current may be adjusted at each electrode. The current received by each PDAC and NDAC is generated by a master DAC, and is preferably distributed to the PDACs and NDACs by distribution circuitry.

20 Claims, 31 Drawing Sheets

Related U.S. Application Data

(60) Provisional application No. 62/559,247, filed on Sep. 15, 2017.

(51) Int. Cl.
*H03M 1/74* (2006.01)
*H03M 1/72* (2006.01)

(56) References Cited

U.S. PATENT DOCUMENTS

| | | | |
|---|---|---|---|
| 6,553,263 B1 | 4/2003 | Meadows et al. | |
| 7,127,298 B1 | 10/2006 | He et al. | |
| 7,177,698 B2 | 2/2007 | Klosterman et al. | |
| 7,444,181 B2 | 10/2008 | Shi et al. | |
| 7,539,538 B2 | 5/2009 | Parramon et al. | |
| 7,623,916 B2 | 11/2009 | Julian | |
| 7,801,600 B1 | 9/2010 | Carbunaru et al. | |
| 7,801,602 B2 | 9/2010 | McClure et al. | |
| 7,872,884 B2 | 1/2011 | Parramon et al. | |
| 7,881,803 B2 | 2/2011 | Parramon et al. | |
| 7,890,182 B2 | 2/2011 | Parramon et al. | |
| 8,606,362 B2 | 12/2013 | He et al. | |
| 8,620,436 B2 | 12/2013 | Parramon et al. | |
| 8,649,858 B2 | 2/2014 | Griffith et al. | |
| 8,768,453 B2 | 7/2014 | Parramon et al. | |
| 8,996,117 B2 | 3/2015 | Trier et al. | |
| 9,002,465 B2 | 4/2015 | Rann | |
| 9,008,790 B2 | 4/2015 | Griffith et al. | |
| 9,037,241 B2 | 5/2015 | Lamont et al. | |
| 9,061,140 B2 | 6/2015 | Shi et al. | |
| 9,155,891 B2 | 10/2015 | Archer | |
| 9,174,051 B2 | 11/2015 | Marnfeldt et al. | |
| 9,220,901 B2 | 12/2015 | Gumraj et al. | |
| 9,233,254 B2 | 1/2016 | Nimmagadda et al. | |
| 9,259,574 B2 | 2/2016 | Aghassian et al. | |
| 9,259,578 B2 | 2/2016 | Torgerson | |
| 9,308,373 B2 | 4/2016 | Lee | |
| 9,314,632 B2 | 4/2016 | Marnfeldt et al. | |
| 9,327,135 B2 | 5/2016 | Vansickle et al. | |
| 9,352,162 B2 | 5/2016 | Lamont et al. | |
| 9,397,639 B2 | 7/2016 | Feldman et al. | |
| 9,446,241 B2 | 9/2016 | Lee | |
| 9,522,270 B2 | 12/2016 | Perryman et al. | |
| 9,604,061 B2 | 3/2017 | Archer | |
| 10,912,942 B2 * | 2/2021 | Weerakoon | A61N 1/025 |
| 11,116,979 B2 | 9/2021 | Chatalic et al. | |
| 2002/0072770 A1 | 6/2002 | Pless | |
| 2003/0139781 A1 | 7/2003 | Bradley et al. | |
| 2003/0153959 A1 | 8/2003 | Thacker et al. | |
| 2006/0173493 A1 | 8/2006 | Armstrong et al. | |
| 2007/0038250 A1 | 2/2007 | He et al. | |
| 2007/0100399 A1 | 5/2007 | Parramon et al. | |
| 2010/0106231 A1 | 4/2010 | Torgerson et al. | |
| 2010/0268309 A1 | 10/2010 | Parramon et al. | |
| 2011/0160810 A1 | 6/2011 | Griffith | |
| 2012/0092031 A1 | 4/2012 | Shi et al. | |
| 2012/0095529 A1 | 4/2012 | Parramon et al. | |
| 2013/0184794 A1 | 7/2013 | Feldman et al. | |
| 2015/0134029 A1 | 5/2015 | Ozawa et al. | |
| 2015/0144183 A1 | 5/2015 | Yang et al. | |
| 2015/0157861 A1 | 6/2015 | Aghassian | |
| 2016/0051825 A1 | 2/2016 | Ter-Petrosyan et al. | |
| 2018/0071520 A1 | 3/2018 | Weerakoon et al. | |

* cited by examiner

Assume 'X' = 72%

High resolution mode (1%):
<Kn1> = 0
<Xn1>=1001000 (72 in binary)
Yn1_72:1 = '1'; Yn1_100:73 = '0'
Cn1_100:1 = Yn1_100:1, so
Cn1_72:1 = '1', Cn1_100:73 = '0'

Medium resolution mode (2%):
<Kn1> = 1
<Xn1>=x100100 (72/2 = 36 in binary)
Yn1_36:1 = '1'; Yn1_100:37 = '0'
Cn1_36:1, Cn1_86:51 = '1'
Cn1_50:37, Cn1_100:87 = '0'

Low resolution mode (4%):
<Kn1> = 2
<Xn1>=xx10010 (72/4 = 18 in binary)
Yn1_18:1 = '1'; Yn1_100:19 = '0'
Cn1_18:1, Cn1_43:26, Cn1_68:51, Cn1_93:76 = '1'
Cn1_25:19, Cn1_50:44, Cn1_75:69, Cn1_100:94 = '0'

'A'=10 mA
Kn2 = Kn3 = '0' (high resolution mode)
<Xp1> = 100%,
<Xn1>, <Xp2>, <Xp3>, and all other <X> percentage busses for E4-E16 and Ec = 0%

|  | <Xn2> | E2 | <Xn3> | E3 |
|---|---|---|---|---|
| t0 | 100 (100%); Cn2_100:1 asserted | -10 mA | 0 (0%); Cn3_100:1 unasserted | 0 mA |
| t1 | 99 (99%); Cn2_99:1 asserted | -9.9 mA | 1 (1%); Cn3_1 asserted | -0.1 mA |
| t2 | 98 (98%); Cn2_98:1 asserted | -9.8 mA | 2 (2%); Cn3_2:1 asserted | -0.2 mA |
| t3 | 97 (97%); Cn2_97:1 asserted | -9.7 mA | 3 (3%); Cn3_3:1 asserted | -0.3 mA |
| t4 | 96 (96%); Cn2_96:1 asserted | -9.6 mA | 4 (4%); Cn3_4:1 asserted | -0.4 mA |
| ... | ... | ... | ... | ... |
| t97 | 3 (3%); Cn2_3:1 asserted | -0.3 mA | 97 (97%); Cn3_97:1 asserted | -9.7 mA |
| t98 | 2 (2%); Cn2_2:1 asserted | -0.2 mA | 98 (98%); Cn3_98:1 asserted | -9.8 mA |
| t99 | 1 (1%); Cn2_1 asserted | -0.1 mA | 99 (99%); Cn3_99:1 asserted | -9.9 mA |
| t100 | 0 (0%); Cn2_100:1 unasserted | 0 mA | 100 (100%); Cn3_100:1 asserted | -10 mA |

*Figure 11B*

'A' = 10 mA
Kn2 = Kn3 = '1' (low resolution mode)
<Xp1> = 100%,
<Xn1>, <Xp2>, <Xp3>, and all other <X> percentage busses for E4-E16 and Ec = 0%

|  | <Xn2> | E2 | <Xn3> | E3 |
|---|---|---|---|---|
| t0 | 25 (100%); Cn2_100:1 asserted | -10 mA | 0 (0%); Cn3_100:1 unasserted | 0 mA |
| t1 | 24 (96%); Cn2_99:76, 74:51, 49:26, 24:1 asserted | -9.6 mA | 1 (4%); Cn3_76, 51, 26, 1 asserted | -0.4 mA |
| t2 | 23 (92%); Cn2_98:76, 73:51, 48:26, 23:1 asserted | -9.2 mA | 2 (8%): Cn3_77:76, 52:51, 27-26, 2:1 asserted | -0.8 mA |
| t3 | 22 (88%); Cn2_97:76, 72:51, 47:26, 22:1 asserted | -8.8 mA | 3 (12%): Cn3_78:76, 53:51, 28-26, 3:1 asserted | -1.2 mA |
| t4 | 21 (84%); Cn2_96:76, 71:51, 46:26, 21:1 asserted | -8.4 mA | 4 (16%): Cn3_79:76, 54:51, 29-26, 4:1 asserted | -1.6 mA |
| ... | ... | ... | ... | ... |
| t22 | 3 (12%;) Cn2_78:76, 53:51, 28-26, 3:1 asserted | -1.2 mA | 22 (88%): Cn3_97:76, 72:51, 47:26, 22:1 asserted | -8.8 mA |
| t23 | 2 (8%); Cn2_77:76, 52:51, 27-26, 2:1 asserted | -0.8 mA | 23 (92%); Cn3_98:76, 73:51, 48:26, 23:1 asserted | -9.2 mA |
| t24 | 1 (4%); Cn2_76, 51, 26, 1 asserted | -0.4 mA | 24 (96%); Cn3_99:76, 74:51, 49:26, 24:1 asserted | -9.6 mA |
| t25 | 0 (0%); Cn2_100:1 unasserted | 0 mA | 25 (100%); Cn3_100:1 asssserted | -10 mA |

*Figure 11C*

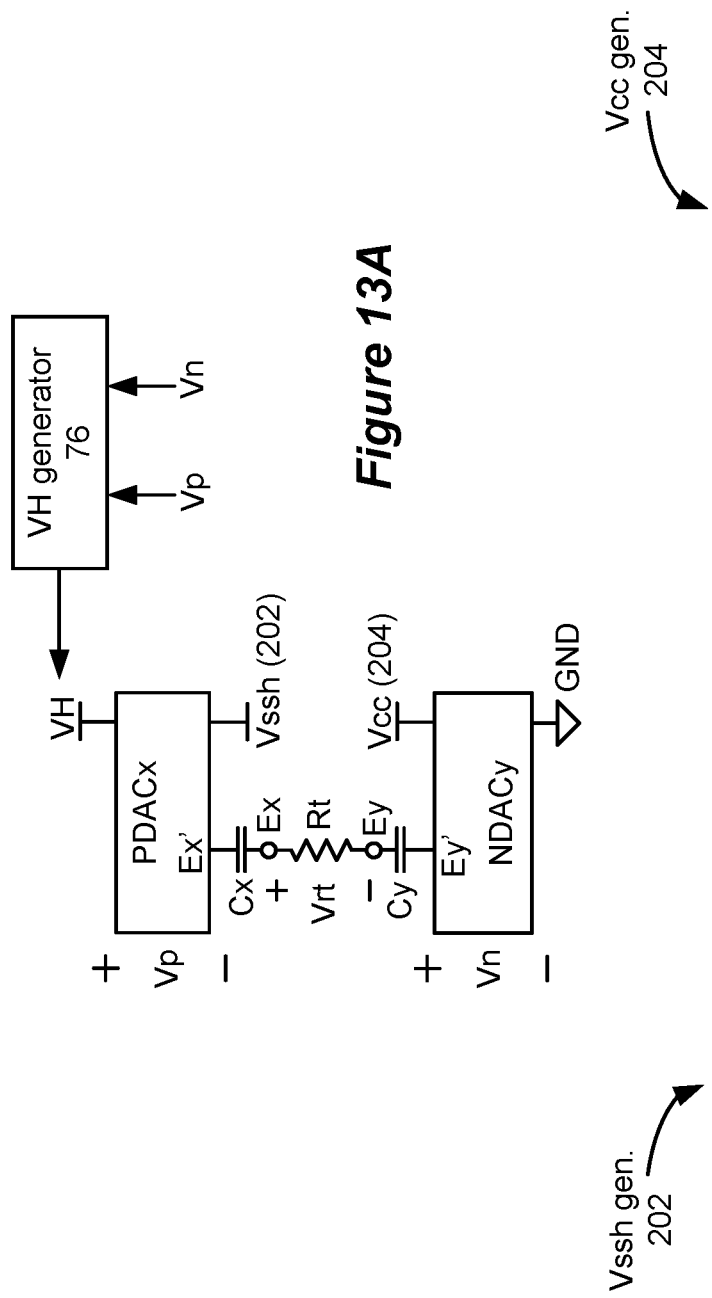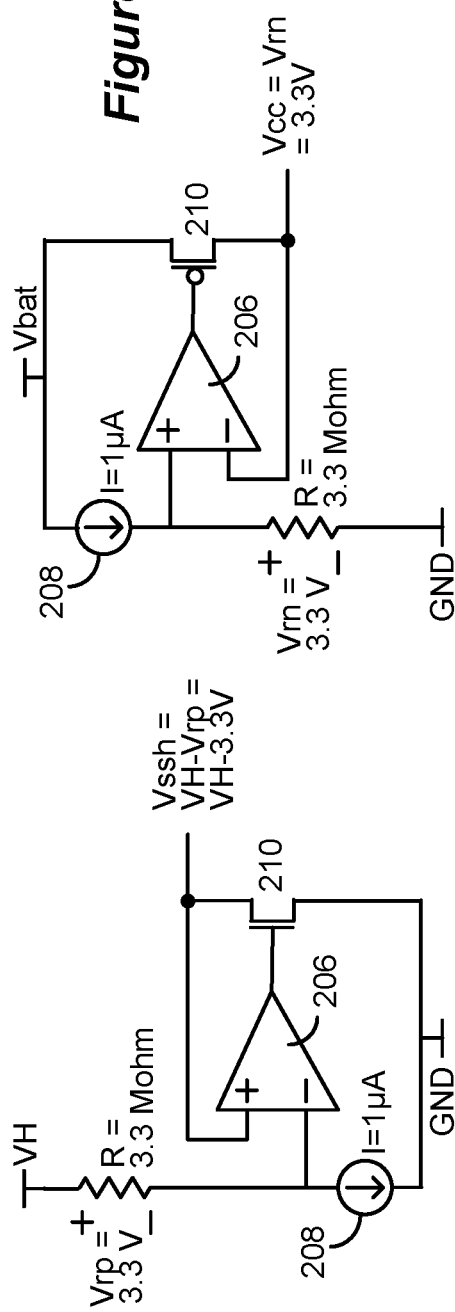
Figure 13A
Figure 13B

CURRENT GENERATION ARCHITECTURE FOR AN IMPLANTABLE STIMULATOR DEVICE TO PROMOTE CURRENT STEERING BETWEEN ELECTRODES

CROSS REFERENCE TO RELATED APPLICATIONS

This is a continuation of U.S. patent application Ser. No. 16/131,809, filed Sep. 14, 2018 (now U.S. Pat. No. 10,912, 942), which is a non-provisional application that claims priority to U.S. Provisional Patent Application Ser. No. 62/559,247, filed Sep. 15, 2017, and Netherlands Patent Application Serial No. N2019707, filed Oct. 11, 2017. These applications are incorporated by reference in their entireties, and priority is claimed to each.

FIELD OF THE INVENTION

The present invention relates generally to medical devices, and more particularly to improved current generation architectures for an implantable pulse generator.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10, which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ei) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two coils (more generally, antennas) are shown in the IPG 10: a telemetry coil 34 used to transmit/receive data to/from an external controller such as a clinician programmer or a hand-held patient programmer used to program stimulation in the IPG (not shown); and a charging coil 36 for charging or recharging the IPG's battery 14 using an external charger (not shown). FIG. 1B shows these aspects in perspective with the case 12 removed for easier viewing. Telemetry coil 34 may alternatively comprise a short range RF antenna for wirelessly communicating in accordance with a short-range RF standard such as Bluetooth, WiFi, MICS, Zigbee, etc., as described in U.S. Patent Application Publication 2016/0051825.

FIG. 2A shows a prior art architecture 40 for the circuitry in IPG 10, which is disclosed in U.S. Patent Application Publications 2012/0095529, 2012/0092031 and 2012/0095519 ("ASIC Publications"). Architecture 40 includes a microcontroller integrated circuit 50 and an Application Specific Integrated Circuit (ASIC) 60 in communication with each other by a bus 90. Stated simply, the microcontroller 50 provides master control for the architecture 40, while ASIC 60 takes commands from and provides data to the microcontroller. ASIC 60 provides specific IPG functionality. For example, and as explained in further detail below, ASIC 60 sends stimulation current to and reads measurements from the sixteen electrodes 16. ASIC 60 comprises a mixed mode IC carrying and processing both analog and digital signals, whereas microcontroller 50 comprises a digital IC carrying and processing only digital signals.

Microcontroller 50 and ASIC 60 comprise monolithic integrated circuits each formed on their own semiconductive substrates ("chips"), and each may be contained in its own package and mounted to the IPG 10's PCB 30. Architecture 40 may also include additional memory (not shown) for storage of programs or data beyond that provided internally in the microcontroller 50. Additional memory may be connected to the microcontroller 50 by a serial interface (SI) as shown, but could also communicate with the microcontroller 50 via bus 90. Bus 90 may comprise a parallel address/data bus, and may include a clock signal and various control signals to dictate reading and writing to various memory locations, as explained in the above-referenced '529 Publication. Bus 90 and the signals it carries may also take different forms; for example, bus 90 may include separate address and data lines, may be serial in nature, etc.

As explained in the above-referenced ASIC Publications, architecture 40 is expandable to support use of a greater number of electrodes 16 in the IPG 10. For example, and as shown in dotted lines in FIG. 2A, architecture 40 may include another ASIC 60' identical in construction to ASIC 60, thus expanding the number of electrodes supported by the IPG 10 from sixteen to thirty two. Various off-bus connections 54 (i.e., connections not comprising part of bus 90) can facilitate such expansion, and may further (e.g., by bond programming; see inputs MIS) designate ASIC 60 as a master and ASIC 60' as a slave. Such differentiation between the ASICs 60 and 60' can be useful, as certain redundant functionality in the slave ASIC 60' can be disabled in favor of the master ASIC 60. Off-bus communications 54 can allow the voltage at the electrodes nodes 61a (E1'-E16') of one of the ASICs (60'; OUT1, OUT2) to be sent to the other ASIC (60; IN1, IN2) to be measured. Off-bus connections 54 are further useful in generation and distribution of a clock signal governing communications on the bus 90 as well as in the ASIC(s) 60. As these concepts are discussed in detail in the above-referenced ASIC Publications, they are not elaborated upon here.

FIG. 2B shows various functional circuit blocks within ASIC 60, which are briefly described. ASIC 60 includes an internal bus 92 which can couple to external bus 90 and which may duplicate bus 90's signals. Note that each of the functional blocks includes interface circuitry 88 enabling communication on the internal bus 92 and ultimately external bus 90, as the above-referenced ASIC Publications explain. Interface circuitry 88 includes circuitry to help each block recognize when bus 92 is communicating data with addresses belonging to that block. ASIC 60 contains several terminals 61 (e.g., pins, bond pads, solder bumps, etc.), such as those necessary to connect to the bus 90, the battery 14, the coils 34, 36, external memory (not shown). Terminals 61 include electrode node terminals 61a (E1'-E16') which connect to the electrodes 16 (E1-E16) on the lead(s) 18 by way of DC-blocking capacitors 55. As is known, DC-blocking capacitors 55 are useful to ensure that DC current isn't inadvertently (e.g., in the event of failure of the ASIC 60's circuitry) injected into the patient's tissue, and hence provide safety to the IPG 10. Such DC-blocking capacitors 55 can be located on or in the IPG 10's PCB 30 (FIG. 1C) inside of the IPG's case 12. See U.S. Patent Application Publication 2015/0157861.

Each of the circuit blocks in ASIC 60 performs various functions in IPG 10. Telemetry block 64 couples to the IPG telemetry coil 34, and includes transceiver circuitry for wirelessly communicating with an external controller according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 38, and contains circuitry for rectifying power wirelessly received from an external charger (not shown), and for charging the battery 14 in a controlled fashion.

Analog-to-Digital (A/D) block 66 digitizes various analog signals for interpretation by the IPG 10, such as the battery voltage Vbat or voltages appearing at the electrodes, and is coupled to an analog bus 67 containing such voltages. A/D block 66 may further receive signals from sample and hold block 68, which as the ASIC Publications explain can be used to measure such voltages, or differences between two voltages. For example, sample and hold circuitry 68 may receive voltages from two electrodes and provide a difference between them (see, e.g., VE1-VE2 in FIG. 3, discussed subsequently), which difference voltage may then be digitized at A/D block 66. Knowing the difference in voltage between two electrodes when they pass a constant current allows for a determination of the (tissue) resistance between them, which is useful for a variety of reasons.

Sample and hold block 68 may also be used to determine one or more voltage drops across the DAC circuitry 72 (see Vp and Vn in FIG. 3, explained subsequently) used to create the stimulation pulses. This is useful to setting the compliance voltage VH output by a compliance voltage generator block 76. Compliance voltage VH powers the DAC circuitry 72, and the measured voltage drops can be used to ensure that the compliance voltage VH produced is optimal for the stimulation current to be provided—i.e., VH is not too low to be unable to produce the current required for the stimulation, nor too high so as to waste power in the IPG 10. Measuring Vp and Vn to determine whether VH is too high or too low is particularly useful because the resistance Rt of the patient's tissue may not be known in advance, or may change over time. Thus, the voltage drop across the tissue, Vrt, may change as well, and monitoring Vp and Vn provides an indication of such changes, and hence whether VH should be adjusted. Compliance voltage generator block 76 includes circuitry for boosting a power supply voltage such as the battery voltage, Vbat, to a proper level for VH.

Such circuitry (some of which may be located off chip) can include an inductor-based boost converter or a capacitor-based charge pump, which are described in detail in U.S. Patent Application Publication 2010/0211132.

Clock generation block 74 can be used to generate a clock for the ASIC 60 and for communication on the bus 92. Clock generation block 74 may receive an oscillating signal from an off-chip crystal oscillator 56, or may comprise other forms of clock circuitry located completely on chip, such as a ring oscillator. U.S. Patent Application Publication 2014/0266375 discloses another on-chip circuit that can be used to generate a clock signal on the ASIC 60.

Master/slave control block 86 can be used to inform the ASIC 60 whether it is to be used as a master ASIC or as a slave ASIC (e.g., 60'), which may be bond programmed at MIS terminal 61. For example, MIS terminal may be connected to a power supply voltage (e.g., Vbat) to inform ASIC 60 that it will operate as a master ASIC, or to ground to inform that it will operate as a slave, in which case certain function blacks will be disabled, as the ASIC Publications explain.

Interrupt controller block 80 receives various interrupts (e.g., INT1-INT4) from other circuit blocks, which because of their immediate importance are received independent of the bus 92 and its communication protocol. Interrupts may also be sent to the microcontroller 50 via the bus 90. Internal controller 82 in the ASIC 60 may receive indication of such interrupts, and act a controller for all other circuit blocks, to the extent microcontroller 50 (FIG. 2A) does not handle such interrupts through the external bus 90. Further, each of the functional circuit blocks contain set-up and status registers (not shown) written to by the controller 82 upon initialization to configure and enable each block. Each functional block can then write pertinent data at its status registers, which can in turn be read by the controller 82 via internal bus 92 as necessary, or by the microcontroller 50 via external bus 90. The functional circuit blocks can further include simple state machines to manage their operation, which state machines are enabled and modified via each block's set-up and status registers.

Nonvolatile memory (NOVO) block 78 caches any relevant data in the system (such as log data). Additional memory (not shown) can also be provided off-chip via a serial interface block 84.

ASIC 60 further includes a stimulation circuit block 70, which includes circuitry for receiving and storing stimulation parameters from the microcontroller 50 via buses 90 and 92. Stimulation parameters define the shape and timing of stimulation pulses to be formed at the electrodes, and can include parameters such as which electrodes E1-E16 will be active; whether those active electrodes are to act as anodes that source current to a patient's tissue, or cathodes that sink current from the tissue; and the amplitude (A), duration (D), and frequency (f) of the pulses. Amplitude may comprise a voltage or current amplitude. Such stimulation parameters may be stored in registers in the stimulation circuitry block 70. See, e.g., U.S. Patent Application Publications 2013/0289661; 2013/0184794.

Block 70 also includes a Digital-to-Analog Converter circuitry (DAC) 72 for receiving the stimulation parameters from the registers and for forming the prescribed pulses at the selected electrodes. FIG. 3 shows a simple example of DAC circuitry 72 as used to provide a current pulse between selected electrodes E1 and E2 and through a patient's tissue, Rt. DAC circuitry 72 as shown comprises two portions, denoted as PDAC 72p and NDAC 72n. These portions of DAC circuitry 72 are so named because of the polarity of the transistors used to build them and the polarity of the current they provide. Thus, PDAC 72p is formed from P-channel transistors and is used to source a current +I to the patient's tissue Rt via a selected electrode E1 operating as an anode. NDAC 72n is formed of N-channel transistors and is used to sink current −I from the patient's tissue via a selected electrode E2. It is important that current sourced to the tissue at any given time equal that sunk from the tissue to prevent charge from building in the tissue, although more than one anode electrode and more than one cathode electrode may be operable at a given time.

PDAC 72p and NDAC 72n receive digital control signals from the registers in the stimulation circuitry block 70, denoted <Pstim> and <Nstim> respectively, to generate the prescribed pulses with the prescribed timing. In the example shown, PDAC 72p and NDAC 72n comprise current sources, and in particular include current-mirrored transistors for mirroring a reference current Iref to produce pulses with an amplitude (A) of I. PDAC 72p and NDAC 72n could however also comprise constant voltage sources. Control signals <Pstim> and <Nstim> also prescribe the timing of the pulses, including their duration (D) and frequency (f), as shown in the waveforms generated at the selected electrodes. The PDAC 72p and NDAC 72n along with the intervening tissue Rt complete a circuit between a power supply VH— the compliance voltage as already introduced—and ground. As noted earlier, the compliance voltage VH is adjustable to an optimal level at compliance voltage generator block 76 (FIG. 2B) to ensure that current pulses of a prescribed amplitude can be produced without unnecessarily wasting IPG power.

The DAC circuitry 72 (PDAC 72p and NDAC 72n) may be dedicated at each of the electrodes, and thus may be activated only when its associated electrode is selected as an anode or cathode. See, e.g., U.S. Pat. No. 6,181,969. Alternatively, one or more DACs (or one or more current sources within a DAC) may be distributed to a selected electrode by a switch matrix (not shown), in which case optional control signals <Psel> and <Nsel> would be used to control the switch matrix and establish the connection between the selected electrode and the PDAC 72p or NDAC 72n. See, e.g., U.S. Pat. No. 8,606,362. DAC circuitry 72 may also use a combination of these dedicated and distributed approaches. See, e.g., U.S. Pat. No. 8,620,436.

In the example waveform shown, the pulses provided at the electrodes are biphasic, meaning that each pulse comprises a first phase 94a of a first polarity, followed by a second phase 94b of an opposite polarity. This is useful as a means of active recovery of charge that may build up on the DC-blocking capacitors 55. Thus, while charge will build up on the capacitors 55 during the first pulse phase 94a, the second pulse phase 94b will actively recover that charge, particularly if the total amount of charge is equal in each phase (i.e., of the area under the first and second pulse phases are equal). Recovery of excess charge on the DC-blocking capacitors 55 is important to ensure that the DAC circuit 72 will operate as intended: if the charge/voltage across the DC-blocking capacitors 55 is not zero at the end of each pulse, it will skew formation of subsequent pulses, which may therefore not provide the prescribed amplitude.

While active recovery of charge using a biphasic pulse is beneficial, such active recovery may not be perfect, and hence some residual charge may remain on the DC-blocking capacitors 55 even after the second phase 94b of the biphasic pulse. Thus, the art has recognized the utility of passive charge recovery. Passive charge recovery is implemented with the stimulation circuit block 70, and includes use of passive recovery switches (transistors) 96, which are connected between the electrode nodes (E1'-E16') 61a and a common reference voltage. This voltage as shown may simply comprise the battery voltage, Vbat, but another reference voltage could also be used. Closing the passive recovery switches 96 during a time period 98 after the second pulse phase 94b couples the DC-blocking capacitors 55 in parallel between the reference voltage and the patient's tissue. Given the previous serial connection of the DC-blocking capacitors, this should normalize any remaining charge.

BRIEF DESCRIPTION OF THE DRAWINGS

FIGS. 7A and 7B respectively show the master DAC and distributor that provides the amplitude-scaled reference current to the PDACs and NDACs, while

FIG. 13A shows the high power domain (VH/Vssh) operable in the PDACs and the low power domain (Vcc/ground) operable in the NDACs, and shows how compliance voltage VH can be varied.

FIG. 13B shows generators used to produce Vssh and Vcc.

DETAILED DESCRIPTION

Figure 4A:
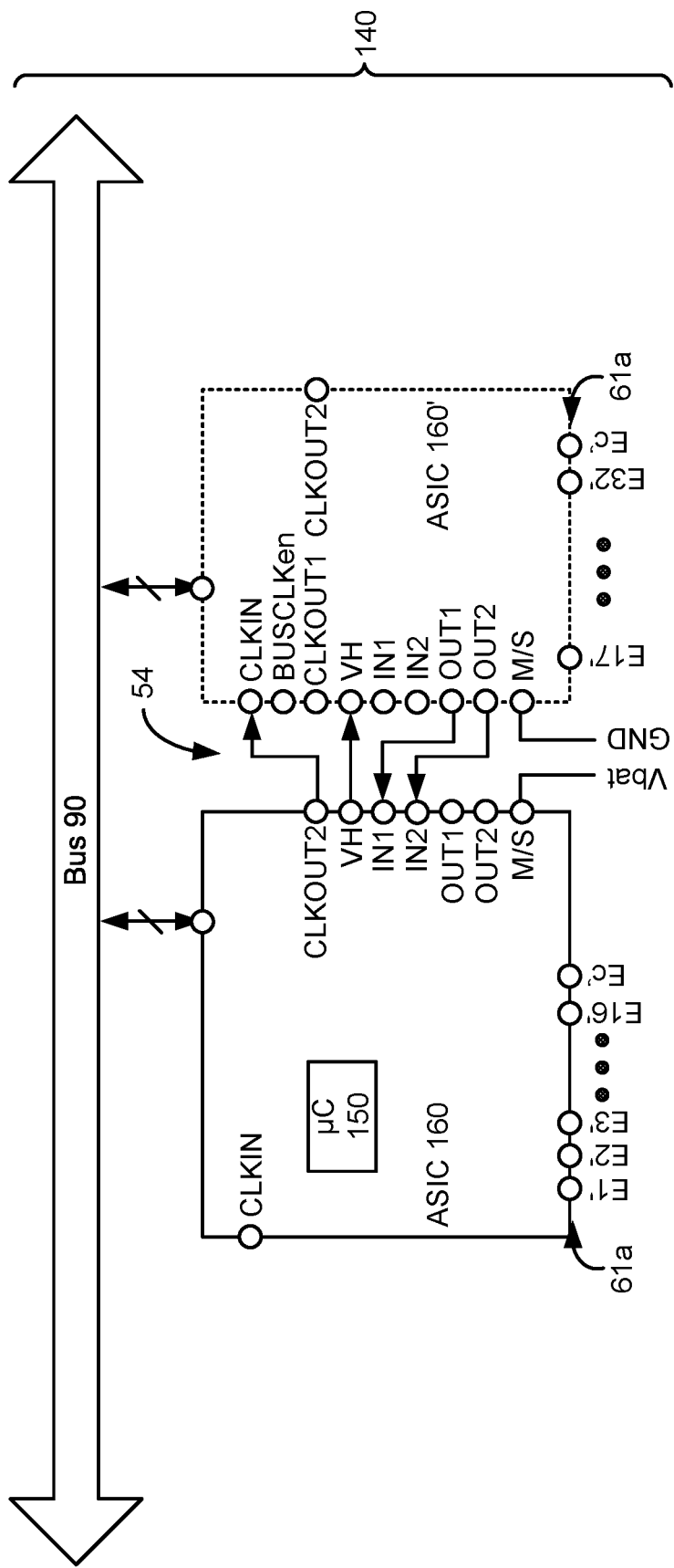
FIG. 4A shows an improved architecture for an IPG, in which an improved ASIC includes a microcontroller circuit block.
Figure 4B:
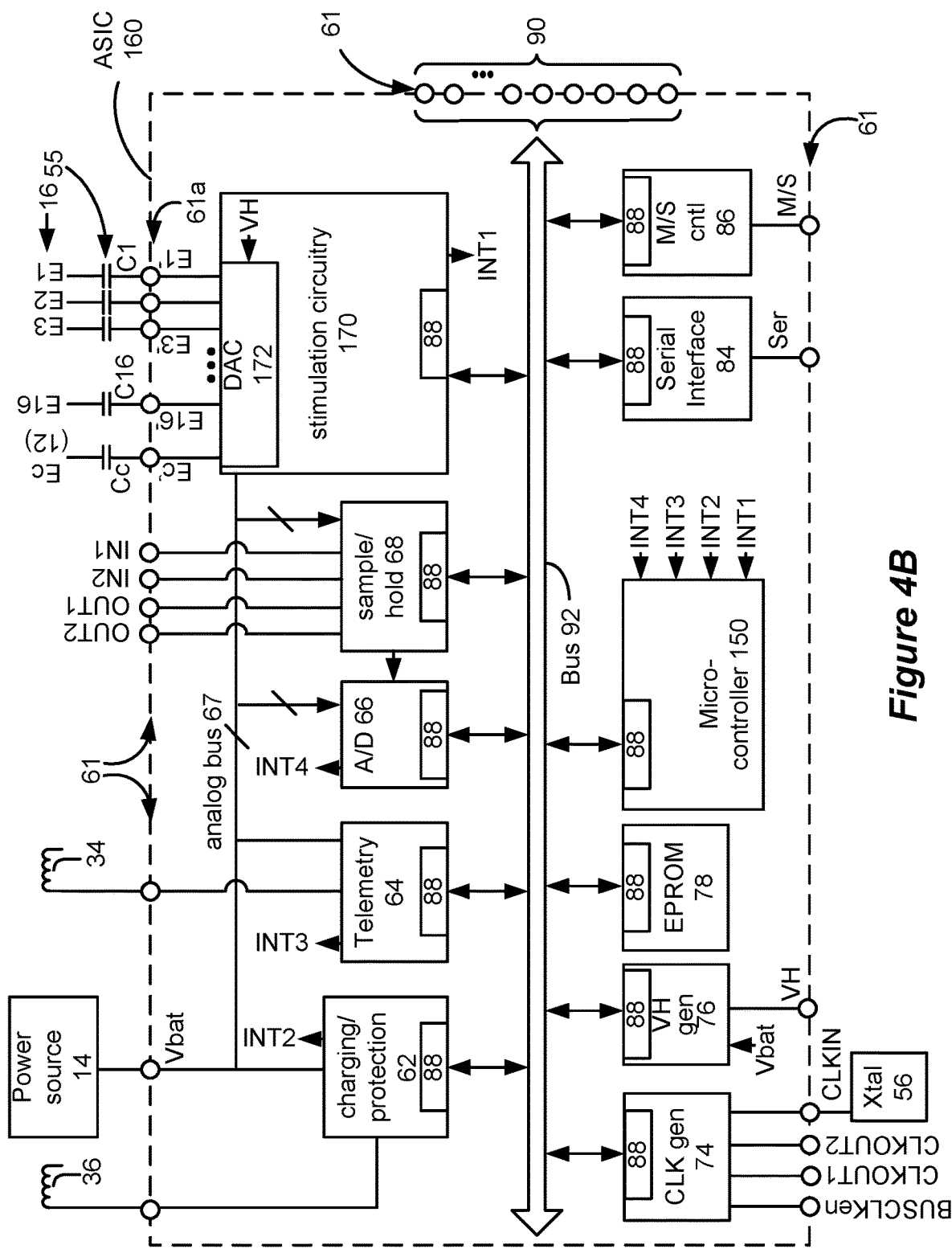
FIG. 4B shows circuitry blocks within the improved ASIC, including improved stimulation circuitry and its improved DAC circuitry.

FIGS. 4A and 4B show an improved architecture 140 and ASIC 160 for an IPG such as IPG 10 described earlier. Elements in architecture 140 and ASIC 160 that can remain unchanged from the prior art architecture 40 and ASIC 60 described in the Introduction bear the same elements numerals, and are not described again.

Figure 1A:
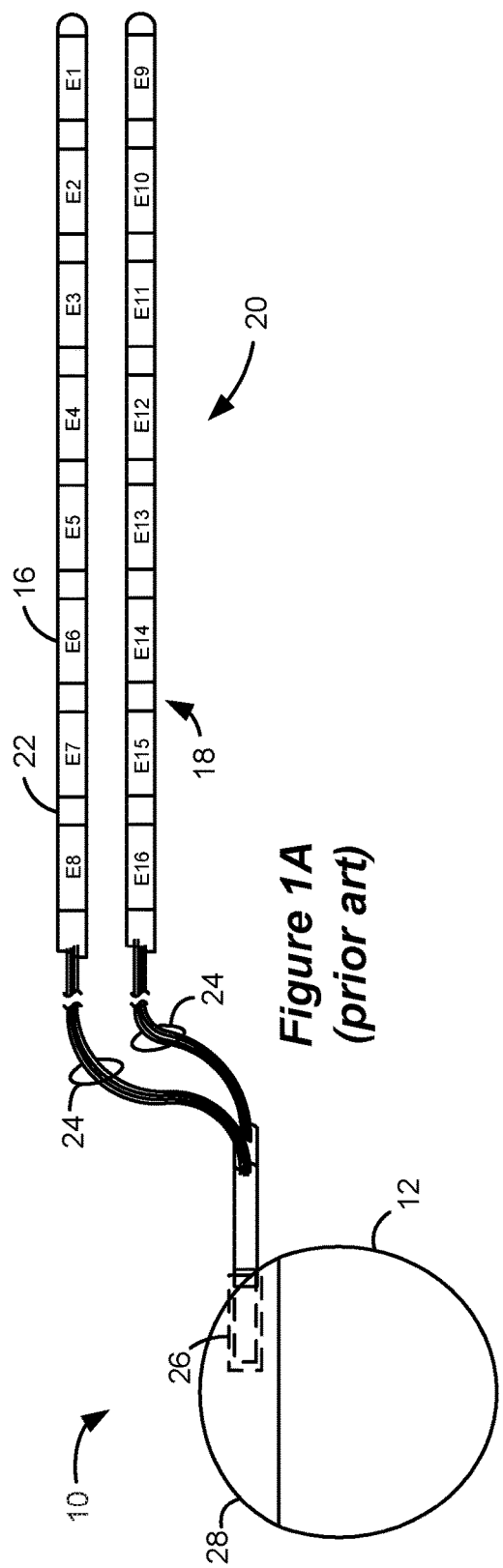
FIGS. 1A-1C show an Implantable Pulse Generator (IPG), and the manner in which an electrode array is coupled to the IPG, in accordance with the prior art.
Figure 1C:
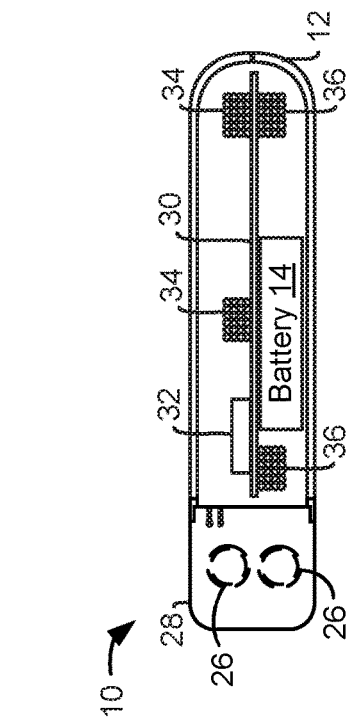
Figure 1B:
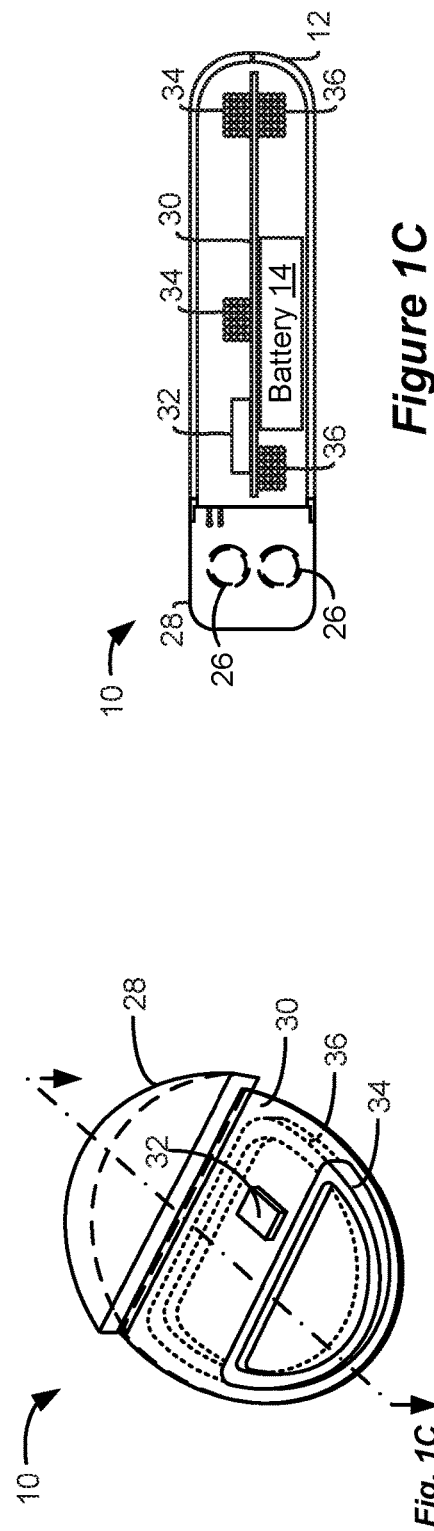
Figure 2A:
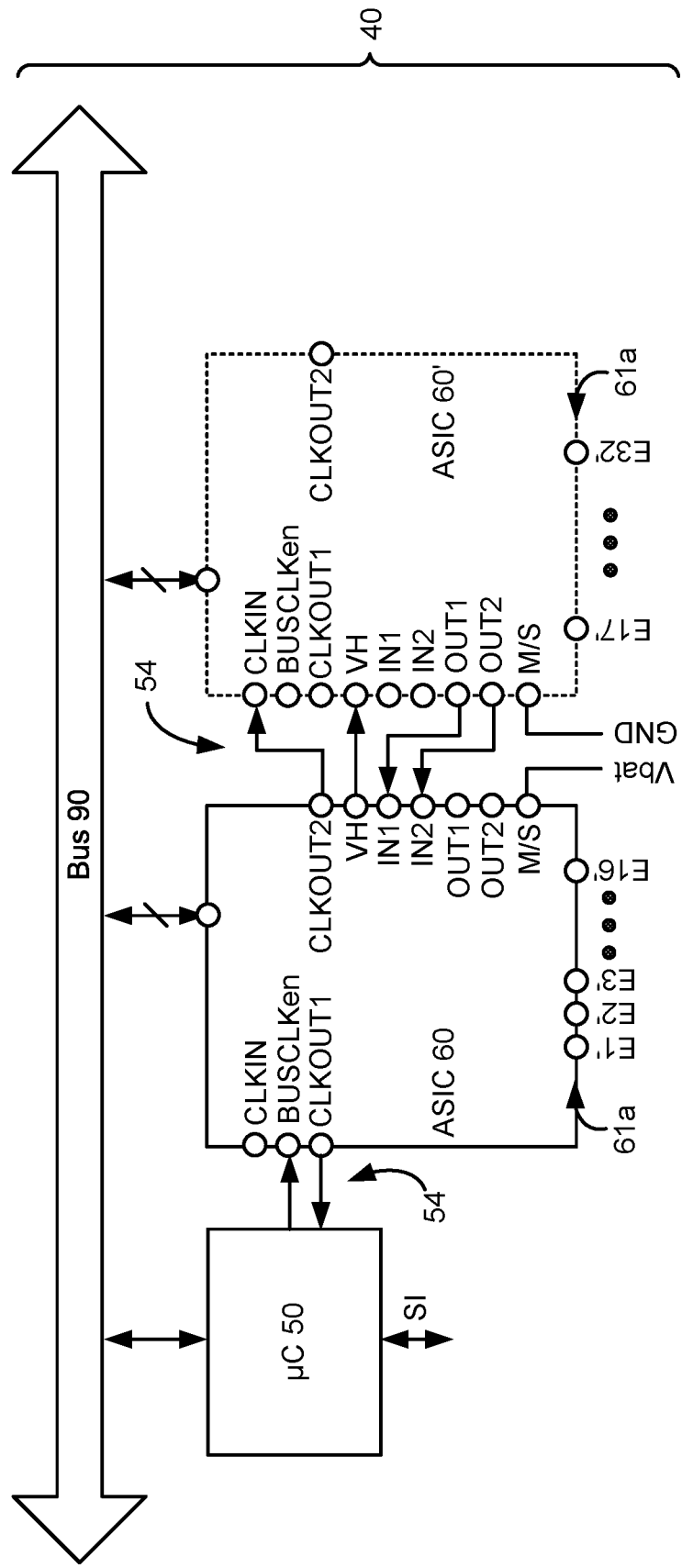
FIG. 2A shows an architecture for an IPG utilizing a microcontroller integrated circuit and an Application Specific Integrated Circuit (ASIC), in accordance with the prior art.
Figure 2B:
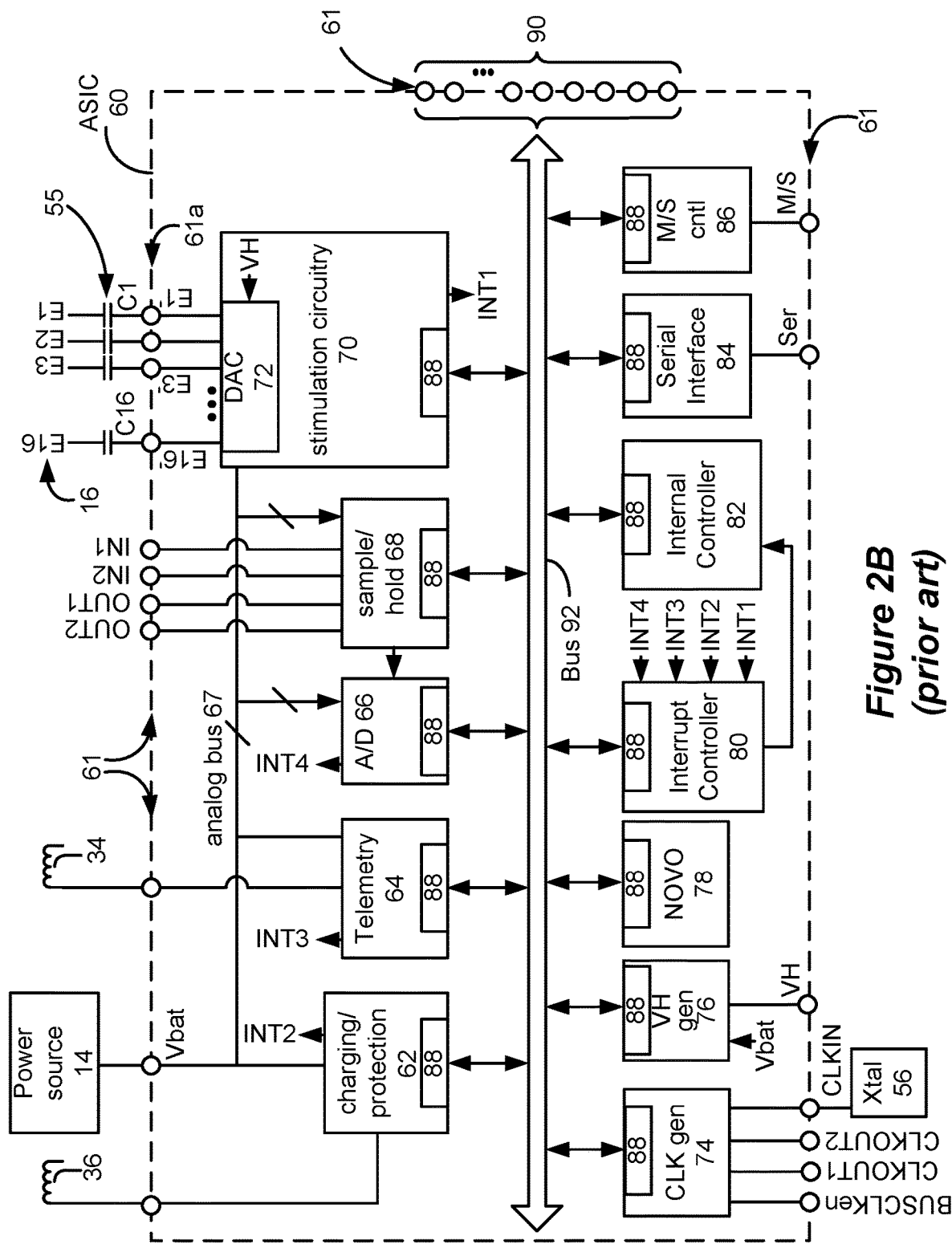
FIG. 2B shows circuitry blocks within the ASIC, and connection to off-chip components, in accordance with the prior art.

Improved ASIC 160 includes a microcontroller block 150 as part of its monolithic structure, which as shown in FIG. 4B can communicate with other functional blocks in the ASIC 160 via internal bus 92. Because ASIC 160 includes an internal microcontroller 150, an external microcontroller (e.g., 50, FIG. 2A) can be dispensed with in the improved architecture 140, simplifying IPG design and saving room within the interior of the case 12 and on the IPG's PCB 30 (FIG. 1C).

Microcontroller block 150 may receive interrupts independent of the bus 92 and its communication protocol, although interrupts may also be sent to the microcontroller 150 via the bus 92 as well. Even though ASIC 160 includes a microcontroller block 150, the ASIC 160 may still couple to an external bus 90, as shown in FIG. 4A. This can facilitate communications between the ASIC 160 and another device, such as a memory integrated circuit (not shown) or possibly another microcontroller device that might be coupled to the bus 90. Bus 90 can also facilitate communication between (master) ASIC 160 and another identically-constructed (slave) ASIC 160', shown in dotted lines in FIG. 4A. As described in the Introduction (FIG. 2A), use of an additional ASIC 160' allows the number of electrodes 16 the IPG 10 supports to be doubled, and many of the same off-bus connections 54 can be used as described earlier, and as described in the above-referenced ASIC Publications. In one example, the microcontroller block 150 can comprise circuitry from an ARM Cortex-M0+ Processor, which may be incorporated into the monolithic integrated circuit of the ASIC 160 by licensing various necessary circuits from the library that comprises that processor.

Figure 3:
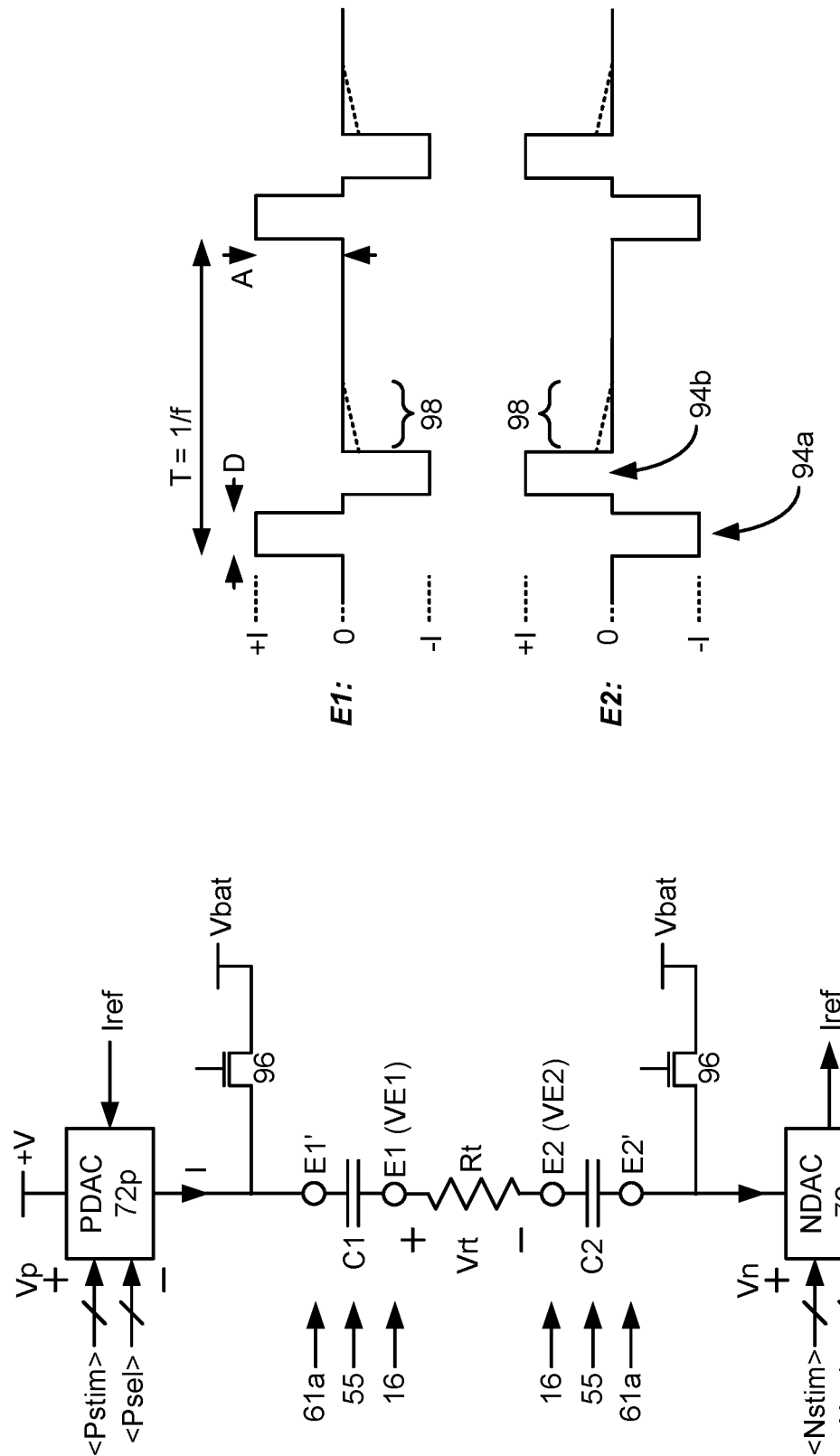
FIG. 3 shows aspects of the Digital-to-Analog converter (DAC) circuitry within the stimulation circuitry of the ASIC, and stimulation pulses formable thereby, in accordance with the prior art.
Figure 5:
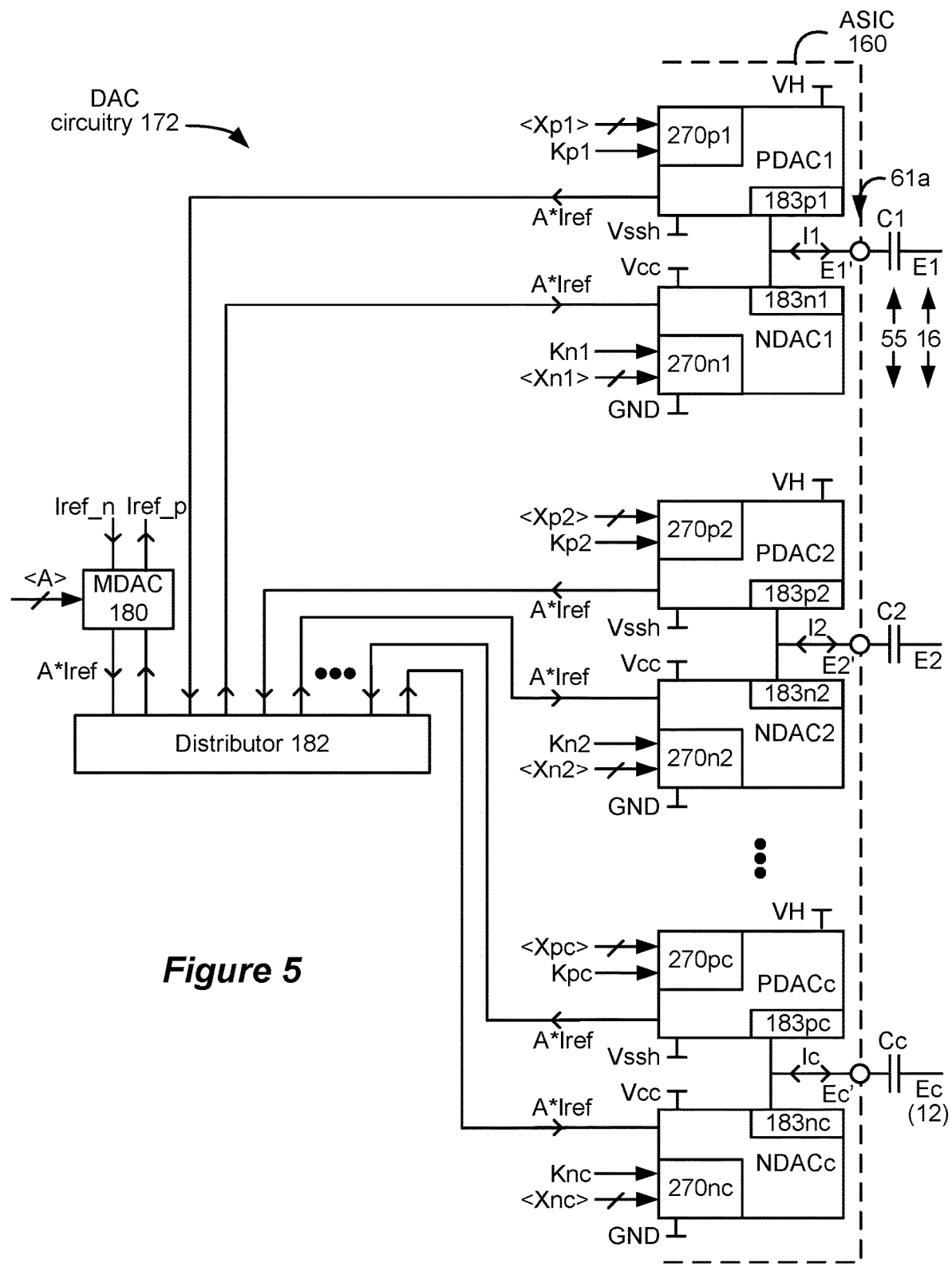
FIG. 5 shows the improved DAC circuitry, including a centralized master DAC to set the amplitude of stimulation via an amplitude bus, and a distributor for sending a reference current scaled by the amplitude to PDAC/NDAC pairs dedicated to each electrode.

FIGS. 5-11C describe details of improved stimulation circuitry 170, including improved DAC circuitry 172, within ASIC 160. FIG. 5 shows a first example of DAC circuitry 172, in which each electrode node 61a (Ei) has its own dedicated PDAC (PDACi) able when selected to source a current to that electrode node, and its own dedicated NDAC (NDACi) able to sink a current from that electrode node. In the example of FIG. 5 it is assumed that ASIC 160 supports seventeen electrodes 16, specifically electrodes E1-E16 plus a case electrode Ec comprising the IPG's conductive case 12 (FIG. 1A), which is useful to use as an electrode during monopolar stimulation. Thus, there are seventeen PDACs and seventeen NDACs. However, the number of supported electrodes can vary. Each PDACi/NDACi pair outputs its current from output stages 183pi and 183ni respectively, the outputs of which are connected together at each electrode node Ei' (61a) to form a current Ii, which will source a current when the PDACi is active and sink a current when the NDACi is active. Output stages 183 in each PDAC and NDAC can be considered part of those PDACs and NDACs. Each electrode node Ei' is then preferably connected off chip to a DC-blocking capacitor Ci (55), which are then in turn connected to the lead-based electrodes Ei (16), as explained earlier. DAC circuitry 172 can further include passive recovery switches connected to each electrode node Ei' (96, FIG. 3), as is explained in further detail in U.S. Patent Application Publication 2018/0071527, which is incorporated by reference in its entirety.

As explained further with reference to FIGS. 13A-14D, each of the PDACs, and the control signals they receive and process, operate in a high power domain defined by power supply voltages VH and Vssh. VH comprises the compliance voltage described earlier and acts as the upper power supply within the high power domain, while Vssh is lower than VH and acts as the lower power supply within the high power domain. By contrast, each of the NDACs, and the control signals they receive and process, operate in a low power domain defined by power supply voltages Vcc and ground (GND; 0 Volts). Vcc acts as the upper power supply within the low power domain, while GND is lower than Vcc and acts as the lower power supply within the low power domain. Both of power supplies VH and Vssh are preferably variable as explained later, but are preferably higher than power supplies Vcc and ground.

DAC circuitry 172 includes a master DAC (MDAC) 180 which communicates with all PDAC/NDAC pairs at each of the electrodes. Master DAC 180 receives an indication of the total anodic and total cathodic current amplitude 'A' of the stimulation pulses that the IPG will form at any given time, which indication is denoted by a bus of digital signals, <A>. The total anodic current sourced to the tissue should equal the total cathodic current sunk from the tissue at any point in time; otherwise an undesirable net charge would build in the patient's tissue. Thus, 'A' is the same for both total anodic current and total cathodic current.

Figure 6:
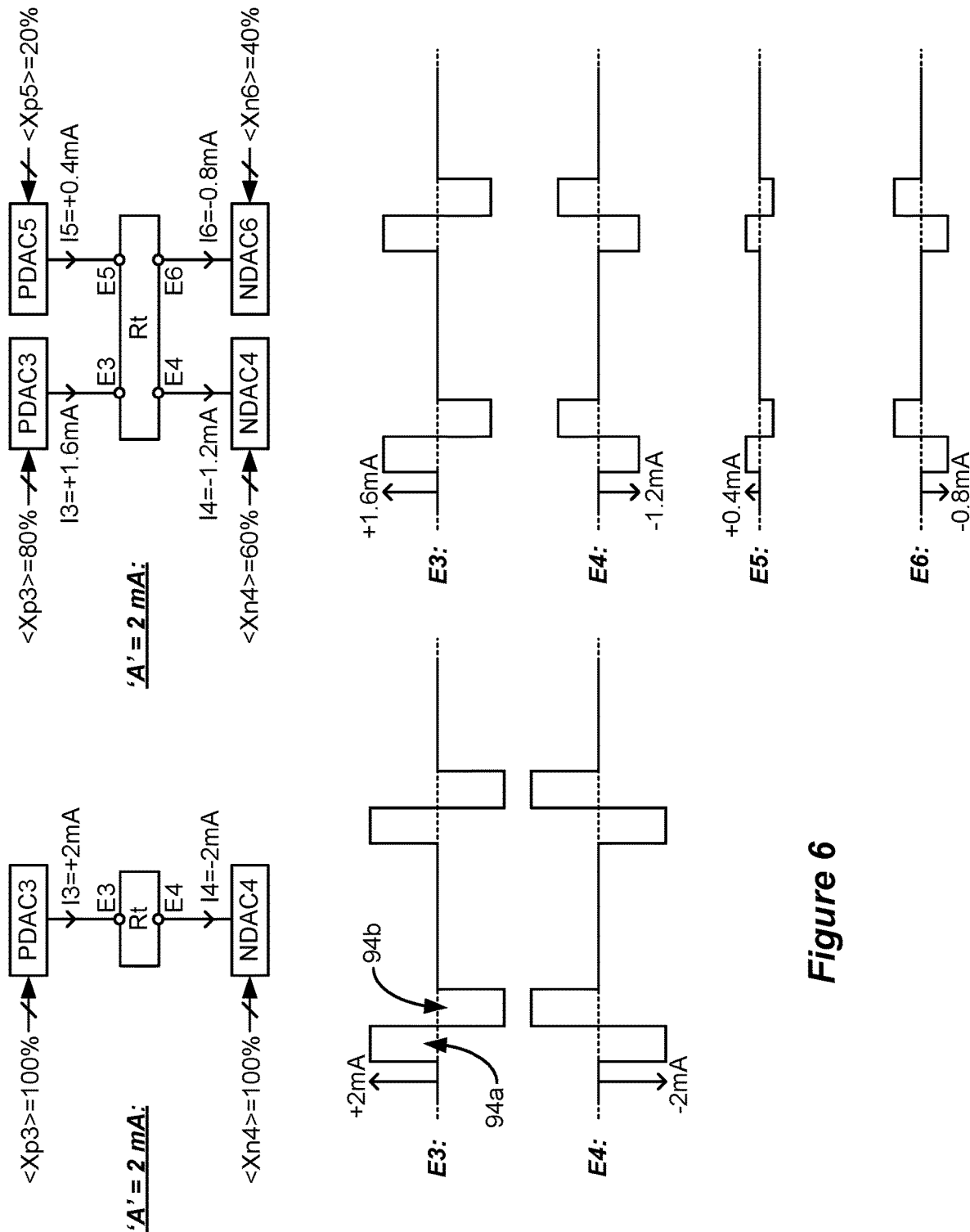
FIG. 6 shows the manner in which stimulation pulses can be formed at the electrodes based on the amplitude and based on percentage busses received by the PDACs and NDACs.

Total anodic and cathodic current 'A' is illustrated by the example pulses in FIG. 6. Two sets of pulses are illustrated, and in each case, 'A' as set by amplitude bus <A> is 2 mA. In the pulses at the left (and considering only the first pulse phases 94a of the biphasic pulses), only one anode electrode E3 has been specified, and only one cathode electrode E4 has been specified. Thus, PDAC3 simply sources +2 mA (the total anodic current) to its dedicated electrode E3 and to the patient's tissue Rt, and NDAC4 simply sinks −2 mA (the total cathodic current) from its dedicated electrode E4 and from the patient's tissue Rt. (During the second pulse phases 94b, this would essentially be reversed by activating the opposite polarity DAC at the selected electrodes, with NDAC3 sinking −2 mA from cathode electrode E3, and PDAC4 sourcing +2 mA to anode electrode E4).

In the pulses at the right of FIG. 6, two electrodes E3 and E5 have been selected as anode electrodes, and two electrodes E4 and E6 have been selected as cathode electrodes.

Therefore, the two anode electrodes share the total anodic current of 'A'=2 mA, with PDAC3 sourcing +1.6 mA to electrode E3 and PDAC5 sourcing +0.4 mA to electrode E5. The two cathode electrodes share the total cathodic current of 'A'=2 mA, with NDAC4 sinking −1.2 mA from electrode E4 and PDAC6 sinking −0.8 mA from electrode E6. How the total anodic current and the total cathodic current 'A' is shared in DAC circuitry 172 between the selected anode and cathode electrodes is explained subsequently.

Returning to FIG. 5, master DAC 180 in this example receives two reference currents, Iref_n and Iref_p of different polarities. This detail is explained later, but Iref_n and Iref_p are of essentially the same small magnitude, e.g., 100 nA, and both may therefore be simply referred to as Iref. The master DAC 180 amplifies the reference current by 'A' as specified by the amplitude bus <A>, and so outputs A*Iref. In the example shown, master DAC 180 outputs A*Iref with different polarities, again as explained later. In one example, <A> can comprise 8 bits, and thus master DAC 180 can output currents in 256 increments of Iref, i.e., 0, Iref, 2Iref, 3Iref, . . . , 255Iref, or 0.0 nA, 100 nA, 200 nA, 300 nA, . . . , 25.5 µA. The number of bits within amplitude bus <A> and hence the corresponding number of increments master DAC 180 can output are variable. A*Iref is further amplified at the PDACs or NDACs before being output to the electrode nodes 61a, as explained subsequently.

Master DAC 180 provides A*Iref to distributor circuitry 182, whose function is to generate and distribute A*Iref to each PDAC and NDAC with the correct polarity. More specifically, and as the arrows in FIG. 5 show, distributor 182 pulls A*Iref from the PDACs and pushes A*Iref to the NDACs.

Figure 7A:
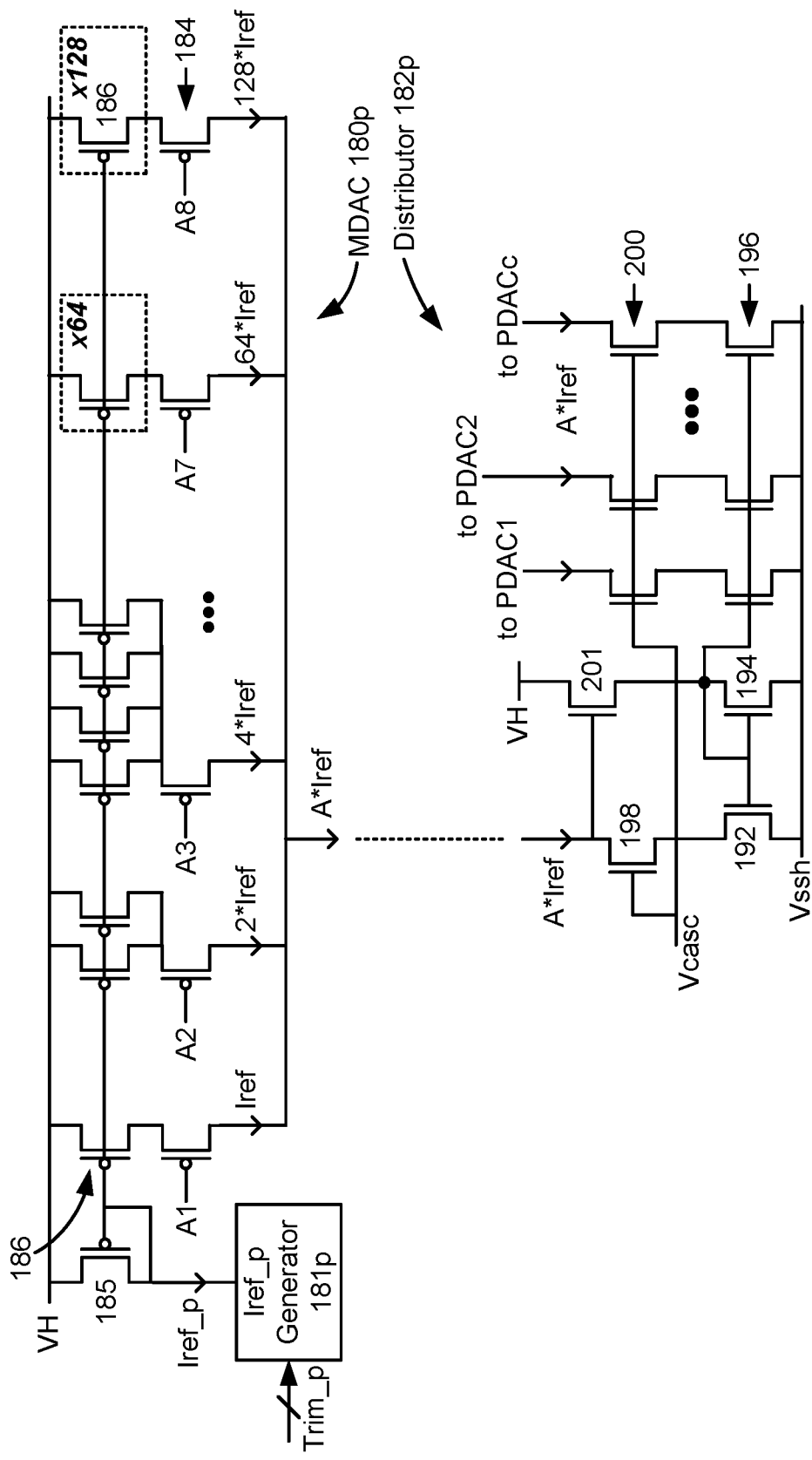
Figure 7B:
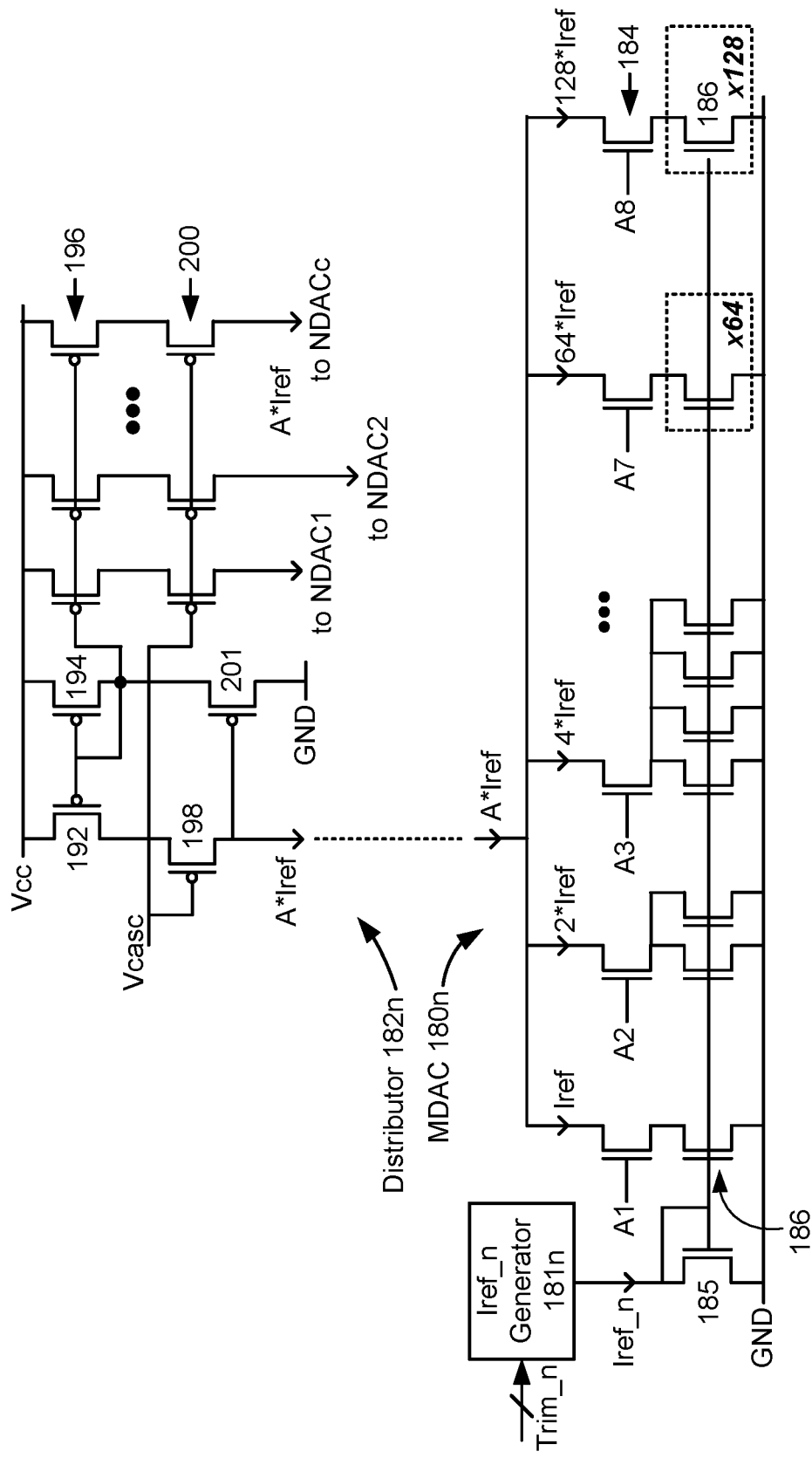

FIGS. 7A and 7B show details of the master DAC 180 and distributor 182. In the illustrated example, the master DAC 180 comprises two sections 180p (FIG. 7A) and 180n (FIG. 7B). The distributor 182 also comprises two sections 182p (FIG. 7A) and 182n (FIG. 7B). Master DAC 180p and distributor 182p work together (FIG. 7A) to pull A*Iref from the PDACs, while master DAC 180n and distributor 182n work together (FIG. 7B) to push A*Iref to the NDACs.

As a comparison of FIGS. 7A and 7B shows, the circuitry 180p/182p and the circuitry of 180n/182n are symmetric, although 180p/182p are powered in the high power domain (VH/Vssh), while 180n/182n are powered in the low power domain (Vcc/GND). Further, the polarity of the transistors in 180p/182p and 180n/182n are different, with P-channel transistors proximate to the higher power supply in each power domain (VH and Vcc), and with N-channel transistors proximate to the lower power supply in each power domain (Vssh and GND). Nonetheless, the combination of 180p/182p in FIG. 7A essentially operates the same as does the combination of 180n/182n in FIG. 7B, except that logic state of control signals (e.g., <A>) would be inverted in each (not shown). Thus, similar elements numerals are provided for the transistors in these figures, and both are discussed for simplicity primarily with reference to FIG. 7B.

FIG. 7B shows master DAC 180n, which is controlled directly by the eight control signals A8:1 in amplitude bus <A>. Each of these control signals is input to a selection transistor 184, each of which is in series with a differing number of transistors 186 connected in parallel. Reference current Iref_n is produced by a generator 181n, and is provided to a transistor 185, which mirrors its current to each of the transistors 186. (Such mirroring occurs because the gates of transistor 185 and transistors 186 are connected to transistor 185's drain, as is well known). The number of paralleled transistors 186 varies in binary fashion, such that A1 controls connection of one transistor 186; A2 controls connection of two transistors 186; A3 controls connection of four transistors 186, and so on, with A8 controlling connection of 128 transistors 186. Because selection transistors 184 are N-channel transistors, they are active high (they would be active low in master DAC 180p in FIG. 7A). Therefore, for example, if the amplitude bus signals <A>='00010101', i.e., the number 21 in binary, control signals A5, A3, and A1 are asserted, and (16+4+1)*Iref will be mirrored and summed at the output of the master DAC 180 for a total current 21Iref. In actually, it is Iref_n that is mirrored, but again this can be referred to as Iref for simplicity.

Master DAC 180n pulls output A*Iref from distributor 182n, which in turn pushes A*Iref out to each NDAC. Specifically, A*Iref is mirrored into a series of branches each comprising a transistor 196 and a transistor 200 in series, with each branch pushing A*Iref to its dedicated NDAC. Distributor 182n is designed to achieve good linearity throughout the entire range with which A*Iref can vary (again, e.g., from 0 to 25.5 µA). Transistor 192 and transistors 196 form current mirrors, and are of the same size. Cascode transistors 198 and 200 are controlled by voltage Vcasc, and transistors 192, 194, 198, and 201 form a feedback loop.

The master DAC 180p of FIG. 7A operates similarly to push A*Iref to its distributor 182p, which in turn operates similarly to pull A*Iref from each of the PDACs. Notice that master DAC 180p includes its own generator 181p to generate its own reference current, Iref_p. Both the Iref_p generator 181p (FIG. 7A) and the Iref_n generator 181n (FIG. 7B) receive control signals Trim_p and Trim_n, which allow the magnitude of Iref_p and Iref_n to be adjusted. As stated earlier, Iref_p and Iref_n are essentially the same magnitude (100 nA). However, it is preferred to have the flexibility to adjust these magnitudes slightly via Trim_p and Trim_n to ensure that the amplified outputs A*Iref of the combinations 180p/182p and 180n/182n are equal; they might not be given non-idealities inherent in ASIC 160 fabrication. While reference current generation could be adjusted at any time, it is preferred to adjust Iref_p and Iref_n during manufacturing. For example, A*Iref can be measured during manufacturing from the master DAC 180p and the master DAC 180n, and Trim_p and Trim_n can be adjusted until the magnitude of A*Iref from each is equal. Thereafter, Trim_p and Trim_n can be stored in a non-volatile registers (not shown) so that generators 181p and 181n can output Iref_p and Iref_n with appropriate magnitudes.

Figure 7C:
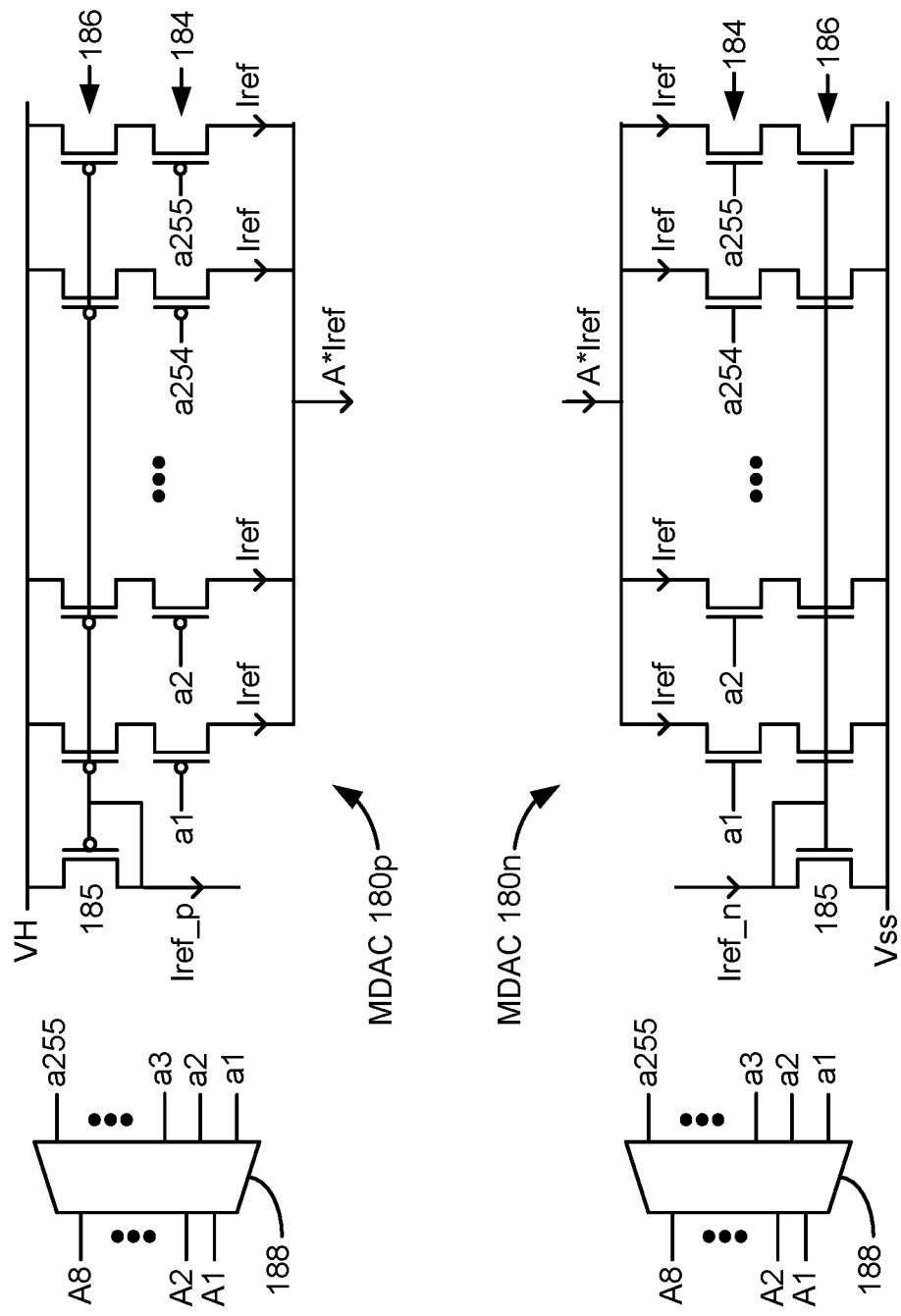
FIG. 7C shows an alternative design for the master DACs.

FIG. 7C shows alternative circuitry for master DACs 180p and 180n. These examples include logic circuitry 188, which convert the eight <A> bits into 256 different control signals a0 to a255. Logic circuitry 188 is sometimes known as a "thermometer decoder," which will assert a number of outputs equal to the input value 'A.' Assuming again that the amplitude bus signals <A>='00010101' (21), control signals a21:1 will be asserted, with all other control signals a255:22 remaining unasserted. Control signals a255:1 are each sent to a selection transistor 184, each of which is in series with only a single current mirror transistor 186. The assertion of each control signal 'a' therefore mirrors and sums an increment of Iref at the output of the master DAC 180p and 180n, and so the assertion of a21:1 again renders 21Iref at the output.

The master DAC 180 and distributor 182 will be located at a discrete location on the ASIC 160. By contrast, each of the PDAC/NDAC pairs will be at different locations on the ASIC 160, such as generally proximate to the ASIC chip's bond pads (61) connected to electrode nodes Ei' 61a. This means the distance between the master DAC 180/distributor 182 and each PDAC/NDAC pair will vary. Nonetheless, because each PDAC and NDAC is current controlled (rather than voltage controlled)—i.e., controlled by A*Iref-such differences in distance are mitigated. Were the PDACs and NDACs voltage controlled, with the master DAC 180 or distributor 182 outputting A*Vref for example, the different distances would work different voltage drops across the conductive traces connecting the distributor 182 to each of the PDACs and NDACs. These differing voltage drops would mean that each PDAC and NDAC would not receive exactly A*Iref, which would affect the accuracy of the amplitudes of the currents output by each PDAC and NDAC. Because the PDACs and NDACs are current controlled by A*Iref, such different transmission distances and voltage drops are of significantly lesser concern. Instead, each PDAC and NDAC will receive exactly A*Iref, allowing the PDACs and NDACs to output currents with proper amplitudes that do not vary as a function of their distance to the master DAC 180/distributor 182. Such current control of the PDACs and NDACs eases layout of the DAC circuitry 172 on the ASIC 160.

Referring again to FIG. 5, percentage busses, <X>, are shown, which are useful to allocating or "steering" of current between the electrodes, as explained further below. Each PDAC and NDAC receives its own percentage bus: thus, PDAC receives <Xp1>, NDAC1 receives <Xn1>, PDAC2 receives <Xp2>, NDAC2 receives <Xn2>, etc. As will be explained further below, the percentage busses <Xpi> specify a percentage (from 0-100%) of the total anodic current 'A' that each PDACi must source to its associated electrode node Ei'. Percentage busses <Xni> specify a percentage of the total cathodic current 'A' that each NDACi must sink from its associated electrode node Ei'. In effect, the various percentage busses <X> explain how the total anodic current and total cathodic current 'A' are shared between electrodes.

This is explained further with reference to the pulses shown in FIG. 6. As described earlier, amplitude 'A' is set by amplitude bus <A> to 2 mA in each example. For the pulses at the left, where electrode E3 is selected as the only anode and electrode E4 as the only cathode, these electrodes will receive 'X'=100% of the total anodic and total cathodic current respectively. Therefore, percentage bus <Xp3> will indicate 100% to PDAC3 associated with electrode E3, and percentage bus <Xn4> will indicate 100% to NDAC4 associated with electrode E3.

For the pulses at the right, having a plurality of anode and cathode electrodes, the percentage busses indicates the percentage of the total anodic or cathodic current 'A'=2 mA that the associated PDAC or NDAC should output. Therefore, to form a pulse with an amplitude of +1.6 mA at anode electrode E3, percentage bus <Xp3> will indicate 80% to PDAC3, which will in turn source a current of 80% of 2.0 mA, or +1.6 mA, at E3. Percentage bus <Xp5> is set to 20%, meaning the remaining anodic current (20% of 2 mA, or +0.4 mA) is sourced from PDAC5 to anode electrode E5. Similarly, to form pulses of −1.2 mA and −0.8 mA at the cathode electrodes E4 and E6, the total cathodic current 'A'=2.0 mA is shared 60% and 40%, and so <Xn4>=60% is sent to NDAC4, and <Xn6>=40% is sent to NDAC6. In effect, percentage bus signals <Xpi> are used to select one or more electrodes as anodes and to specify the percentage relative to 'A' each must source, while percentage bus signals <Xni> are used to select one or more electrodes as cathodes and to specify the percentage relative to 'A' each must sink.

Returning to FIG. 5, resolution control signals, K, are shown. Each PDAC and NDAC preferably receives its own resolution control signal: thus, PDAC1 receives Kp1, NDAC1 receives Kn1, PDAC2 receives Kp2, NDAC2 receives Kn2, etc. As will be explained further below, the resolution control signals specify an amount by which each PDAC or NDAC's percentage (X) can be adjusted. By way of preview, and in just one example, a resolution control signal K will dictate whether the percentage 'X' of its associated PDAC or NDAC (and hence the current it outputs to its electrode node 61a) will be variable in 1% increments in a high resolution mode (i.e., 'X'=1%, 2%, 3%, etc.) or in 4% increments in a low resolution mode (i.e., 'X'=4%, 8%, 12%, etc.).

Figure 8A:
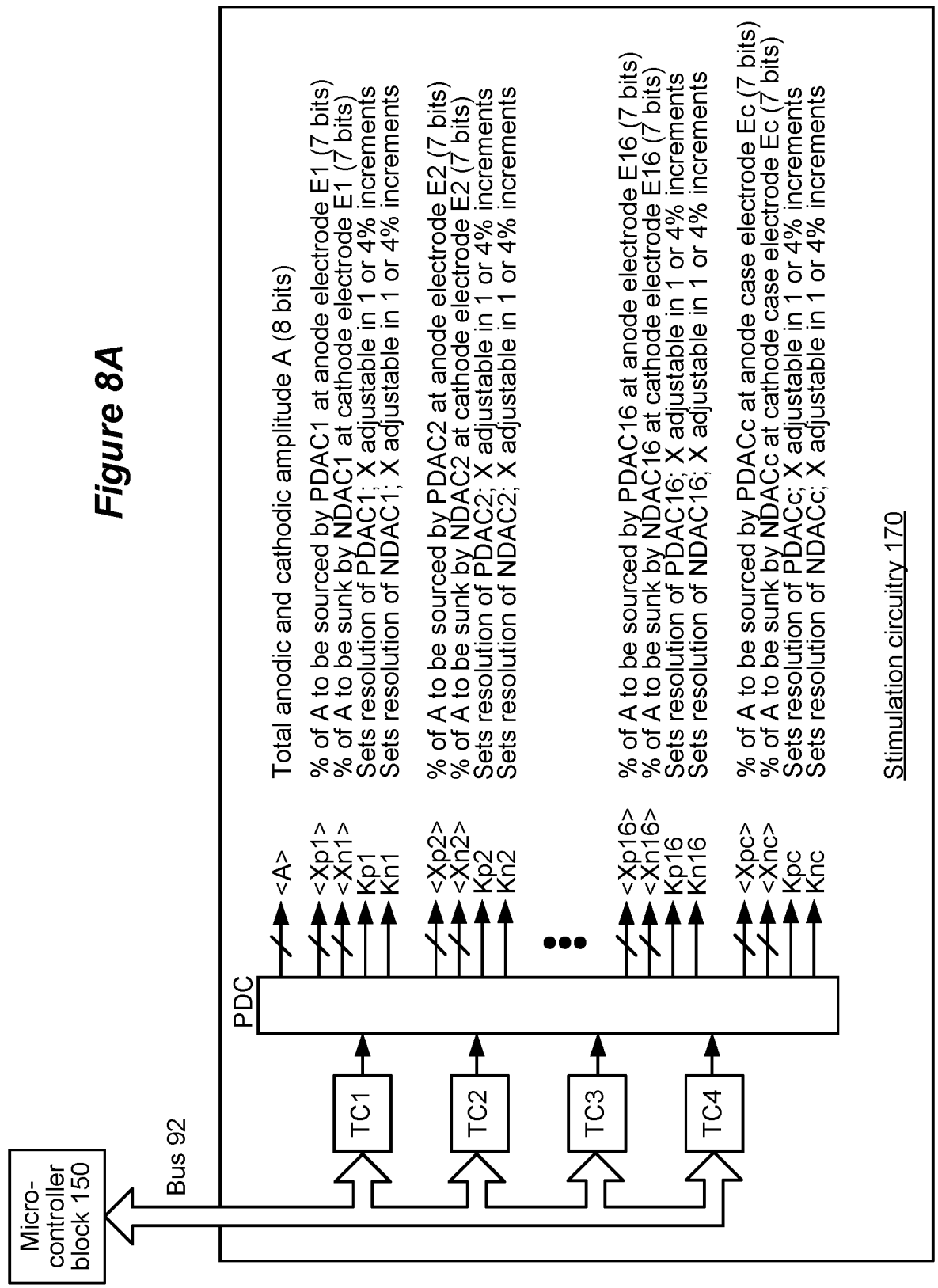
FIG. 8A shows a Pulse Definition Circuit (PDC) for providing the amplitude bus to the master DAC, and for providing the percentage busses and high/low resolution control signals to the PDACs and NDACs, which PDC receives information from different timing channels.
Figure 8B:
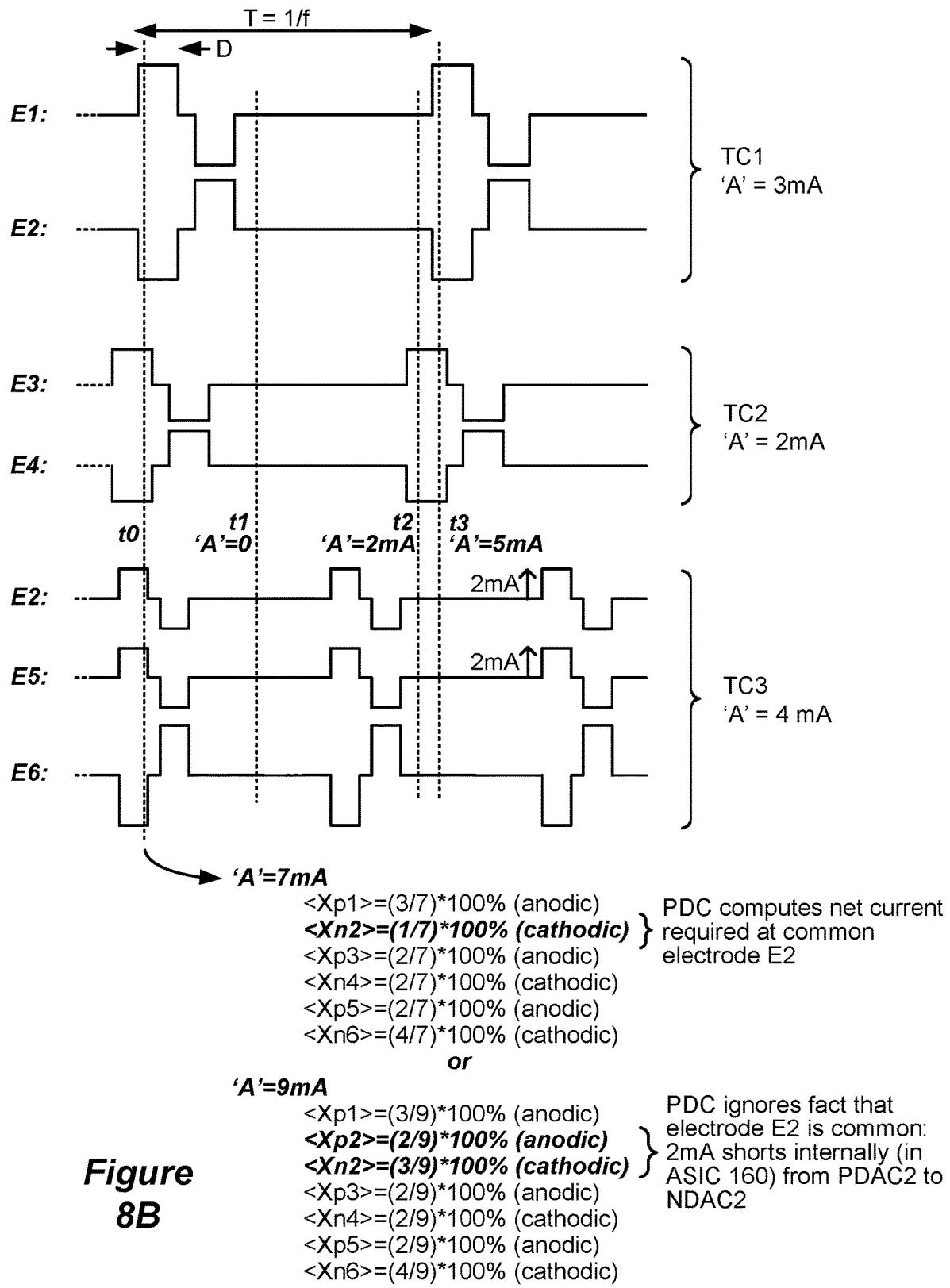
FIG. 8B shows how the PDC can control stimulation occurring on multiple timing channels.

FIG. 8A shows a Pulse Definition Circuit (PDCs) within stimulation circuitry 170 that outputs control signals <A>, <Xpi>, <Xni>, Kpi and Kni as already introduced. PDC, via these control signals, dictates the stimulation that will be issued by the DAC circuitry 172 at any given point in time. Providing data to the PDC are various timing channels (TC), four of which are shown, although different numbers could be used. A timing channel, as is well known, comprise a means for defining stimulation, and may run concurrently with stimulation defined and provided in a different timing channel. FIG. 8B shows examples of different stimulation pulses that may concurrently run in timing channels TC1-TC3. Each timing channel contains registers populated with data by microcontroller block 150 via bus 92 in accordance with a specified stimulation program to be run in that timing channel.

The PDC operates to assert control signals to form pulses specified in the timing channels TC1-TC3, and may additionally take various actions to resolve conflicts where pulses in the various timing channels overlap in time, as discussed further below. PDC may set amplitude bus <A> to 'A'=0 at times when no stimulation is to be provided by any timing channel, such as at time t1, and all <Xpi> and <Xni> may be set to 0 at these times as well.

At time t2, only the pulses in TC2 are issued. Hence PDC will set <A> in accordance with the total anodic and cathode amplitude required by that timing channel, i.e., 'A'=2 mA, and will additionally assert percentage bus control signals for PDAC3 (<Xp3>=100%>) and NDAC 4 (<Xn4>=100%) to form the specified anodic and cathodic current at electrodes E3 and E4 respectively. Notice that the duration (D) and frequency of the pulses is generally set by the PDC by issuing the percentages busses and amplitudes at appropriate times.

At time t3, the pulses in TC1 and TC2 overlap. Hence PDC in this example will need to provide a total anodic and cathodic amplitude sufficient to form the pulses in both timing channels. Because the pulses in TC1 require 3 mA and the pulses in TC2 require 2 mA, this totals 5 mA. However, the pulses in neither of these timing channels require the total 5 mA amplitude, meaning that the PDC must also adjust the percentage busses to ensure that pulses of proper amplitudes are formed. In other words, the PDC may adjust the percentage busses <Xi> from what they might otherwise be absent the overlap. Thus, because the pulses in TC1 require an amplitude of 3 mA, and because the total current required at time t3 is 5 mA in all timing channels, PDC will provide percentage bus signals to PDAC and NDAC circuitry involved in TC1 of 60% (i.e., 3 mA/5 mA). In other words, <Xp1> signals for PDAC1 at electrode E1 equal 60%, and <Xn2> signals for NDAC2 at electrode E2 equal 60%. Similarly, PDC will provide percentage bus signals to PDAC and NDAC circuitry involved in TC2 of 40% (i.e., 2 mA/5 mA). In other words, <Xp3> signals for PDAC3 at electrode E3 equal 40%, and <Xn4> signals for NDAC4 at electrode E4 equal 60%.

The PDC may also address the possibility that a common electrode may be activated by more than one timing channel at a time. Time t0 illustrates such a conflict: as well as the pulses in timing channels overlapping at time to, electrode E2 is active in both of timing channels TC1 and TC3. Further, notice that electrode E2 is simultaneously specified as a cathode (−3 mA) in TC1 and as an anode (+2 mA) in TC3.

PDC may take different actions when such a conflict arises. PDC may, for example, simply apply arbitration rules to prevent the pulses in the timing channels from overlapping in time, for example, by issuing the pulses in TC2; then after the pulses in TC2 have finished, issuing the pulses in TC3; and then after the pulses in TC3 have finished, issuing the pulses in TC1. Such arbitration would resolve the conflict of E2 having to act as a cathode and anode simultaneously. See, e.g., U.S. Patent Application Publication 2013/0184794 (discussing arbitration of stimulation pulses in different timing channels).

Alternatively, the PDC may sum the required current at common electrode E2 to determine the net current required at that electrode at that time, and set <A> and the percentage busses as necessary to form all specified pulses in the timing channels. For example, at time t0, PDC may cause the current at E2 to equal −3 mA+2 mA=−1 mA. The currents required at the other electrodes at time t0 are E1=+3 mA, E3=+2 mA, E4=−2 mA, E5=+2 mA, and E6=−4 mA. Thus, the total anodic and cathodic current required at t0 (when E2=−1 mA is included) is 'A'=7 mA, so PDC will set the amplitude bus <A> to this value.

PDC may then adjust the percentage busses in accordance with this summed amplitude from the various timing channels. For example, because 'A' is set to 7 mA, PDAC1 of electrode E1 will be set to <Xp1>=(3/7)*100%, or approximately 43% of the total anodic current, to create the specified +3 mA pulse at electrode E1 in TC1. PDC already determined that common electrode E2 should receive −1 mA by summing at time t0, and so NDAC2 at electrode E2 will be set to <Xn2>=(1/7)*100%, or approximately 14% of the total cathodic current. PDAC3 of electrode E3 will be set to <Xp3>=(2/7)*100%, or approximately 29% of the total anodic current; NDAC4 of electrode E4 will be set to <Xn4>=(2/7)*100%, or approximately 29% of the total cathodic current; PDAC5 of electrode E5 will be set to <Xp5>=(2/7)*100%, or approximately 29% of the total anodic current; and NDAC6 of electrode E6 will be set to <Xn6>=(4/7)*100%, or approximately 59% of the total cathodic current. Note that despite these adjustments, PDC via <Xpi> and <Xni> will cause 100% of the total anodic and cathodic current 'A'=7 mA to issue at time to.

PDC may also be configured to not sum the required current at common electrode E2, essentially ignoring the conflict that exists at this common electrode. Thus, PDC at time t0 may simply allow NDAC2 to issue −3 mA as required by TC1; and allow PDAC2 to issue +2 mA as required by TC3. Note that this is wasteful of IPG 10 power and its battery 14, because 2 mA of current would be shorted internally from PDAC2 to NDAC2 within the ASIC 160 to no useful effect; the remaining −1 mA would be sunk from NDAC2 from the tissue. Still, because such common-electrode conflicts should be relatively rare in time, such inefficiency can be tolerable. Should the PDC address conflicts in this manner, it would mean that the total anodic and cathodic current required at t0 is 'A'=9 mA, so PDC will set the amplitude bus <A> to this value.

Again, PDC will adjust the percentage bus signals accordingly. This is shown at the bottom of FIG. 8B. Specifically, PDAC of electrode E1 will be set to <Xp1>=(3/9)*100%, or approximately 33% of the total anodic current; PDAC2 of electrode E2 will be set to <Xp2>=(2/9)*100%, or approximately 22% of the total anodic current; NDAC2 of electrode E2 will be set to <Xn2>=(3/9)*100%, or approximately 33% of the total cathodic current; PDAC3 of electrode E3 will be set to <Xp3>=(2/9)*100%, or approximately 22% of the total anodic current; NDAC4 of electrode E4 will be set to <Xp4>=(2/9)*100%, or approximately 22% of the total cathodic current; PDAC5 of electrode E5 will be set to <Xp5>=(2/9)*100%, or approximately 22% of the total anodic current; and NDAC6 of electrode E6 will beset to <Xn6>=(4/9)*100%, or approximately 44% of the total cathodic current. Again in this example, PDC will cause 100% of the total anodic and cathodic current 'A'=9 mA to issue at time t0.

Details concerning software and hardware used to populate a PDC are disclosed in detail in U.S. Patent Application Publication 2018/0071513, which is incorporated by reference in its entirety.

Figure 9A:
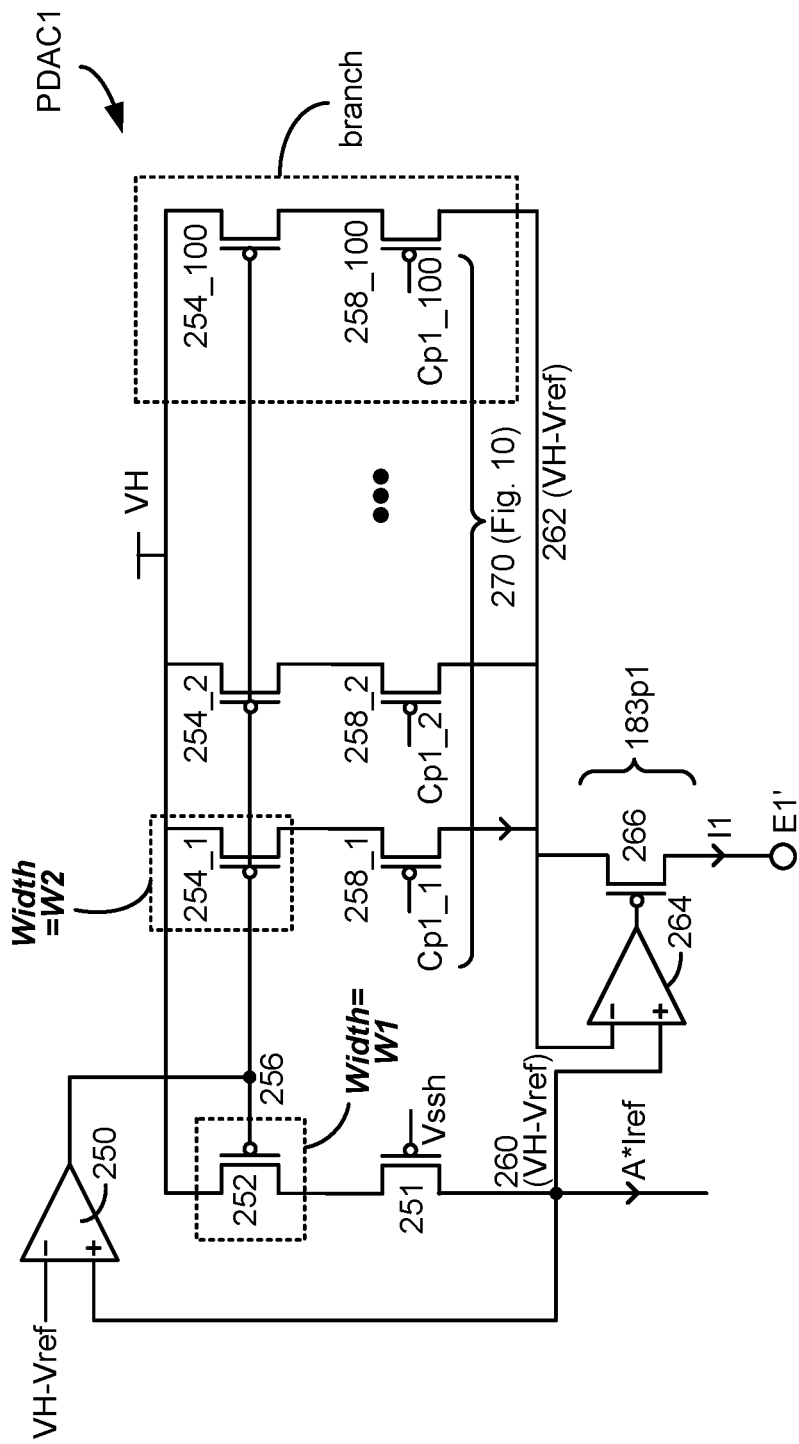
FIGS. 9A and 9B respectively show the circuitry details in one of the PDACs and in one of the NDACs, which includes a plurality of current branches controllable by switches.
Figure 9B:
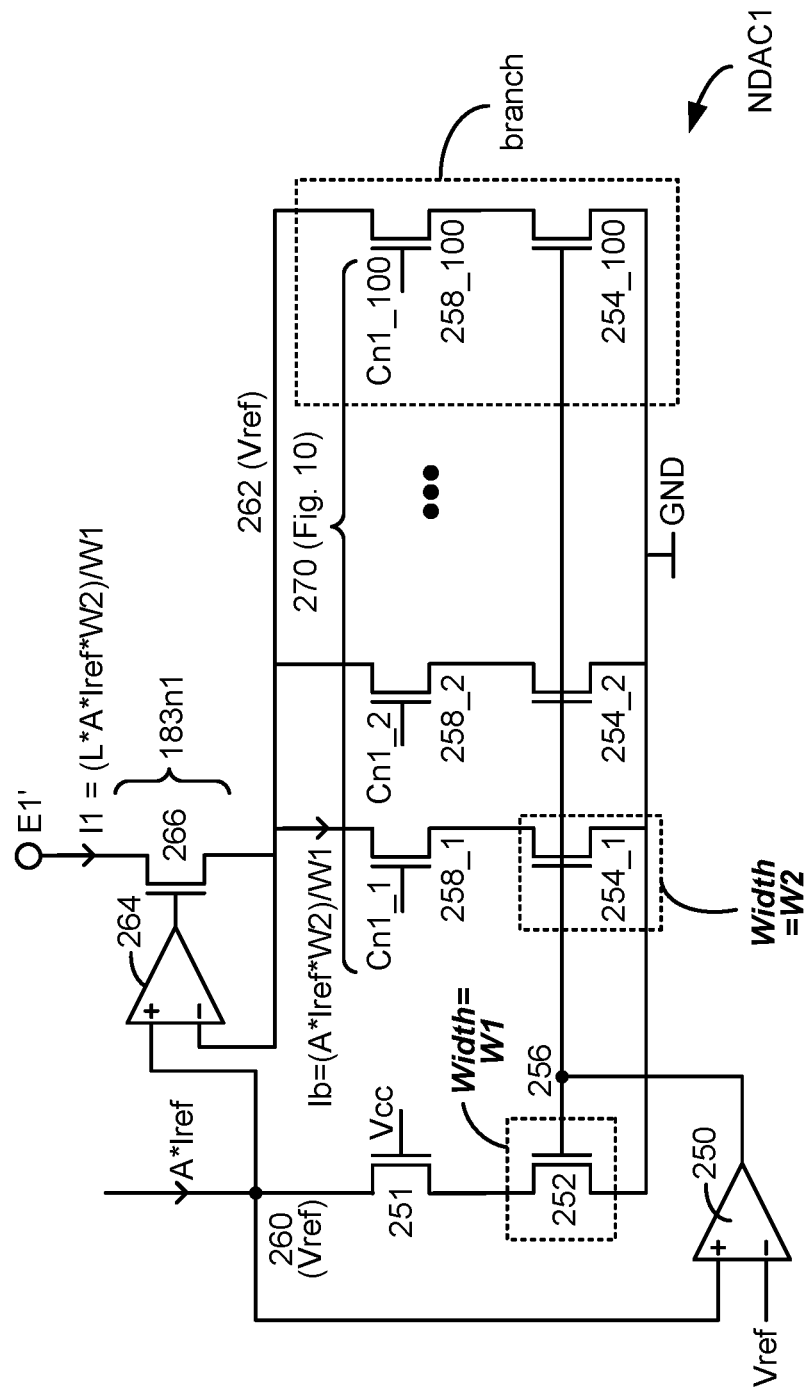

FIGS. 9A and 9B respectively show the circuitry for one of the PDACs (PDAC1) used to source current (+I1) to its electrode node (E1'), and the circuitry for one of the NDACs (NDAC1) used to sink current (−I1) from that electrode node. As a comparison of FIGS. 9A and 9B shows, the circuitry for the PDACs and NDACs are symmetric, although the PDACs are powered in the high power domain (VH/Vssh), while the NDACs are powered in the low power domain (Vcc/GND). Further, the polarity of the transistors in PDACs and NDACs are different, and thus control signals the PDACs receive (e.g., <C>) would be inverted from those received by the NDACs. Nonetheless, the PDACs in FIG. 9A essentially operate the same as does the NDACs in FIG. 9B. Thus, similar elements numerals are provided for the transistors in these figures, and both are discussed for simplicity primarily with reference to FIG. 9B.

NDAC1 in FIG. 9B receives at node 260 current A*Iref that was pushed to it by distributor 182n (FIG. 7B). This current passes through an always-on dummy transistor 251 to a resistance transistor 252. Resistance transistor 252 has a width W, and can be formed to achieve this width W1 by wiring a plurality of transistors together in parallel, although this isn't shown. The gate of resistance transistor 252 is connected at node 256 to the gates of several branch transistors 254, each of width W2, which is preferably wider than W1 used in the resistance transistor 252. Again, each branch transistor could comprise a plurality of transistors wired in parallel. In the example shown, there are 100 branch transistors 254, each of which is connected to a switch 258 controlled by a control signal Cn1. A different numbers of branches could be used as well. Notice that resistance transistor 252 and branch transistors 254 are not coupled in a current mirror configuration (gate node 256 is not coupled to drain of transistor 252). However, A*Iref is still reproduced into each of the branch transistors 254, preferably with some amplification, as explained further below. The other sides of switches 258 are connected to a node 262.

In a preferred example, each of the branch transistors 254 (W2) is sized relative to the resistance transistor 252 (W1) to set a resistance difference between them, such that the resistance transistor 252 is W2/W1 times more resistive than each branch transistors 254. Further included in NDAC1 are operational amplifiers (op amps) 250 and 264. Op amp 250 receives node 260 at one of its inputs, and a reference voltage Vref at its other input. Vref can be generated by any number of well-known voltage generator circuits (not shown), such as temperature-independent bandgap voltage generators. The output of op amp 250 is connected to node 256, which is connected to the gates of the resistance transistor 252 and the branch transistors 254 to turn them on. Through feedback through the resistance transistor 252 and dummy transistor 251, op amp 250 will force its input, node 260, to match its other input, Vref. Thus, node 260 held to Vref.

Node 260 is input to an output stage 183n1 comprising an op amp 264 and an output transistor 266. Specifically, node 260 is input to the op amp 264, which in turn controls output transistor 266 to allow current to flow to electrode node E1' via an electrode output path. The other input to the op amp 264, node 262, is connected to opposite side of the output transistor 266 from the electrode node. Through feedback through the output transistor 266, the op amp 264 will force node 262 to match input node 260. Thus, just as node 260 is held at Vref, so too is node 262 held at Vref.

Switches 258 allow current to be provided to the electrode node based on the status of switch control signals <Cn1>. Quantifying the value of the provided current is explained subsequently, but for now it can be assumed that each branch transistors 254 provides a single "unit" of current. For example, assume it is desired to sink three units of current from electrode node E1'. (Again, an NDAC1 is illustrated in FIG. 9B, but one of the PDACs (see FIG. 9A) would source units of current to the electrode nodes). This can be accomplished by asserting any three of the control signals <Cn1>, such as Cn1_1, Cn1_2, and Cn1_3. This closes switches 258_1, 258_2, and 258_3 associated with these control signals, and allows L=3 branch transistors, 254_1, 254_2, 2543, to each sink a unit of current from E1'. Thus, in sum, three units of current are sunk from electrode node E1' and hence electrode E1.

The quantity of current each branch provides is explained as follows. Assuming for the moment that the resistance of dummy transistor 251 is negligible compared to the resistance provided by the resistance transistor 252, Vref at node 260 is effectively dropped across the resistance transistor 252 (from its drain to its source). Current A*Iref flows through the resistance transistor 252, and therefore, the resistance of the resistance transistor 252 equals Vref/(A*Iref). Note that op amp 250 will set node 256 to a voltage necessary to bring resistance transistor 252 to this resistance.

The voltage drop across the branch transistors 254 are held to Vref just like the resistance transistor 252. Remember that node 262 is held at Vref, and thus is dropped across the series connection of the selected switches 258 and the active branch transistors 254. However, similar to the relationship of dummy transistor 251 to resistance transistor 252, the resistance across the switches 258 is negligible compared to the resistance of the branch transistors 254. As a result, Vref at node 262 is effectively dropped from the drain to the source of the branch transistors 254. Note that the width of the dummy transistor 251 (x*W1) can be sized relative to the width of the switches 258 (x*W2) in the same proportion that the resistance transistor 252 (W1) is sized relative to the branch transistors 254 (W2). This helps to ensure that the Vds drop across the branch transistors 254 equals that across the resistance transistor 252, which again is very close to Vref (perhaps approximately 100 mV smaller than Vref once the resistance of the dummy transistor 251 and switches 258 are considered).

Because the resistance of the resistance transistor 252 is Vref/(A*Iref), and because the resistance of the branch transistors 254 is W2/W1 less resistive, the resistance of each of the branch transistors 254 will be (Vref*W1)/(W2*A*Iref). Therefore, the current through each of the selected branch transistors 254 (Ib) can be calculated by dividing the voltage (Vref) across each branch transistor 254 by its calculated resistance, and so Ib=(A*Iref*W2)/W1. Because W2 is preferably larger than W1, notice that the current provided by the master DAC 180 (A*Iref) is amplified by a factor of W2/W1 in each of the selected branches. The currents Ib formed in each of the L (e.g., 3) active branches are then summed at node 262, and passed through output transistor 262, providing a total sunk current at electrode node E1' of I1=(L*A*Iref*W2)/W1.

Exemplary values assist in understanding NDAC1's operation, and the magnitudes of the various currents it produces. As described earlier, the master DAC 180 in one example can output currents A*Iref of 100 nA, 200 nA, 300 nA, . . . , 25.5 µA, depending on the value of the 'A' as set by amplitude bus <A>, and assuming a maximum value of 'A' of 255. Assume that the width W2 of the branch transistors 254 are 10 times the width W1 of the resistance transistor 252 (i.e., W2/W1=10). Each branch transistors 254 will amplify A*Iref current by this ratio, and thus be able to provide currents of Ib=1 µA, 2 µA, 3 µA, . . . , 255 µA (again, depending on 'A'). If it is assumed that all branches are selected (L=100), NDAC1 can produce a summed value of I1=0.1 mA, 0.2 mA, 0.3 mA, . . . , 25.5 mA.

It should be noted that the reference current (Iref), the maximum amount by which the reference current can be amplified by the master DAC 180 (A), the relative widths of the resistance transistor 252 and the branch transistors 254 (W1 and W2), or their relative resistance more generally, and the maximum number of branches (L) can all be adjusted in different designs. Further, W2/W1 may equal one, and so each branch may simply reproduce A*Iref (i.e., Ib=A*Iref), which may still be considered an amplification of A*Iref in each branch. Alternatively, W2/W1 may even be less than one, meaning Ib would be smaller than A*Iref, which again may be considered as amplification.

Software limitations may also operate to constrain the total amount of current that the ASIC 160 can provide to the electrodes at any given time. For example, each PDAC and NDAC as described can source or sink 25.5 mA from its electrode, meaning in a 17 electrode IPG 10 (E1-E16, plus Ec) that the IPG could source or sink a total of 17*25.5 mA=433.5 mA. Such a large amount of current may be impractical: the compliance voltage VH may not be able to produce this, or the drain on the IPG's battery 14 may be too extreme. Such a large amount of current may also simply be unsafe. Thus, the total sourced or sunk current at any given time may be software limited to a more practical and safer value, such as 25.5 mA, even though such total value is below what the PDACs and NDACs together are capable of producing. Such limitation may be employed in software in the IPG 10 (in microcontroller block 150), or in the external controller used to program the IPG, that is, as a limitation constraining stimulation settings in the software of a clinician programmer or a hand-held patient programmer.

FIG. 9A shows an example of one of the PDACs (PDAC1). As one skilled in the art will appreciate, the circuitry for PDAC1 is largely "inverted" from that shown for NDAC1 in FIG. 9B, and has expected differences given its difference in polarity. For example, current-producing portions of PDAC are coupled to the compliance voltage VH instead of ground, thus allowing PDAC1 to source current to electrode node E1', allowing electrode E1 to operate as an anode (positive current). Notice that the reference voltage used by the PDACs comprises VH−Vref. This reference voltage will vary because, as explained in the Introduction, VH varies to keep the PDACs and NDACs operating at a power-efficient level. Further implications stemming from the variability of the compliance voltage VH are discussed later in conjunction with FIGS. 13A-14D.

Figure 10A:
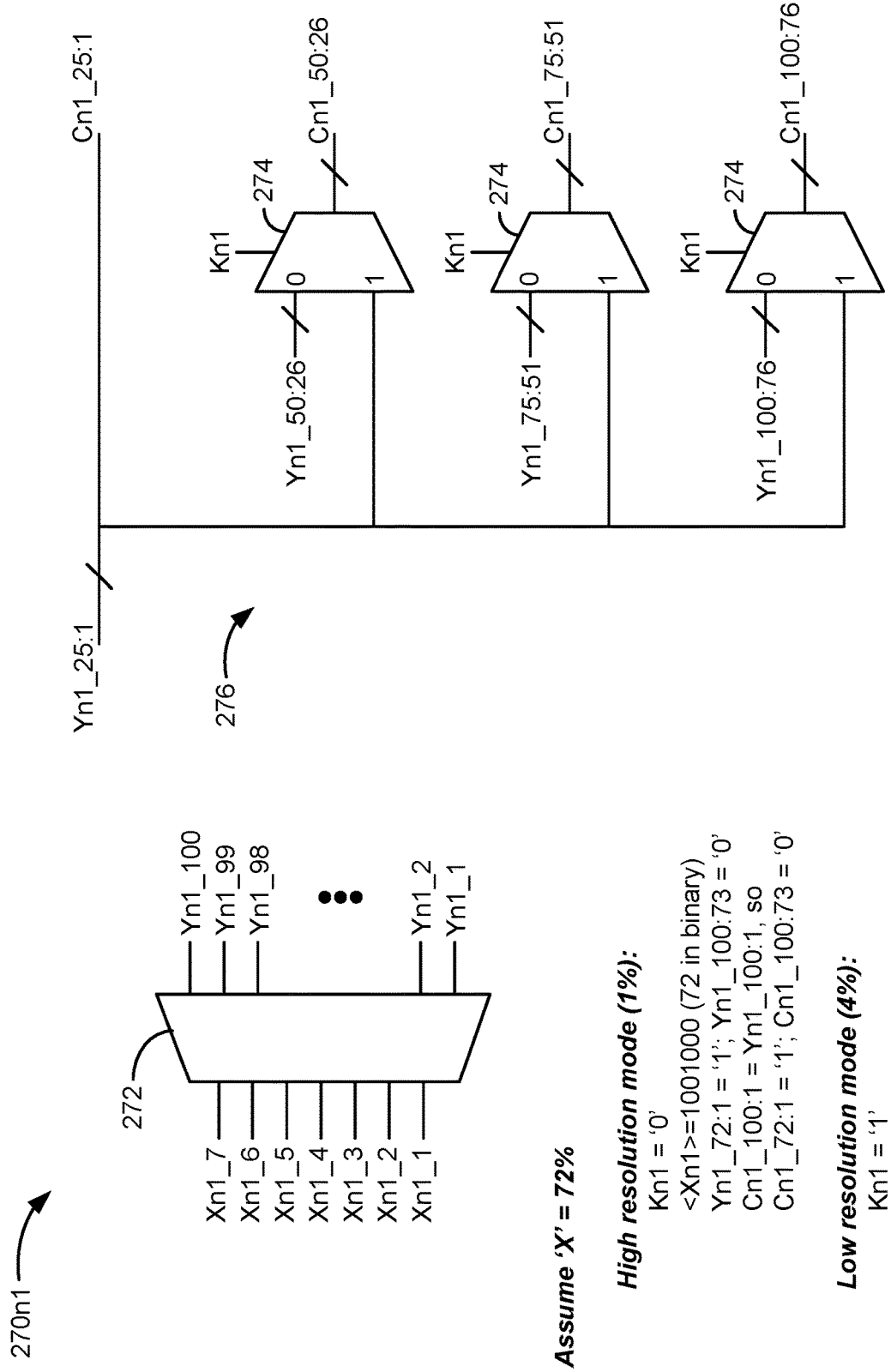
FIGS. 10A and 10B show logic circuitry for generating the switch control signals for the branches in the PDACs and NDACs, which logic circuitry is controlled in accordance with the resolution control signals.

To review, the magnitude of the current provided by a PDACi or NDACi to its associated electrode node Ei' is set by controlling the magnitude of 'A' from the master DAC 180, and by controlling switch control signals <Ci> to add or remove active branches from the DAC. Control signals <Ci> are generated from the percentage bus <Xpi> or <Xni> and resolution control signal Kpi or Kni sent to each PDACi and NDACi by the PDC (FIG. 8A). The logic circuitry 270 used to convert <Xni> and Kni to <Cni> is shown in FIG. 10A. The logic circuitry 270 is shown specifically for NDAC1 (207n1), but each PDAC and NDAC would have similar circuitry 270. Logic circuitry 270 for each PDAC and NDAC can be considered part of that PDAC or NDAC.

FIG. 10A includes logic circuitry 272, preferably a thermometer decoder, which receives the percentage bus for NDAC1, <Xn1>, shown as 7 bits Xn1_7:1. Thermometer decoder 272 will assert a number of intermediate signals <Yn1>, shown as 100 bits Yn1_100:1. These intermediate signals <Yn1> are then input to a multiplexer stage 276 that includes a number of different multiplexers 274, which output the switch control signals Cn1_100:1 received by NDAC1 and described earlier (FIG. 9B). Notice that the multiplexers 274 are controlled by the resolution control signal Kn1, which by way of review sets an amount by which each PDAC or NDAC's percentage 'X' can be adjusted. Specifically, Kn1 controls whether the percentage 'X' for NDAC1 will be variable in 1% increments in a high resolution mode, or 4% increments in a low resolution mode.

Operation in a high resolution mode is described first, and using an example in which NDAC is to receive 72% of the total cathodic amplitude 'A'. (Although not shown, some other electrode(s)' NDAC(s) would be responsible for producing the remaining 28% of the total cathodic current). In high resolution mode, the resolution control for NDAC1, Kn1, would be set to '0'. Further, the PDC, knowing that high resolution mode is desired for NDAC1, would set the percentage signals for NDAC1, <Xn1>, to the desired percentage of 72 in binary, or '1001000.' (Seven bits for <Xn1> are required to encode percentages from 1 to 100). Thermometer decoder 272 would in turn assert intermediate control signals Yn1_72:1 ('1'), and unassert all other outputs Yn1_100-73 ('0').

Intermediate signals <Yn1> are passed to the multiplexer stage 276. Notice that the least-significant 25 bits, Yn1_25:1, are simply passed as the least-significant 25 switch control signal bits, Cn1_25:1. Thus, for 'X'=72%, all of Cn1_25:1 would be asserted. When Kn1='0', the multiplexers 274 would also pass different groups of the intermediate control signals Yn1 to their corresponding switch control signals, i.e., Cn1_50:26 is set to Yn1_50:26, Cn1_75:51 is set to Yn1_75:51, and Cn1_100:76 is set to Yn1_100:76. Thus, for 'X'=72%, multiplexers 274 would assert Cn1_72:26, and unassert Cn1_100:73.

In low resolution mode, the resolution control for NDAC1, Kn1, would be set to '1'. Further, the PDC, knowing that low resolution mode is desired for NDAC1, would divide the desired percentage by four, i.e., 72/4=18. The PDC would then set the percentage signals for NDAC1, <Xn1>, to 18 in binary, or 'xx10010.' (Because a maximum value of 100/4=25 is required in low resolution mode, only five of the seven bits of <Xn1> are required; in effect most-significant bits Xn1_7 and Xn1_6 become "don't care" values). Thermometer decoder 272 would in turn assert intermediate control signals Yn1_18:1 ('1'), and unassert all other outputs Yn1_100-19 ('0').

Intermediate signals <Yn1> are passed to the multiplexer stage 276. Again, the least-significant 25 bits, Yn1_25:1, are simply passed as the least-significant 25 switch control signal bits, Cn1_25:1. Thus, in low resolution mode, for 'X'=72%, all of Cn1_18:1 would be asserted, and Cn_25:19 would be unasserted. Because Kn1='1', the multiplexers 274 would pass these same the least-significant 25 bits, Yn1_25:1, to the remaining groups of the switch control signals. Thus, Cn1_50:26, Cn1_75:51, and Cn1_100:76 are all set to Yn1_25:1. Thus, for 'X'=72%, multiplexers 274 would assert Cn1_18:1, Cn1_43:26, Cn1_68:51, and Cn1_93:76, and unassert Cn1_25:19, Cn1_50:44, Cn1_75:69, and Cn1_100:94.

Figure 10B:
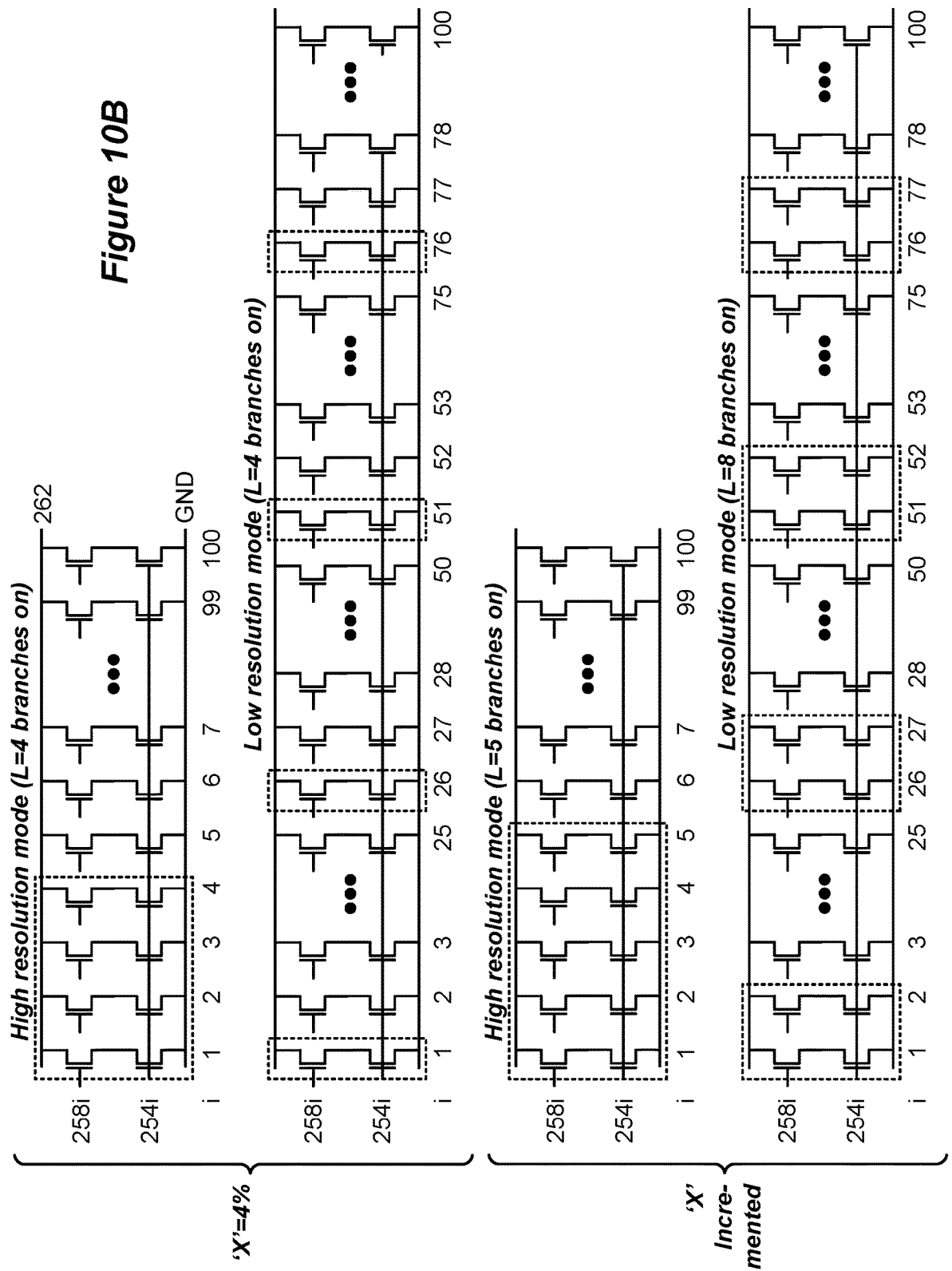

In either the high or low resolution mode, the current produced by the DAC is the same, although the particular branches turned on in the DAC can differ. This is shown in FIG. 10B for a generic NDAC, although the PDAC would be similar. The top of FIG. 10B shows a simple case in which 'X'=4%. Both high and low resolution modes are shown, with active branches in the NDAC enclosed by dotted lines. Through operation of the logic circuitry 270 of FIG. 10A, in the high resolution mode, intermediate signals Y4:1 would be asserted, meaning switch control signals C4:1 would likewise be asserted, thus turning on the first four branches in the NDAC. However, in the low resolution mode, only intermediate signal Y1 would be asserted. Operation of the multiplexer stage 276 would accordingly assert C1, C26, C51, and C76. Thus, four (different) branches of the NDAC (PDAC) are turned on. Because four branches are turned on for each resolution, the NDAC (PDAC) in either case will sink (source) the same amount of current—i.e., 4% of the total cathodic (anodic) amplitude 'A'.

The resolution mode affects how the percentage 'X' can be incremented or decremented in a DAC, which is constrained by the number of branches that the logic circuitry 270 can turn on in each mode. Assume for example that 'X' is incremented from 4% in FIG. 10B. If the PDC specifies that the DAC at issue operates in the high resolution mode, incrementing 'X' means that X will now equal 5%, because 'X' can be incremented in 1% steps. Incrementing 'X' in this fashion, and through operation of logic circuitry 270, will assert intermediate signals Y5:1, and thus switch control signals C5:1, thus turning on the first five branches of the DAC, and producing 5% of 'A' from the DAC as shown at the bottom of FIG. 10B. By contrast, if the PDC specifies that the DAC at issue operates in the low resolution mode, incrementing 'X' means that X will now equal 8%, because 'X' will be incremented in 4% steps. Incrementing 'X' in this fashion, and through operation of logic circuitry 270, will assert intermediate signals Y2:1, and thus switch control signals C1, C2, C26, C27, C51, C52, C76, and C77 will be asserted, turning on eight branches of the DAC, and producing 8% of 'A' from the DAC.

In effect, in the depicted example, in the high resolution mode, each of the DAC's branches are asserted/unasserted one at a time when 'X' is incremented/decremented, and in physical order in the DAC. In the high resolution mode, the logic circuitry 270 in effect ties switch control signals Ci, C(i+25), C(i+50), and C(i+75) together, thus permitting only groups of 4 branches (in physically different locations) to be chosen. However, it should be noted that which of the physical branches are chosen will depend on the layout of the DAC. For example, if the switch control signals C100:1 are not sent to sequentially physical branches in the DAC as in the illustrated examples, different physical branches would be selected to contribute to the current the DAC produces.

Figure 10C:
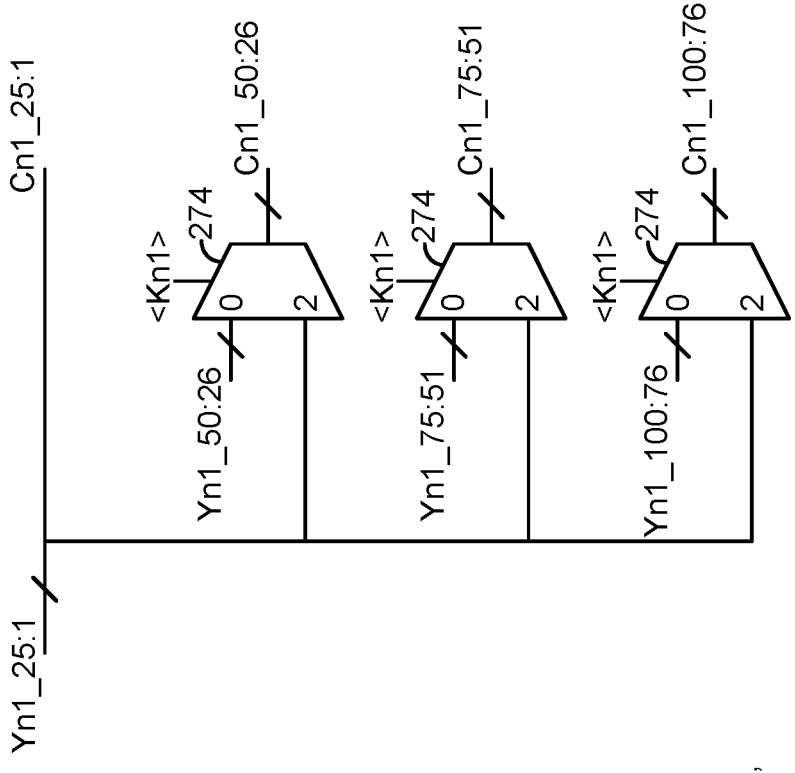
FIG. 10C shows modification of the logic circuitry allowing it to be controlled by multiple resolution control signals.

It should be noted that the improved DAC circuitry 172 can be extended to allow percentage 'X' to be changed with more than two resolutions. For example, FIG. 10C shows a modification to allow percentage 'X' to be adjusted in a high resolution mode (in 1% percent increments), a medium resolution mode (in 2% increments), and in a low resolution mode (in 4% increments). In this modification, resolution control signals comprise a bus <Kn1> able to indicate operation in high resolution mode (when <Kn1>='00'=0), in medium resolution mode (when <Kn1>='01'=1), and in low resolution mode (when <Kn1>='10'=2). Logic circuitry 270 includes a first multiplexer stage 276 essentially similar to that described earlier, except that it is not enabled in the medium resolution mode. A second multiplexer stage 277 is enabled only in the medium resolution mode (when <Kn1>=1). In this mode, PDC would take the desired percentage (72%), divide it by two (36), and assert this value in binary on percentage control signals <Xn1>, i.e., 'x100100.' Thermometer decoder 272 (FIG. 10A) would assert intermediate signals Y36:1, which multiplexer 278 in second multiplexer stage 277 would pass to both C36:1 and C86:51. In effect then, in the medium resolution mode, DAC branches would be asserted two at a time (C1 and C51, C2 and C52, etc.), thus providing 2% increments of amplitude 'A' to be output by the DAC. This is just one example in which a multi-resolution mode could be implemented, and other examples are possible.

As illustrated to this point, it is preferred that each PDAC and NDAC be provided its own resolution control signals, i.e., Kp1, Kn1, Kp2, Kn2, etc., thus allowing for independent resolution control of each PDAC and NDAC. However, in other examples, a single resolution control signal K could be used to control the resolution of all PDACs and NDACs. Alternatively, a single resolution signal could be provided to each PDAC/NDAC pair dedicated to a particular electrode—e.g., Kp1 and Kn1 could comprise a single control signal Kl.

Figure 11A:
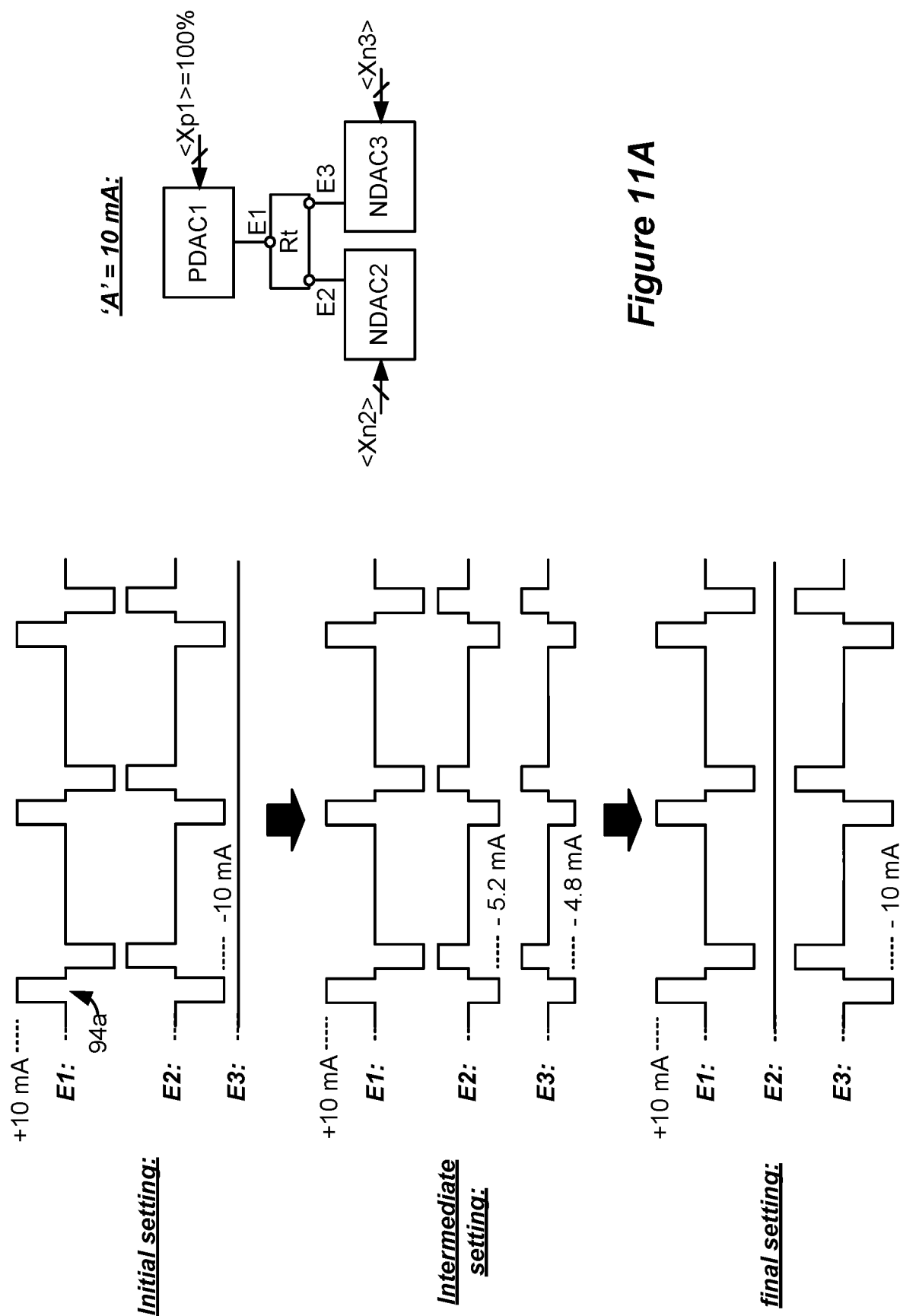
FIG. 11A shows use of the improved DAC circuitry to steer a current between electrodes in a timing channel, with FIG. 11B showing steering in a high resolution mode, and FIG. 11C showing steering in a low resolution mode.

As mentioned above, the percentage busses <X> provide a convenient way to "steer" current between different electrodes. Steering involves moving some portion of anodic current between two or more electrodes, or moving some portion of cathodic current between two or more electrodes. An example of current steering is shown in FIG. 11A, which involves use of electrode E1 as an anode, and electrodes E2 and E3 as cathodes (during first pulse phases 94a). In this example, cathodic current (−10 mA) is steered from E2 to E3 in gradual increments: initially, the entirety of the cathodic current is placed on E2, but eventually at the end of steering the entirety of the cathodic current is placed on E3. An intermediate setting is shown during the steering process at which the cathodic current at electrodes E2 and E3 are roughly equal (−5.2 mA and −4.8 mA). In this example, the anodic current issued from E1 stays constant (+10 mA), but anodic current may also be steered to and from different electrodes in more complicated examples.

Steering current between electrodes in small increments is a desirable use model, particularly during fitting of the IPG 10 to a particular patient. This because it may not initially be known what electrodes should be chosen for stimulation to relieve a patient's symptoms (e.g., pain). Gradually moving current between electrodes to determine which electrodes should be active to provide therapy, and in what proportions, may be more comfortable and less dangerous for the patient. For example, if all of the cathodic current is moved instantaneously from E2 to E3 in the example of FIG. 11A (from the initial setting to the final setting), the effect may be jarring on the patient. Moving current in gradual increments reduces this risk, and allows finer tuning of therapy as source current can be shared by one or more selected anode electrodes, and sink current can be shared by one or more selected cathode electrodes. See U.S. Pat. No. 7,890,182, discussing this issue in further detail. Moving current in the manner shown can be performed by a clinician programmer running IPG control software in communication with a patient's IPG 10. Alternatively, current may also be movable between electrodes by the patient using a hand-holdable external controller. Alternatively, the current may be moved automatically by the IPG 10, i.e., by the microcontroller block 150 or the PDC (see FIG. 8A).

FIGS. 11B and 11C shows how steering current between the electrodes E2 and E3 of FIG. 11A can be achieved using DAC circuitry 172, in high and low resolution modes respectively. In both cases, amplitude bus <A> sets a value 'A' of 10 mA—the total anodic and cathodic current required. Notice that percentage bus <Xp1>=100%, because all anodic current will be provided by PDAC1 associated with electrode E1. Bus <Xn1>=0%, because E1 is not acting as a cathode, and thus NDAC1 will be inactive. Likewise busses <Xp2> and <Xp3>=0% because electrodes E2 and E3 are not acting as anodes, and thus PDAC2 and PDAC3 will be inactive. Finally, all other percentage busses (<Xp4>, <Xn4>, <Xp5>, <Xn5>, . . . , <Xp16>, <Xn16>, <Xpc>, Xnc>) are set to 0%, because electrodes E4-E16 and Ec are not selected for stimulation, and hence their PDACs and NDACs are inactive.

FIG. 11B illustrates steering in the high resolution mode. Thus, the resolution control signals for electrode E2 and E3's NDACs—Kn2 and Kn3—are set to '0', and PDC will issue a percentage signals <Xn2> and <Xn3> from 0 to 100 in 1% increments (using all of bits Xn_7:1). Each 1% adjustment occurs at sequential times t0, t1, t2, . . . , t100, which adjustments can again be made using a clinician programmer or patient external controller, and wirelessly transmitted to the IPG 10. At time t0, PDC sets <Xn2> to 100%, and thus logic circuitry 270 (FIG. 10A) will assert all 100 branches in NDAC2 (Cn2_100:1 are asserted) and so electrode E2 outputs 100% of 'A' (−10 mA); PDC sets <Xn3> to 0%, and thus no branches are asserted in NDAC3 (Cn3_100:1 are unasserted) and so electrode E3 outputs 0% of 'A' (0 mA). At time t1, where a 1% increment of 'A' is moved from E2 to E3, PDC sets <Xn2> to 99%, and 99 branches in NDAC2 are asserted (Cn2_99:1) and so electrode E2 outputs 99% of 'A' (−9.9 mA); PDC sets <Xn3> to 1%, and thus one branch in NDAC3 is asserted (Cn3l) and so electrode E3 outputs 1% of 'A' (−0.1 mA). This continues as shown in FIG. 11B until, at time t100, PDC sets <Xn2> to 0%, and thus no branches in NDAC2 are asserted (Cn2_100:1 are unasserted) and so electrode E2 outputs 0% of 'A' (0 mA); PDC sets <Xn3> to 100%, and thus all branches are asserted in NDAC3 (Cn3_100:1 are asserted)

and so electrode E3 outputs 100% of 'A' (−10 mA). At this point, all cathodic current has been steered from electrode E2 to electrode E3.

FIG. 11C illustrates steering in the low resolution mode. Thus, the resolution control signals for electrode E2 and E3's NDACs—Kn2 and Kn3—are set to '1', and PDC will issue a percentage signals <Xn2> and <Xn3> from 0 to 25 (0% to 100%) in 4% increments (using only bits Xn_5:1). Each 4% adjustment occurs at sequential times t0, t1, t2, . . . , t25; notice that because the resolution is lower in FIG. 11C than in FIG. 11B, it takes less time (t100 versus t25) to completely steer the cathodic current from electrode E2 to electrode E3. At time t0, PDC sets <Xn2> to 25 (100%), and thus logic circuitry 270 (FIG. 10A) will assert all 100 branches in NDAC2 (Cn2_100:1 are asserted) and so electrode E2 outputs 100% of 'A' (−10 mA); PDC sets <Xn3> to 0%, and thus no branches are asserted in NDAC3 (Cn3_100:1 are unasserted) and so electrode E3 outputs 0% of 'A' (0 mA). At time t1, where a 4% increment of 'A' is moved from E2 to E3, PDC sets <Xn2> to 24 (96%), and 96 branches in NDAC2 are asserted (Cn2_99:76, 74:51, 49:26, 24:1) and so electrode E2 outputs 96% of 'A' (−9.6 mA); PDC sets <Xn3> to 1 (4%), and thus four branches in NDAC3 are asserted (Cn3_76, 51, 26, 1) and so electrode E3 outputs 4% of 'A' (−0.1 mA). This continues as shown in FIG. 11C until, at time t25, PDC sets <Xn2> to 0%, and thus no branches in NDAC2 are asserted (Cn2_100:1 are unasserted) and so electrode E2 outputs 0% of 'A' (0 mA); PDC sets <Xn3> to 25 (100%), and thus all branches are asserted in NDAC3 (Cn3_100:1 are asserted) and so electrode E3 outputs 100% of 'A' (−10 mA). At this point, all cathodic current has been steered from electrode E2 to electrode E3.

FIGS. 12A-12F show an alternative for DAC circuitry 172 in which a plurality of PDAC/NDAC pairs are dedicated to and able to provide a current at a particular electrode. In the example shown in FIG. 12A, there are two PDACs (PDACia, PDACib) and two NDACs (NDACia, NDACib) dedicated to each electrode node Ei'. While not strictly necessary, in the example depicted, each pair is dedicated to providing currents within a given timing channel. Thus, PDACia/NDACia source/sink current to/from electrode Ei in timing channel TCa, while PDACib/NDACib source/sink current to/from electrode Ei in timing channel TCb. The PDACs at a given electrode, and the NDACs at a given electrode, may be identical; for example, they may have the same number of branches as described earlier. Alternatively, the PDACs at a given electrode, and the NDACs at a given electrode, may be different; for example, they may have different number of branches and thus provide currents of different resolutions, as explained subsequently. In a preferred example, DAC circuitry 172 includes four PDAC/NDAC pairs at each electrode, with each pair providing currents in accordance with its own timing channel (e.g., TCa, TCb, TCc, and TCd), although this isn't illustrated in FIGS. 12A-12F for simplicity.

Figure 12A:
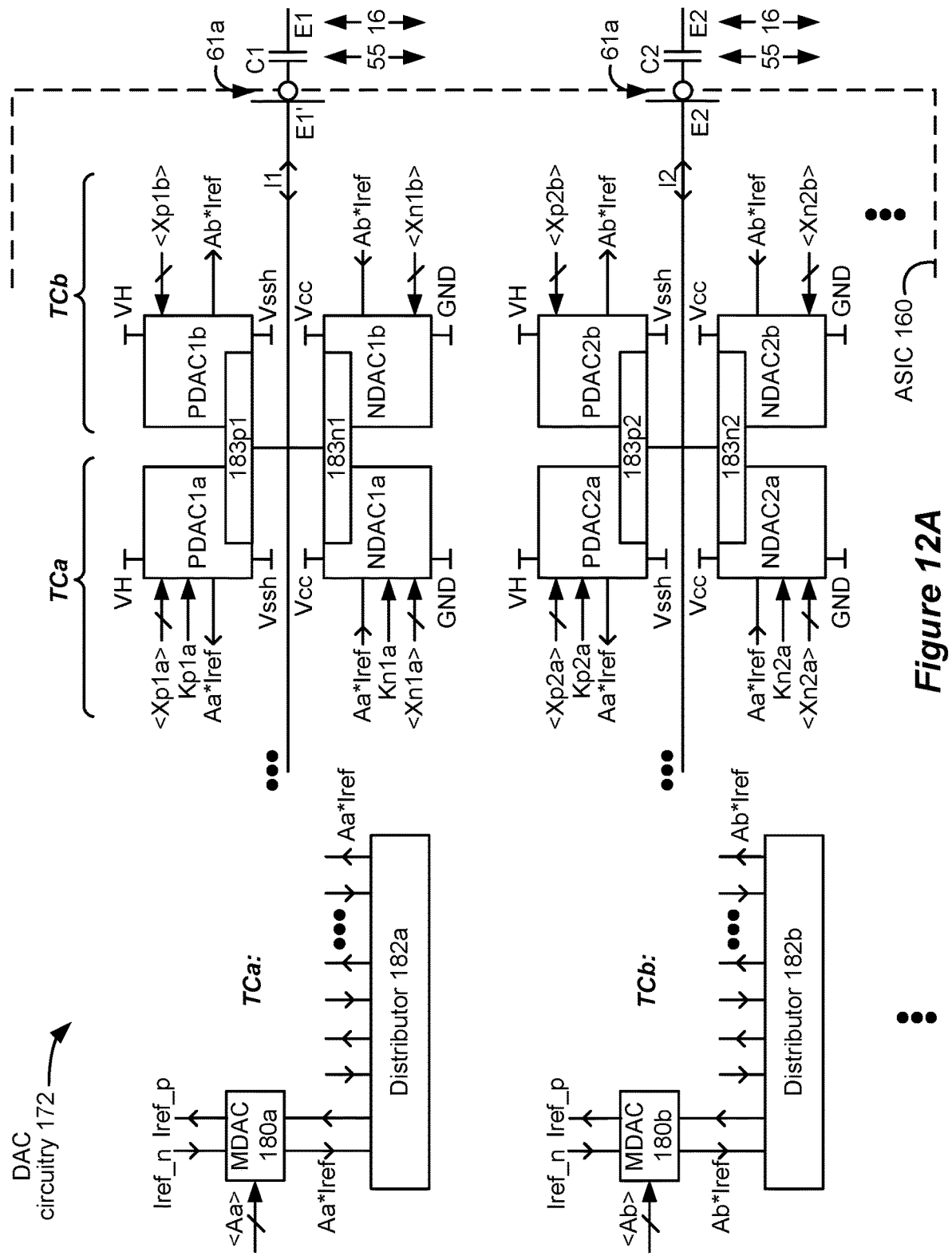
FIGS. 12A-12F show an alternative example of the improved DAC circuitry in which multiple PDAC/NDAC pairs are dedicated to each electrode, which pairs are preferably controlled in different timing channels.

DAC circuitry 172 in FIG. 12A further includes a master DAC and distributor that operate with each timing channel. For example, master DAC 180a and distributor 182a operate with timing channel TCa, while master DAC 180b and distributor 182b operate with timing channel TCb. Each master DAC 180 receives an amplitude bus that sets the total anodic and cathodic current of stimulation pulses in the relevant timing channel. Thus, master DAC 180a receives amplitude bus <Aa>, which sets a total amplitude of 'Aa' for pulses in timing channel TCa, while master DAC 180b receives amplitude bus <Ab>, which sets a total amplitude of 'Ab' for pulses in timing channel TCb. As before, each master DAC outputs an amplified version of a reference current, with its associated distributor providing that amplified current to PDACs and NDACs associated with that timing channel. Thus, master DAC 180a outputs amplified currents Aa*Iref, with distributor 182a providing those currents to PDAC1a, NDAC1a, PDAC2a, NDAC2a, etc., that operate within timing channel TCa. (Again, the amplified currents are of differing polarities depending whether they are sent to PDACs or NDACs, as explained earlier). Likewise, master DAC 180b outputs amplified currents Ab*Iref, with distributor 182b providing those currents to PDAC1b, NDAC1b, PDAC2b, NDAC2b, etc., that operate within timing channel TCb.

As shown in FIG. 12A, each of the PDACs at a given electrode node Ei' preferably share the same output circuitry 183pi, and each of the NDACs at that electrode preferably share the same output circuitry 183ni. This will be shown in more detail with respect to FIGS. 12D and 12E. Also, it should be noted that each PDAC and NDAC preferably has logic circuitry 270 (FIG. 10A) associated with it as described earlier, although this isn't shown in FIG. 12A for simplicity.

Each of the PDACs and NDACs operating in timing channel TCa receive percentage bus control signal <Xpia> and <Xnia>, which dictate the percentage of the total anodic and cathodic current 'Aa' that electrode Ei will receive. Each of the PDACs and NDACs operating in timing channel TCa also receive at least one resolution control signal Kpia and Knia. As before, these resolution control signals allow the PDACs and NDACs in timing channel TCa to operate in high or low resolution modes, thus allowing the percentage of 'Aa' that these PDACs or NDACs output to be changed in increments of 1% or 4% for example. Each of the PDACs and NDACs operating in timing channel TCb also receive percentage bus control signal <Xpib> and <Xnib>, which dictate the percentage of the total anodic and cathodic current 'Ab' that electrode Ei will receive. However, in this example, the PDACs and NDACs operating in timing channel TCb do not receive resolution control signal. This means that the resolution of these PDACs and NDACs is set and not adjustable. In a preferred example, the PDAC and NDACs in timing channel TCb are set to a low resolution mode, and thus the percentage of 'Ab' that these PDACs or NDACs can output is set to increments of 4% for example. However, resolution control signals may be used in timing channel TCb as well.

Figure 12B:
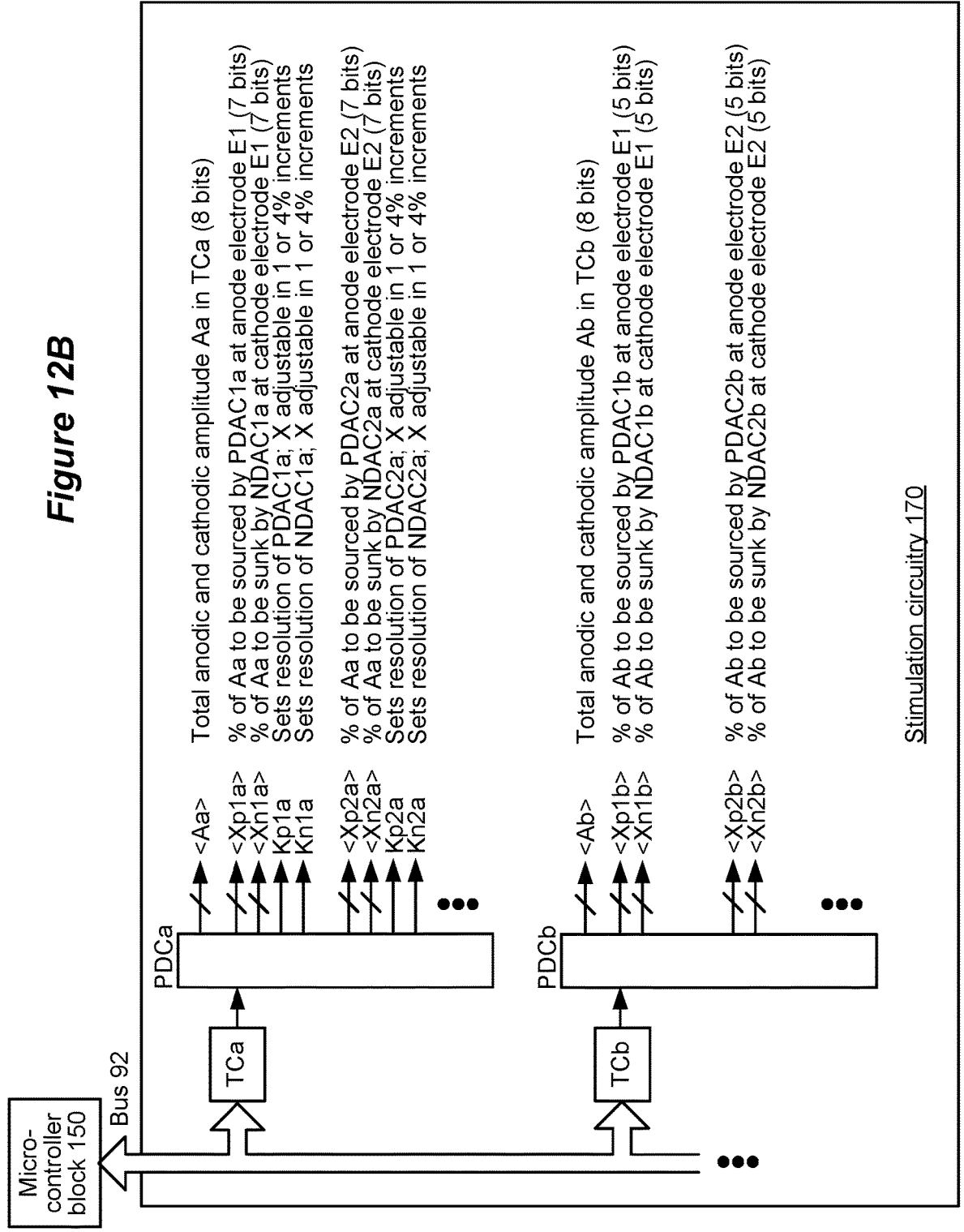

FIG. 12B summarizes the various control signals sent to the PDACs and NDACs in the example of FIG. 12A. In example, there are different Pulse Definition Circuits (PDCs) dedicated to each of the timing channels. Thus, PDCa provides the signals necessary to form stimulation pulses in TCa, including amplitude bus <Aa>, percentage control signals <X> and resolution control signals K. PDCb provides the signals necessary to form stimulation pulses in TCb, including amplitude bus <Ab> and percentage control signals <X>, but again in this example, there are no resolution control signals K in TCb. As shown, data for TCa is received from the microcontroller block 150 via bus 92, and stored in a timing channel register for use by PDCa. Data for TCb is similarly received and stored in a different timing channel register for use by PDCb. Notice then that PDCs form the pulses in their respective timing channels without consideration of the pulses being formed by other PDCs in other timing channels. Thus, in this example, and by contrast to the single PDC used in FIG. 8A, the PDCs do not consider whether their might be overlapping pulses in different timing channels, or whether an electrode might be common to more than one timing channel at any given time. (Microcontroller block 150 may still however consider such overlaps and conflicts).

Figure 12C:
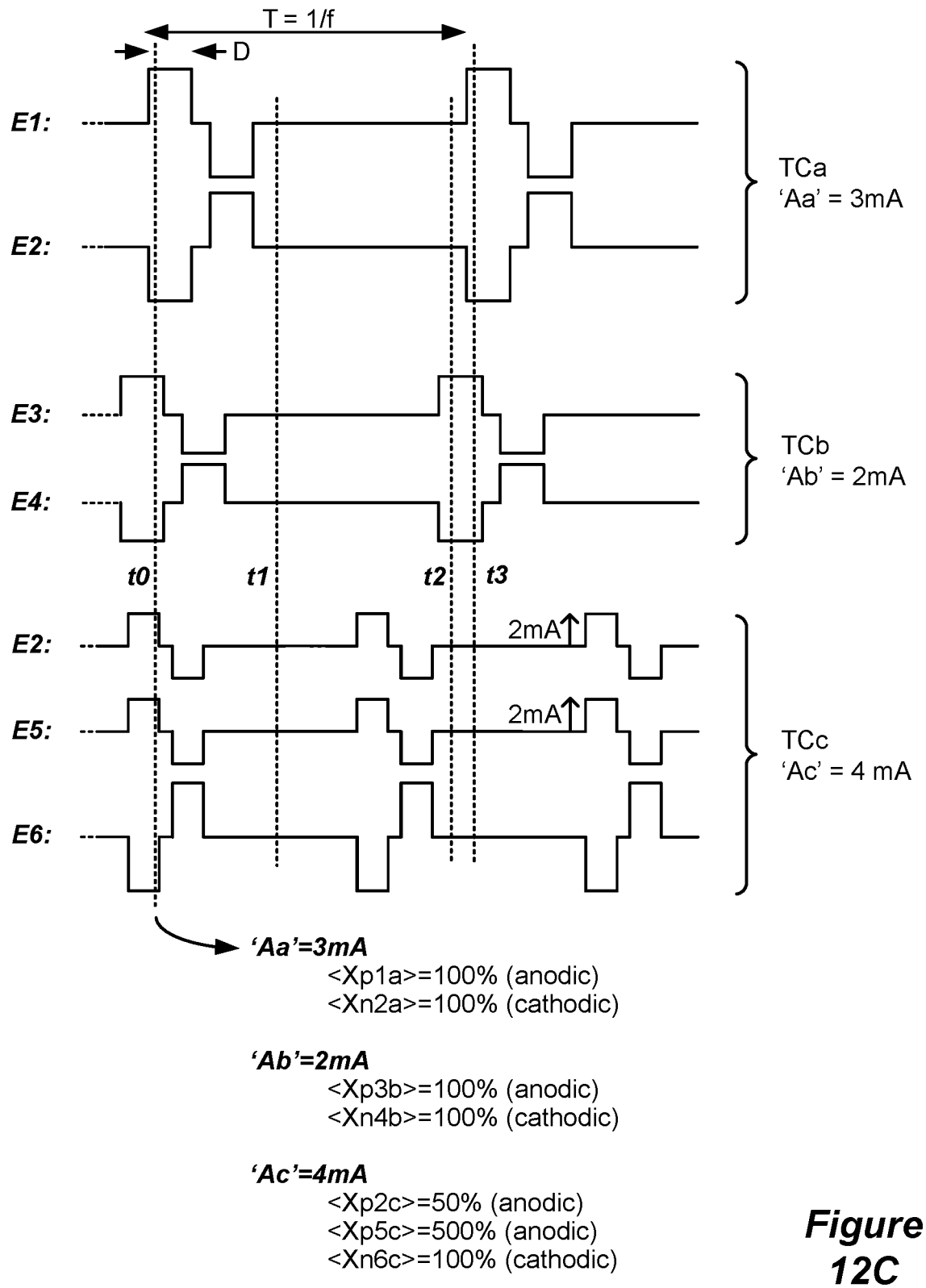

Independence of the timing channels is illustrated in FIG. 12C, which shows the same pulses illustrated earlier in FIG. 8B. At time t1, none of the timing channels TCa, TCb or TCc are issuing pulses, and so amplitudes 'Aa', 'Ab', and 'Ac' may be set to 0; all percentage bus signals <X> in all timing channels may be set to 0 at these times as well.

At time t2, pulses are only issued in timing channel TCb. Accordingly, PDCb sets 'Ab'=2, <Xp3b>=100%, and <Xn4b>=100%, which causes PDAC3b to issue+2 mA and NDAC4b to issue −2 mA, forming the desired pulses at anode electrode E3 and cathode electrode E4. All other amplitudes ('Aa', 'Ac') as well as their corresponding percentage bus control signals (<X>) are set to 0.

At time t3, pulses are issued in both of timing channels TCa and TCb. However, because these timing channels are independent, there is no need to consider the relative amplitudes 'Aa' and 'Ab' in each, or otherwise adjust the percentage control signals in light of the overlap. Thus, PDCa sets 'Aa'=3, <Xp1a>=100%, and <Xn2a>=100% which causes PDAC1b to issue+3 mA and NDAC2b to issue −3 mA, forming the desired pulses at anode electrode E1 and cathode electrode E2 specified by TCa. PDCb sends the same control signals as during time t2 to form the pulses at electrodes E3 and E4.

Time t0 shows a more extensive overlap between the pulses in all of timing channels TCa, TCb, and TCc, but again the independence of the PDCs and timing channels makes definition of the currents at this time more straightforward, and FIG. 12C shows the signals issued by PDCa, PDCb, and PDCc at this time. In this example, the conflict presented by electrode E2 being simultaneously specified as both an anode (in TCc) and a cathode (in TCa) results in shorting current (i.e., 2 mA) internally to the ASIC from PDAC2c to NDAC2a, similar to what was discussed earlier (FIG. 8B).

Figure 12D:
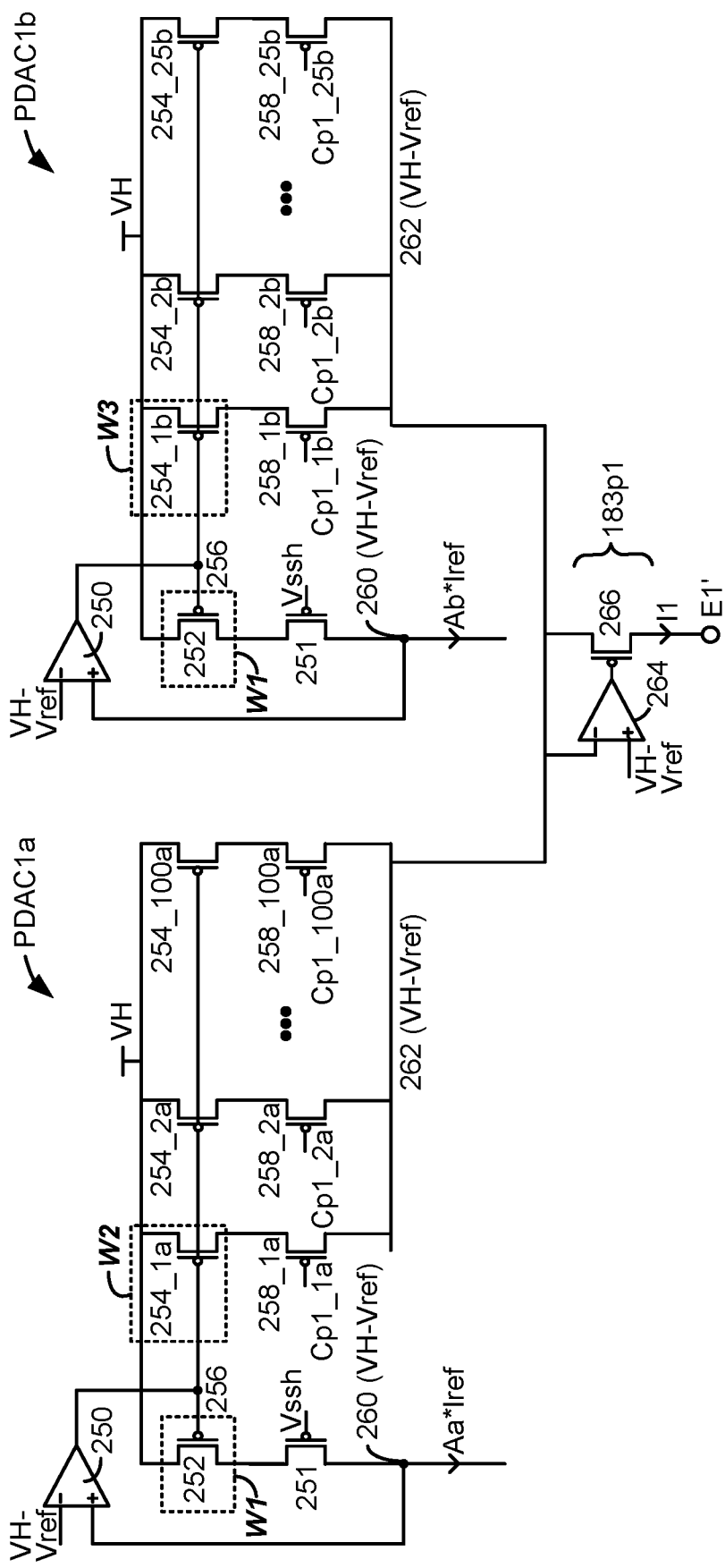
Figure 12E:
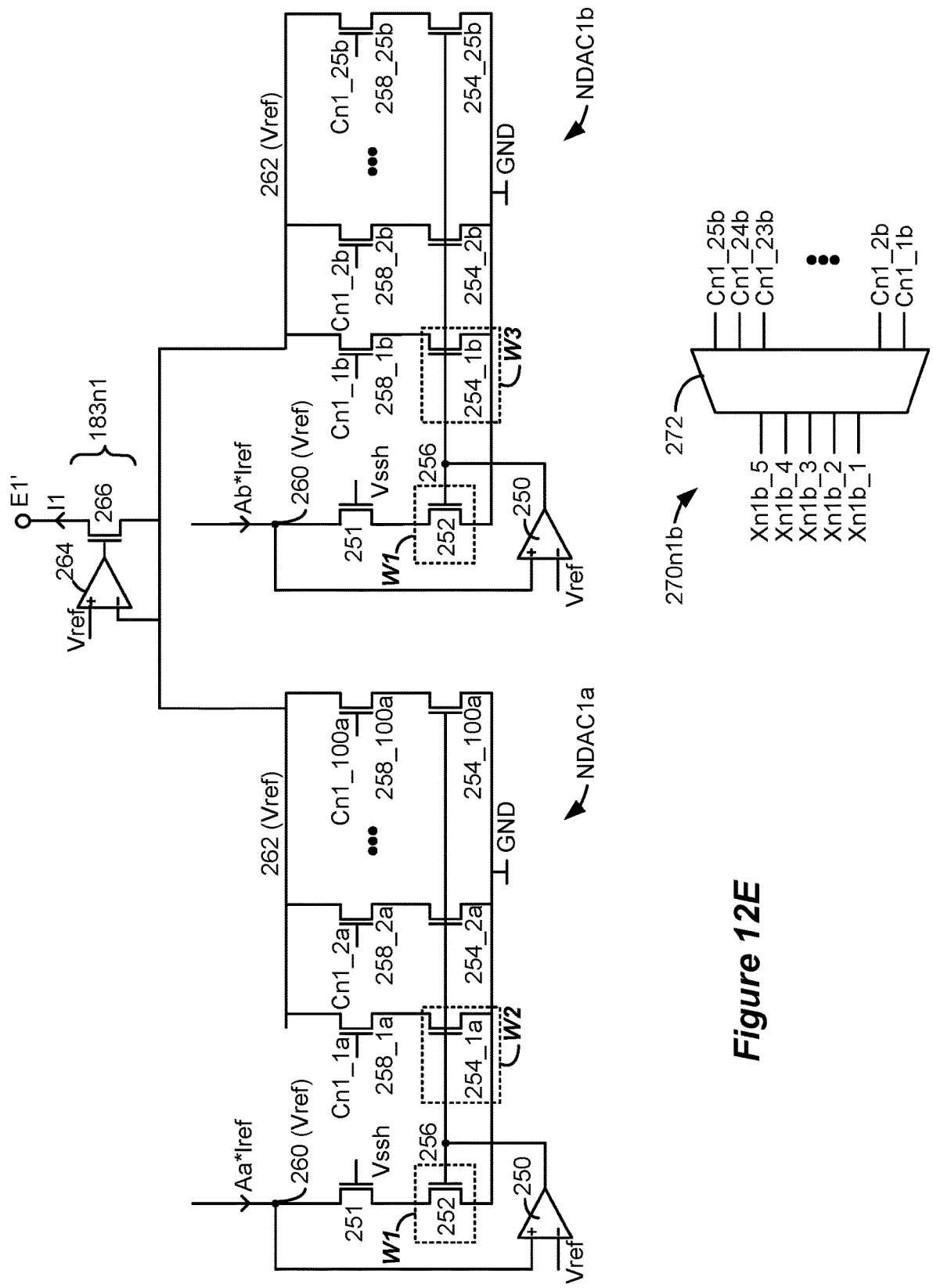

FIG. 12D shows PDAC1a and PDAC1b, while FIG. 12E similarly shows NDAC1a and NDAC1b, that service electrode node E1'. As before, these circuits are symmetrical, and the NDACs of FIG. 12E are discussed.

NDAC1a is essentially the same as NDAC1 described earlier (FIG. 9B), and has 100 branches controlled by switch control signals Cn1_100a:1a. These switch control signals are generated from the percentage control signals <Xn1a> using logic circuitry 270n1a, which would be similar to logic circuitry 270n1 illustrated earlier (FIG. 10A). Logic circuitry 270n1a may once again alter generation of the switch control signals based on resolution control signal Kn1a, thus allowing NDAC1a to steer current in 1% (high resolution) or 4% (low resolution) increments. Notice that NDAC1a receives amplified reference current Aa*Iref from master DAC 180a and distributor 182a (FIG. 12A).

NDAC1b, by contrast, receives amplified reference current Ab*Iref from master DAC 180b and distributor 182b. NDAC1b is also structurally different in this example in that it has only 25 branches controlled by switch control signals Cn1_25b:1b. As mentioned earlier, NDAC1b (actually all PDACs and NDACs operating in timing channel TCb) do not have an adjustable resolution, with each steering current in 4% (low resolution) increments. As a result, logic circuitry 270n1b servicing NDAC1b would be different from logic circuit 270n1a, and would not receive a resolution control signals. A simple illustration of logic circuitry 270n1b is provided in FIG. 12E, which essentially comprises only the thermometer decoder 272 discussed earlier, which directly generates the switch control signals <Cn1b>. Notice in this example only five percentage control signal Xn1b_5:1 are needed to represent the 4% increments (i.e., from 0 to 25, or from 0% to 100%) that NDAC1b must produce. Similar to what was explained earlier for operation in a low resolution mode (e.g., FIG. 10A), notice that PDCb will divide the desired percentage by four and issue that value in binary on percentage control signals Xn1b_5:1.

Another difference of NDAC1b relates to the amplification that each of the branches provides to Ab*Iref. Notice in NDAC1b that the branch transistors 254 are made with a width W3 that is different from the width W2 of the branch transistors 254 in NDAC1a. (The width of the resistance transistor 252 in both NDACs can remain the same at W1). More specifically, in the illustrated example, W2/W1=10, W3/W1=40. This means that the current provided by each selected branch in NDAC1b is four times larger than the current provided by each selected branch in NDAC1a (assuming 'Aa'='Ab'). Notice then that NDAC1a and NDAC1b are each capable of providing the same maximum current to electrode E1 (e.g., −25.5 mA): NDAC1b has branches that carry four times the currents as in NDAC1a, but has only one-fourth of the number of branches.

FIG. 12E shows show other details relevant to the use of two NDACs at each electrode. First, the NDACs share a common output stage 183n1—op amp 264 and output transistor 266—with the tops of the branches in each (node 262) being connected to the bottom of the transistor. Thus, the current in any selected branch in either NDAC1a or NDAC1b will sum at this node 262 and be presented to the electrode node E1'. Also different is the distribution of the reference voltage Vref, which is provided directly to the op amp 250 in each NDAC, and to the op amp 264 in the output stage 183n1.

Generally speaking, if IPG 10 is programmed to provide pulses in only a single timing channel, it is preferred that the microcontroller block 150 assign such pulses to timing channel TCa. This is because TCa—by virtue of PDACia and NDACia and their high number of branches—has the capability to provide both high and low resolutions of current, depending on the value of the resolution control signals Kpia and Knia. This thus allows a clinician or patient to adjust the currents at the electrodes in smaller increments if necessary or desired.

If IPG 10 is programmed to provide pulses in more than one timing channel, the microcontroller block 150 may consider the currents required, and assign the pulses to appropriate timing channels and thus to appropriate PDACs and NDACs. This is shown for example in FIG. 12F, which shows pulses being issued in two timing channels. The pulses at the top comprise only one anode and one cathode, and thus will receive 100% of the total anodic and cathode current ('Ab'=2.4). This can be generated by the low resolution mode PDACs and NDACs dedicated to timing channel TCb, and so the microcontroller block 150 could assign these pulses to this timing channel. By contrast, the pulses at the bottom have (at time t0) two cathode electrodes E1 and E2, each providing 50%. Because the low-resolution, 25 branch PDACs and NDAC in TCb can only split the total current ('Aa'=3.4 mA) in 4% increments, a 50%/50% split cannot be realized (at best, only a 48%/52% split could be realized). Thus, the microcontroller block 150 would preferably assign these pulses to timing channel TCa, which can produce a 50%/50% split in high resolution mode.

Figure 12F:
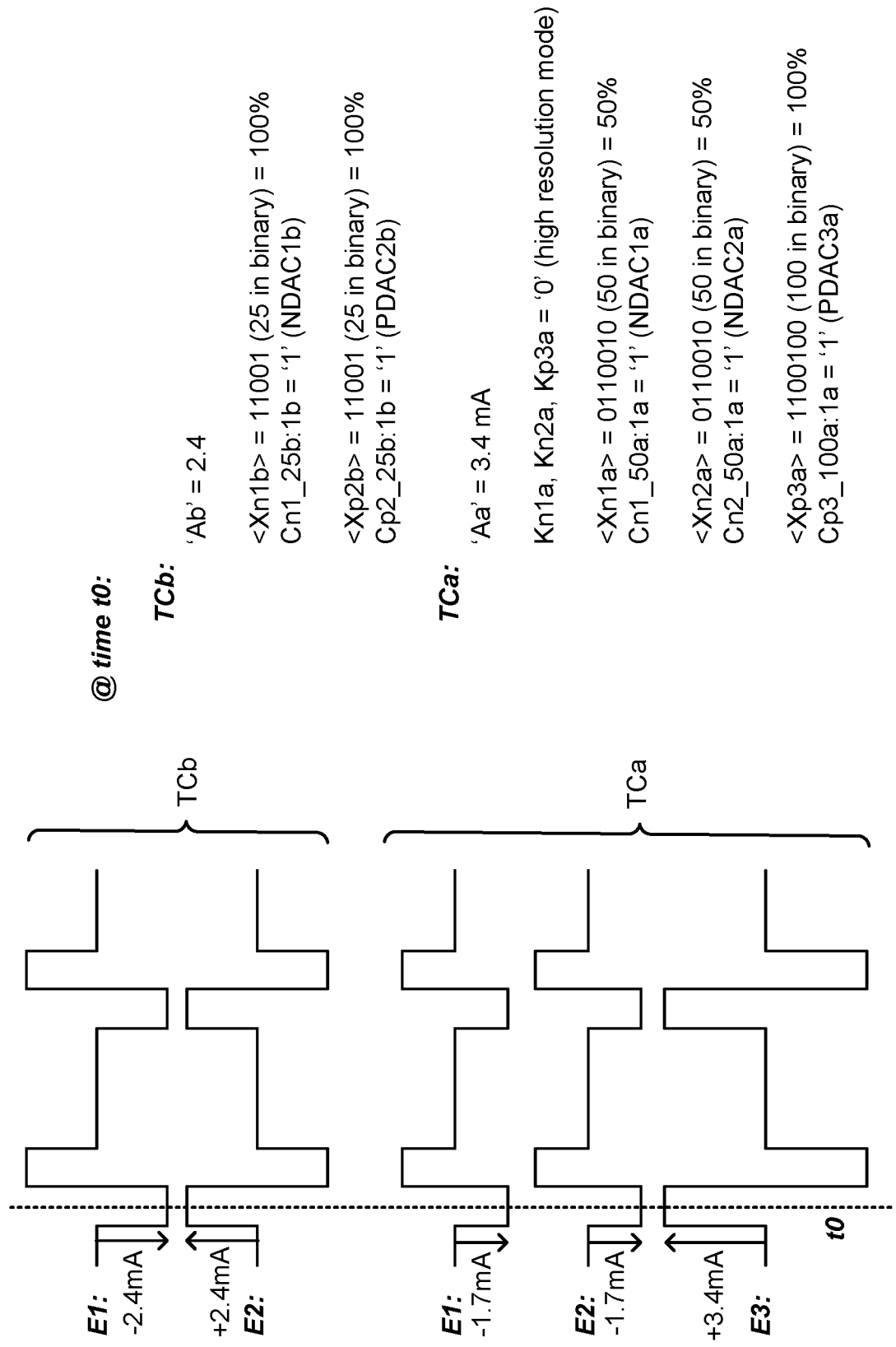

FIG. 12F also shows the control signals issued in the two timing channels TCa and TCb necessary to provide the desired current at the electrodes at time to. A total anodic and cathodic amplitude of 'Ab'=2.4 mA is set in timing channel TCb. Further, each electrodes' TCb percentage bus, <Xn1b> which sets E1 as a cathode, and <Xp2b> which sets E2 as an anode, are set to 100%. As explained earlier, PDCb divides this desired percentage by four (100%/4), and thus issues 25 in binary on the percentage control signals. This causes all 25 branches in NDAC1b (Cn1_25b:1b) and all 25 branches in PDAC2b (Cp2_25b:1b) to be asserted. Notice that no resolution control signal is necessary or provided in TCb.

A total anodic and cathodic amplitude of 'Aa'=3.4 mA is set in timing channel TCa, and the resolution control signals in timing channel TCa for the implicated DACs—NDAC1a, NDAC2a, and (possibly) PDAC3a (Kn1a, Kn2a, Kp3a)—are set to '0' to have these DACs operate in the high resolution mode. Further, the cathode electrodes' percentages busses in timing channel TCa, <Xn1a> for E1 and <Xn2a> for E2, are set to 50%. The anode electrode's percentage bus in timing channel TCa, <Xp3a> for E3, is set to 100%. This causes 50 branches in NDAC1a (Cn1_50a:1a), 50 branches in NDAC2a (Cn2_50a:1a), and all 100 branches in PDAC3a (Cp3_100a:1a) to be asserted.

The effect at electrode E1 (for example) at time t0 can be better appreciated by reviewing NDAC1a and NDAC1b in FIG. 12E. Because all 25 branches in NDAC1b are turned on, those braches contribute 100% of 'Ab'=2.4 mA, which sinks −2.4 mA at node 262. Because 50 branches are on in NDAC1a, those branches contribute 50% of 'Aa'=3.4 mA, which sinks −1.7 mA at node 262. The summed effect is that electrode E1 sinks −2.4 mA+−1.7 mA=−4.1 mA from electrode E1 at time t0.

As noted earlier, the PDAC/NDAC pairs (e.g., PDACia/NDACia; PDACib/NDACib, etc.) at each electrode can all be built the same, and in this regard, each of these pairs can be built with a higher number of branches (e.g., NDAC1a), with resolution being controllable. This however increases the complexity of the signaling on the chip, due to the overhead necessary to generate the 100 switch control signals <C> for each PDAC and NDAC at each electrode (as well as the overhead of the resolution control signals). By contrast, using set lower-resolution PDACs and NDACs at the electrodes with a lower number of branches (e.g., NDAC1b) decreases this complexity. Having both types of PDACs and NDACs at the electrodes (e.g., NDAC1a and NDAC1b) can be a reasonable trade off, as this permits at least one timing channel to have high resolution current adjustment and steering (e.g., NDAC1a), and other simpler timing channels (NDAC1b, etc.) that can be run with lower-resolution adjustment capability. In a preferred example, each electrode can include four PDAC/NDAC pairs, with one pair comprising high resolution DACs with a high number of branches (e.g., PDAC1a/NDAC1a) running in a first timing channel (e.g., TCa), and three pairs comprising low resolution DACs with a smaller number of branches (e.g., PDAC1b/NDAC1b, PDAC1c/NDAC1c, PDAC1c/NDAC1c) running in three other timing channels (e.g., TCb, TCc, and TCd).

In a further modification, the resolution of all PDACs and NDACs can be set, thus obviating the need for resolution control signals (K) altogether. In this instance, the resolution of a given PDAC or NDAC can simply be set by the number of branches it has: for example 100 branches would provide a 1% resolution; 50 branches would provide a 2% resolution, 25 branches would provide a 4% resolution, etc. While not strictly necessary, it may be advisable to vary the amount by which each branch amplifies the reference current (A*Iref) in accordance with the resolution at hand, so that each PDAC or NDAC can provide the same maximum amount of current. For example, if 100 branches are used, each branch may amplify A*Iref by 10 (by adjusting W2/W1 as described earlier); if 50 branches are used, each branch may amplify A*Iref by 20; if 25 branches are used, each branch may amplify A*Iref by 40, etc.

In another alternative, more than one PDAC, NDAC, or PDAC/NDAC pair, could be assigned to a single timing channel. For example, PDAC1a/NDAC1a and PDAC1b/NDAC1b could be assigned to TCa and controlled by a PDCa; PDACc/NDACc and PDAC1d/NDAC1d could be assigned to TCb and controlled by a PDCb, etc. Such assignment could be permanent, or assignment of particular DACs to timing channels may be adjustable, such that PDAC1a/NDAC1a and PDAC1b/NDAC1b can be assigned to TCa at one time, or with PDAC1a/NDAC1a assigned to TCa and PDAC1b/NDAC1b assigned to TCb at another time.

As noted earlier, the improved DAC circuitry 172 can include different power supply voltages (compliance voltage VH, Vssh, Vcc, ground) defining a high power domain (VH/Vssh) and a low power domain (Vcc/GND). Low power domain Vcc/GND is more straight forward, because Vcc and ground may not change, and because Vcc can be generated from the voltage of the battery 14 (FIG. 1C) in the IPG 10 (see 204, FIG. 13B). By contrast, the compliance voltage VH can vary. Variation of the compliance voltage VH was explained briefly in the Introduction, and is elaborated upon further with respect to FIG. 13A. The resistance through the patient tissue, Rt, may not be known or may change over time, and hence the voltage dropped across the tissue in response to a stimulation current I (Vrt=I*Rt) may also change. Measuring the voltage drops across an active PDAC (Vp) and an active NDAC circuit (Vn) can assist in determining the tissue's voltage drop and resistance, and hence whether compliance voltage VH should be increased or decreased. Thus, in FIG. 13A, the compliance voltage generator block 76 (FIG. 4B) that produces the compliance voltage VH receives the measured PDAC and NDAC voltages drops Vp and Vn, and adjusts compliance voltage VH accordingly.

Further, the compliance voltage VH may be set to voltages that are relatively large, such as from 6 to 15 Volts. Higher voltage requirements have generally required PDACs and NDACs to be formed of special high-voltage transistors. Such high-voltage transistors are generally larger and more complicated to fabricate compared to more-standard, smaller logic transistors, because they are designed to function when receiving high voltages at their gates (i.e., Vg=0 to VH), and when receiving high voltages between their drains and sources (i.e. Vds=0 to VH). Even if the compliance voltage is normally not required to operate at its maximum voltage (e.g., 15V), DAC circuitry transistors have traditionally been built to withstand the possibility of high voltages, which complicates design of the ASIC.

It is beneficial to provide circuitry operating in low and high power domains in the DAC circuitry 172, because this can enable many transistors in the DAC circuitry 172 to be made from more-standard, smaller logic transistors otherwise generally used to form logic gates in the ASIC 160. For example, and preferably, if Vssh is set to 3.3 Volts lower than VH in the high power domain, low voltage transistors can be used in such high power domain circuits, so long as any control signals to such transistors are also biased in this domain. Likewise, and preferably if Vcc is set to 3.3 Volts higher than ground in the low power domain, low voltage transistors can be used in such low power domain circuits, again so long as any control signals to such transistors are also biased in this domain.

FIG. 13B shows generator circuitry 202, 204 used respectively to generate voltages Vssh and Vcc. Both of these generators 202, 204 comprise linear voltage regulators and include an op amp 206 that controls a pass transistor 210 to set Vssh and Vcc. As these circuits are disclosed and discussed in U.S. Patent Application Publication 2018/0071520, they are not further discussed here. Note though that even though VH may vary as described earlier, the output of Vssh generator 202 is always (in this example) 3.3 V lower than VH, as set by the resistor R and current source 208. Note also that Vcc may also be used to power other circuitry in the IPG 10, such as various functional blocks included in the ASIC 160 (FIG. 4B).

Figure 14A:
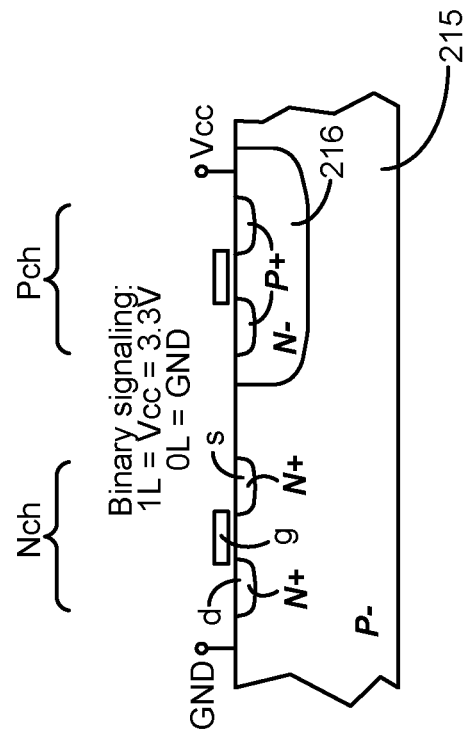
FIG. 14A shows cross sections of the N- and P-channel transistors used in circuitry powered in the low and high power domains, and shows how they are biased.
Figure 14A:
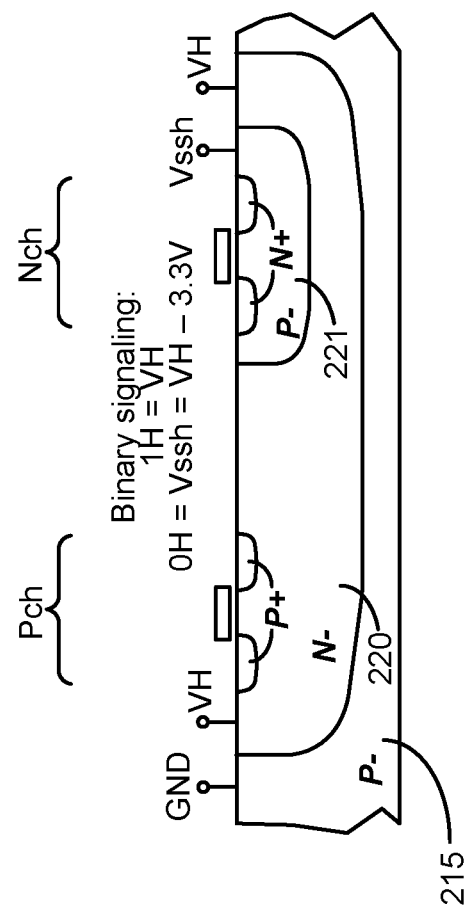

As noted earlier, the transistors in a particular power domain are preferably biased in accordance with that domain. This is shown in FIG. 14A, which shows cross-sectional views of the monolithic substrate 215 of the ASIC 160. Circuitry in low and high power domains include both low-voltage N-channel (Nch) and low-voltage P-channel (Pch) transistors. For example, N-channel transistors in the high power domain include transistors 192-200 in the distributor 182p (FIG. 7A), and any N-channel transistors in op amps 250 or 264 in the PDACs (FIG. 9A). P-channel transistors in the high power domain include transistors 184-186 in the master DAC 180p (FIG. 7A), any P-channel transistors in op amps 250 or 264 in the PDACs (FIG. 9A), and dummy transistors 251, resistance transistors 252, and branch and switch transistors 254 and 258 in the PDACs (FIG. 9A). N-channel transistors in the low power domain include transistors 184-186 in the master DAC 180n (FIG. 7B), any N-channel transistors in op amps 250 or 264 in the NDACs (FIG. 9B), and dummy transistors 251, resistance transistors 252, and branch and switch transistors 254 and 258 in the NDACs (FIG. 9B). P-channel transistors in the low power domain include transistors 192-200 in the distributor 182n (FIG. 7B), and any P-channel transistors in op amps 250 or 264 in the NDACs (FIG. 9B).

As FIG. 14A shows, the low power domain transistors are essentially formed as is common in CMOS technologies, with the N-channel transistors built into a grounded P-type substrate 215, and the P-channel transistors built in an N-well 216 biased to Vcc=3.3 V. In other words, the low power domain transistors are biased to the Vcc/ground low power domain. The high power domain transistors are biased to the VH/Vssh high power domain. Thus, a high-voltage N-well 220 is formed in the P-type substrate 215, and biased to the compliance voltage VH. This high voltage N-well 220 may be deeper and significantly graded so that it may retain the high compliance voltage VH (which may be up to 15 Volts) without breaking down to the grounded substrate 215. P-channel transistors are built in the high-voltage N-well 220. A P-well 221 is formed in the N-well 220, in which the N-channel transistors may be built.

As explained further below, the logic levels (e.g., control signals) presented to the transistors in the power domains are also biased in accordance with each power domain. Thus, a logic '0' in the low power domain (0L) equals ground, while a logic '1' (1L) equals Vcc=3.3V. A logic '0' in the high power domain (0H) equals Vssh, while a logic '1' (1H) equals VH–Vssh. Thus, voltage drops in the low and high power domain transistors will not exceed e.g., 3.3 Volts, and thus low-voltage transistors can be used. (The only high-voltage transistors that may be warranted in the design of DAC circuitry 172 are the output transistors 266 (FIGS. 9A, 9B) used to pass currents to the selected electrode nodes 61a, and transistors used to form the op amps 264. As such, the op amps 264 may also receive high voltage power (VH), although this detail isn't shown in the figures).

Figure 14B:
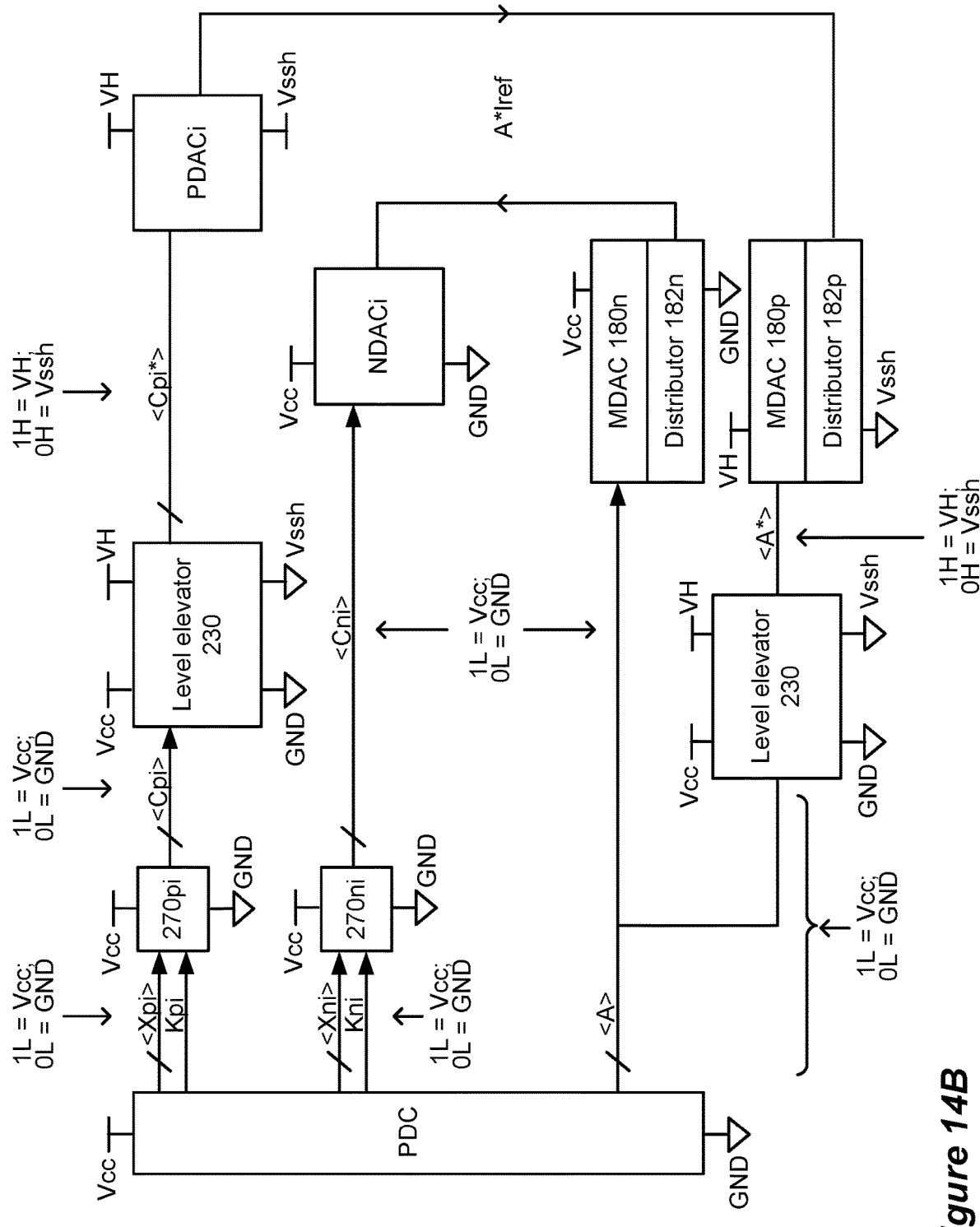
FIG. 14B shows how control signals sent to the PDACs can be level elevated from the low power domain to the high power domain.
Figure 14C:
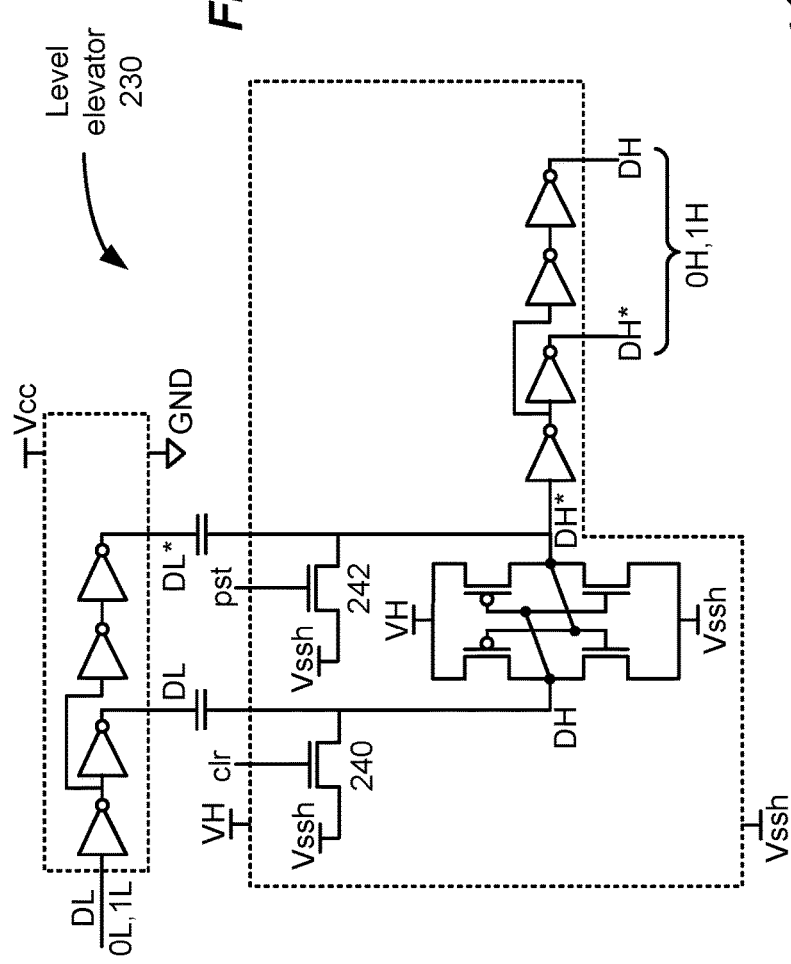
FIG. 14C shows example level elevation circuitry for each control signal.

How control signals sent to various transistors in the DAC circuitry 172 are referenced to the appropriate power domain is discussed next. Control signals are ultimately issued from one or more pulse definition circuits (PDCs), as discussed earlier. As shown in FIG. 14B, because the PDC(s) are powered by Vcc and ground, NDAC control signals (<Xni>, Kni), PDAC control signals (<Xpi>, Kpi), and the amplitude bus <A> are issued with low-power-domain logic states (i.e., 0L, 1L).

The NDAC control signals (<Xni>, Kni) and the PDAC control signals (<Xpi>, Kpi) are sent to logic circuitries 270ni and 270pi used to convert these signals into switch control signals <Cni> and <Cpi> for the NDACs and the PDACs, as already discussed (e.g., FIG. 10A). Because logic circuitries 270ni and 270pi are also biased in the lower power domains, the switch control signals <Cni> and <Cpi> are also issued with low-power-domain logic states 0L and 1L.

Because the NDACs are also biased in the low power domain, the NDACs can receive the switch control signals <Cni> directly as issued by logic circuitry 270ni. By contrast, the PDACs operate in the high power domain, and therefore, each <Cpi> control signals destined for the PDACs is sent to a level elevator 230 to increase the voltage of the signal, as shown in FIG. 14B. Circuitry for the level elevator 230 is shown in detail in FIG. 14C. Because operation of level elevator 230 is disclosed and discussed in U.S. Published Patent Application 2018/0071520, it is not further discussed in detail here. Briefly, each individual data bit in <Cpi> (DL, which may comprise either 0L or 1L) is presented to the level elevator 230, which operates to boost the voltages of that data bit from low-power-domain voltages to high-power-domain voltages (DH, which may comprise either 0H or 1H), thus matching the high power domain to which the PDACs are biased. Notice that the level elevator can provide both true (DH) and complementary (DH*) outputs. The complementary outputs <Cpi*> are preferably used as these will enable the P-channel switches 258 (FIG. 9A) in the PDACs with the correct logic state.

(Transistors 240 and 242 in the level elevators 230 receive signals clear (clr) and preset (pst), which are useful upon initial powering of the ASIC 160 because the latches 244 in the level elevators 230 may power to an indefinite state that is inconsistent with the input, DL. Thus, one of these signals clr or pst can be asserted after power-up to pre-condition the latch 244 to match the current input value DL. For example, if DL=0L, clr can be asserted; if DL=1L, pst can be asserted).

The bits in amplitude bus <A> as issued by the PDC in the low power domain (0L, 1L) may be sent directly to the MDAC 180n, as they match the low power domain to which MDAC 180n and its distributor 182n are biased. By contrast, the MDAC 180p and its distributor 182p contain transistors biased in the high power domain, and thus the amplitude signals <A> must be shifted to the high power domain (0H, 1H) using level elevators 230. Again, the complementary outputs <A*> are preferably used at the level elevator 230 outputs as these will enable the P-channel switches 184 (FIG. 7A) in the MDAC 180p with the correct logic state.

Note that the high power domain transistors can use low-voltage transistors even though the compliance voltage VH may change over time. If VH changes, so too will Vssh, as dictated by the operation of the Vssh generator 202 (FIG.

Figure 14D:
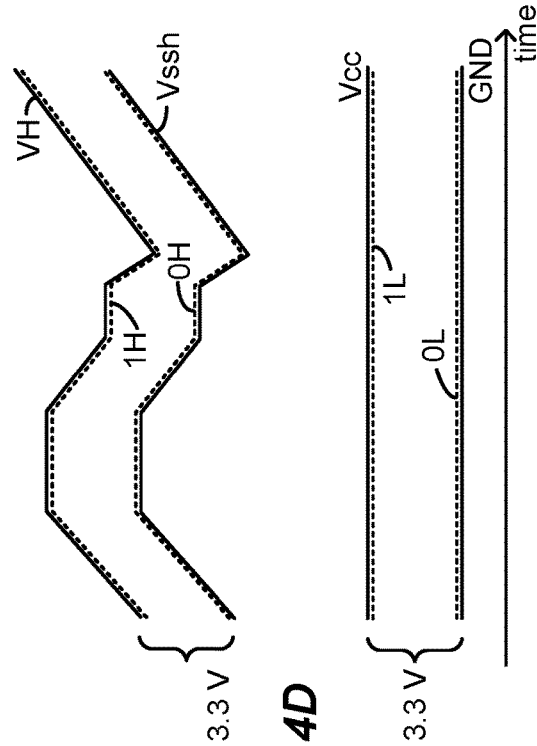
FIG. 14D shows how the high power domain and its logic levels can vary as the compliance voltage changes.

14B), which always maintains a 3.3 V difference between VH and Vssh in the high power domain. If VH and Vssh change, so will the biasing of the high power domain transistors in the PDACs (FIG. 14A), and so too will the voltages of the logic states (0H, 1H) presented to those transistors (per operation of the level elevators 230 of FIG. 14C). This is shown in FIG. 14D, which shows that as the compliance voltage VH varies over time, so too does Vssh, and so do the voltages of the logic states 0H, 1H produced by the level elevators 230. Moreover, a constant difference (e.g., 3.3 V) is also maintained between the two logic states despite variance in VH and Vssh. FIG. 14D also shows the power supplies for the low power domain (Vcc, ground) and the voltages of the logic states in this low power domain (0L, 1L), which also maintain a constant difference (again, e.g., 3.3 V).

While disclosed in the context of an implantable pulse generator, it should be noted that the improved stimulation circuitry 170 and DAC circuitry 172 could also be implemented in a non-implantable pulse generator, such as an External Trial Stimulator (ETS). See, e.g., U.S. Pat. No. 9,259,574 (describing an ETS).

Because defining a positive or negative current can be a matter of convention, anodic currents are not necessarily positive (or sourced to the tissue, such as from the disclosed PDACs) and cathodic currents are not necessarily negative (or sunk from the tissue, such as from the disclosed NDACs), as has been described to this point. Instead, anodic currents can also be considered as negative (sunk from the tissue, such as are producible by the disclosed NDACs), and cathodic currents can be considered as positive (sourced to the tissue, such as are producible by the disclosed PDACs). What is important then is that anodic and cathodic currents have opposite polarities.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A pulse generator, comprising:
a plurality of electrode nodes, each electrode node configured to be coupled to a corresponding electrode configured to contact a patient's tissue; and
a plurality of first digital-to-analog converters (DACs), wherein each of the first DACs is dedicated to a different one of the electrode nodes and is configured to receive a first current with a magnitude indicative of a total anodic current amplitude to be produced at the electrode nodes, wherein each of the first DACs is configured to provide an anodic stimulation current to only its dedicated electrode node,
wherein each first DAC comprises a plurality of first branches, wherein each first branch is configured when selected to produce an amplified version of the first current, and wherein the amplified first current at each selected first branch is summed to produce the anodic stimulation current at its dedicated electrode.

2. The pulse generator of claim 1, wherein a sum of the anodic stimulation currents at the electrode nodes equals the total anodic current amplitude.

3. The pulse generator of claim 1, further comprising:
a plurality of second DACs, wherein each of the second DACs is dedicated to a different one of the electrode nodes and is configured to receive a second current with a magnitude indicative of a total cathodic current amplitude to be produced at the electrode nodes, wherein each of the second DACs is configured to provide a cathodic stimulation current to only its dedicated electrode node,
wherein each second DAC comprises a plurality of second branches, wherein each second branch is configured when selected to produce an amplified version of the second current, and wherein the amplified second current at each selected second branch is summed to produce the cathodic stimulation current at its dedicated electrode.

4. The pulse generator of claim 3, wherein the anodic stimulation currents are either sourced to or sunk from the patient's tissue, and wherein the cathodic stimulation currents are the other of sourced to or sunk from the patient's tissue.

5. The pulse generator of claim 3, wherein the magnitude of the first and second currents are equal but of opposite polarities.

6. The pulse generator of claim 3, wherein a sum of the cathodic stimulation currents at the electrode nodes equals the total cathodic current amplitude.

7. The pulse generator of claim 3, wherein outputs of the first and second DACs which are dedicated to a same electrode node are connected together at the same electrode node, and wherein each electrode node is configured to be coupled to its corresponding electrode via a DC-blocking capacitor.

8. The pulse generator of claim 1, wherein each first branch comprises a series connection of a second resistance and a selection transistor each receiving a first control signal for selecting the first branch.

9. The pulse generator of claim 8, wherein the plurality of first branches in each first DAC are connected between a second node and a reference potential, wherein the amplified first current at each selected first branch is summed at the second node to produce the anodic stimulation current at its dedicated electrode node.

10. The pulse generator of claim 9, wherein each first DAC further comprises a first resistance configured to receive the first current at a first node, wherein a reference voltage is dropped across the first resistance.

11. The pulse generator of claim 10, wherein the reference voltage is dropped across each of the second resistances in the plurality of first branches.

12. The pulse generator of claim 11, wherein the first resistance and the second resistance comprise transistors, and wherein gates of the transistors are connected.

13. The pulse generator of claim 10, wherein each first DAC comprises an output stage comprising a transistor controlled by an operational amplifier, wherein the first and second nodes comprise inputs to the operational amplifier.

14. The pulse generator of claim 1, further comprising a plurality of logic circuitries, wherein each logic circuitry is configured to generate first control signals for selecting the first branches in a different associated first DAC.

15. The pulse generator of claim 14, wherein each logic circuitry receives a percentage bus indicating a percentage of the total anodic current amplitude that its associated first DAC will produce as the anodic stimulation current at its dedicated electrode node.

16. The pulse generator of claim 14, wherein each logic circuitry receives at least one resolution control signal configured to set how many first branches can be selected at one time to produce the anodic stimulation current at its dedicated electrode node.

17. The pulse generator of claim 1, further comprising at least one implantable lead, wherein the electrodes are located on the lead.

18. The pulse generator of claim 1, further comprising a conductive case, wherein one of the plurality of electrodes comprises the conductive case.

19. A method for controlling a pulse generator having a plurality of electrode nodes, each electrode node configured to be coupled to a corresponding electrode configured to contact a patient's tissue, the method comprising:
  providing a first current to each of a plurality of first digital-to-analog converters (DACs), wherein each of the first DACs is dedicated to provide an anodic stimulation current to a different dedicated one of the electrode nodes, wherein each first current has a magnitude indicative of a total anodic current amplitude to be produced at the electrode nodes, wherein each first DAC comprises a plurality of first branches; and
  selecting one or more first branches in at least one of the first DACs to produce an amplified version of the first current, wherein the amplified first current at each selected first branch in each of the first DACs is summed to produce the anodic stimulation current at its dedicated electrode.

20. A method for controlling a pulse generator having a plurality of electrode nodes, each electrode node configured to be coupled to a corresponding electrode configured to contact a patient's tissue, the method comprising:
  providing a first current to each of a plurality of first digital-to-analog converters (DACs), wherein each one of the first DACs is dedicated to provide an anodic stimulation current to a different dedicated one of the electrode nodes, wherein each first current has a magnitude indicative of a total anodic current amplitude to be produced at the electrode nodes;
  providing a plurality of first control signals to each of the first DACs, wherein the first control signals indicate a percentage of the total anodic current amplitude that each first DAC will produce as the anodic stimulation current at its dedicated electrode node.

* * * * *